(12) United States Patent
Kiaie et al.

(10) Patent No.: US 8,930,203 B2
(45) Date of Patent: Jan. 6, 2015

(54) MULTI-FUNCTION ANALYTE TEST DEVICE AND METHODS THEREFOR

(75) Inventors: Namvar Kiaie, Danville, CA (US); Jean-Pierre Cole, Tracy, CA (US); Mark Kent Sloan, Redwood City, CA (US); Frederic Arbogast, San Ramon, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 511 days.

(21) Appl. No.: 12/699,844

(22) Filed: Feb. 3, 2010

(65) Prior Publication Data

US 2010/0204557 A1 Aug. 12, 2010

Related U.S. Application Data

(63) Continuation-in-part of application No. 12/032,617, filed on Feb. 15, 2008.

(60) Provisional application No. 61/149,989, filed on Feb. 4, 2009, provisional application No. 60/890,492, filed on Feb. 18, 2007.

(51) Int. Cl.

| G06F 17/30 | (2006.01) |
|---|---|
| A61B 5/00 | (2006.01) |
| A61N 1/00 | (2006.01) |
| C12M 1/00 | (2006.01) |
| A61B 5/145 | (2006.01) |
| G06F 19/00 | (2011.01) |

(52) U.S. Cl.
CPC ............ *A61B 5/411* (2013.01); *A61B 5/14532* (2013.01); *G06F 19/3456* (2013.01); *G06F 19/3406* (2013.01)
USPC .................................................. 705/1; 705/3

(58) Field of Classification Search
CPC ................... A61B 5/14532; A61B 2562/0295; A61B 5/4839; A61B 5/0002; A61B 5/411; G06F 19/3456

USPC ............................................................ 705/1
See application file for complete search history.

(56) References Cited

U.S. PATENT DOCUMENTS

| 2,755,036 A | 7/1956 | Mikko |
|---|---|---|
| 3,260,656 A | 7/1966 | Ross, Jr. |

(Continued)

FOREIGN PATENT DOCUMENTS

| AU | 2003/259741 | 2/2004 |
|---|---|---|
| CA | 2495648 | 2/2004 |

(Continued)

OTHER PUBLICATIONS

Mougiakakou, et al., "A Real Time Simulation Model of Glucose-Insulin Metabolism for Type 1 Diabetes Patients", *Proceedings of the 2005 IEEE*, 2005, pp. 298-301.

(Continued)

*Primary Examiner* — Hiep V Nguyen
(74) *Attorney, Agent, or Firm* — Jackson & Co., LLP

(57) ABSTRACT

Methods, device and systems including receiving a request for a therapy profile for treating a medical condition, determining using a processor a plurality of therapy profile parameters, assigning a weighted value to each therapy profile parameter based on a hierarchy determined by the medical condition, querying a database to identify a stored therapy profile with therapy profile parameters that most closely correspond to the determined plurality of therapy profile parameters based on the hierarchy, generating an output data corresponding to the identified stored therapy profile, the output data a medication dosage information are provided. Also provided are systems and kits.

46 Claims, 21 Drawing Sheets

(56) References Cited

U.S. PATENT DOCUMENTS

| | | |
|---|---|---|
| 3,304,413 A | 2/1967 | Lehmann et al. |
| 3,581,062 A | 5/1971 | Aston |
| 3,651,318 A | 3/1972 | Czekajewski |
| 3,653,841 A | 4/1972 | Klein |
| 3,698,386 A | 10/1972 | Fried |
| 3,719,564 A | 3/1973 | Lilly, Jr. et al. |
| 3,768,014 A | 10/1973 | Smith et al. |
| 3,776,832 A | 12/1973 | Oswin et al. |
| 3,837,339 A | 9/1974 | Aisenberg et al. |
| 3,919,051 A | 11/1975 | Koch et al. |
| 3,923,060 A | 12/1975 | Ellinwood, Jr. |
| 3,926,760 A | 12/1975 | Allen et al. |
| 3,949,388 A | 4/1976 | Fuller |
| 3,972,320 A | 8/1976 | Kalman |
| 3,979,274 A | 9/1976 | Newman |
| 4,003,379 A | 1/1977 | Ellinwood, Jr. |
| 4,008,717 A | 2/1977 | Kowarski |
| 4,016,866 A | 4/1977 | Lawton |
| 4,036,749 A | 7/1977 | Anderson |
| 4,055,175 A | 10/1977 | Clemens et al. |
| 4,059,406 A | 11/1977 | Fleet |
| 4,076,596 A | 2/1978 | Connery et al. |
| 4,098,574 A | 7/1978 | Dappen |
| 4,100,048 A | 7/1978 | Pompei et al. |
| 4,129,128 A | 12/1978 | McFarlane |
| 4,151,845 A | 5/1979 | Clemens |
| 4,154,231 A | 5/1979 | Russell |
| 4,168,205 A | 9/1979 | Danninger et al. |
| 4,172,770 A | 10/1979 | Semersky et al. |
| 4,178,916 A | 12/1979 | McNamara |
| 4,206,755 A | 6/1980 | Klein |
| 4,224,125 A | 9/1980 | Nakamura et al. |
| 4,240,438 A | 12/1980 | Updike et al. |
| 4,240,889 A | 12/1980 | Yoda et al. |
| 4,245,634 A | 1/1981 | Albisser et al. |
| 4,247,297 A | 1/1981 | Berti et al. |
| 4,271,449 A | 6/1981 | Grogan |
| 4,318,784 A | 3/1982 | Higgins et al. |
| 4,327,725 A | 5/1982 | Cortese et al. |
| 4,331,869 A | 5/1982 | Rollo |
| 4,340,458 A | 7/1982 | Lerner et al. |
| 4,344,438 A | 8/1982 | Schultz |
| 4,349,728 A | 9/1982 | Phillips et al. |
| 4,352,960 A | 10/1982 | Dormer et al. |
| 4,356,074 A | 10/1982 | Johnson |
| 4,365,637 A | 12/1982 | Johnson |
| 4,366,033 A | 12/1982 | Richter et al. |
| 4,375,399 A | 3/1983 | Havas et al. |
| 4,384,586 A | 5/1983 | Christiansen |
| 4,390,621 A | 6/1983 | Bauer |
| 4,392,933 A | 7/1983 | Nakamura et al. |
| 4,401,122 A | 8/1983 | Clark, Jr. |
| 4,404,066 A | 9/1983 | Johnson |
| 4,407,959 A | 10/1983 | Tsuji et al. |
| 4,417,588 A | 11/1983 | Houghton et al. |
| 4,418,148 A | 11/1983 | Oberhardt |
| 4,420,564 A | 12/1983 | Tsuji et al. |
| 4,425,920 A | 1/1984 | Bourland et al. |
| 4,427,004 A | 1/1984 | Miller et al. |
| 4,427,770 A | 1/1984 | Chen et al. |
| 4,431,004 A | 2/1984 | Bessman et al. |
| 4,436,094 A | 3/1984 | Cerami |
| 4,440,175 A | 4/1984 | Wilkins |
| 4,441,968 A | 4/1984 | Emmer et al. |
| 4,444,892 A | 4/1984 | Malmros |
| 4,450,842 A | 5/1984 | Zick et al. |
| 4,458,686 A | 7/1984 | Clark, Jr. |
| 4,461,691 A | 7/1984 | Frank |
| 4,462,048 A | 7/1984 | Ross |
| 4,464,170 A | 8/1984 | Clemens et al. |
| 4,467,811 A | 8/1984 | Clark, Jr. |
| 4,469,110 A | 9/1984 | Slama |
| 4,477,314 A | 10/1984 | Richter et al. |
| 4,478,976 A | 10/1984 | Goertz et al. |
| 4,483,924 A | 11/1984 | Tsuji et al. |
| 4,484,987 A | 11/1984 | Gough |
| 4,494,950 A | 1/1985 | Fischell |
| 4,509,531 A | 4/1985 | Ward |
| 4,512,348 A | 4/1985 | Uchigaki et al. |
| 4,522,690 A | 6/1985 | Venkatasetty |
| 4,524,114 A | 6/1985 | Samuels et al. |
| 4,526,661 A | 7/1985 | Steckhan et al. |
| 4,527,240 A | 7/1985 | Kvitash |
| 4,534,356 A | 8/1985 | Papadakis |
| 4,538,616 A | 9/1985 | Rogoff |
| 4,543,955 A | 10/1985 | Schroeppel |
| 4,545,382 A | 10/1985 | Higgins et al. |
| 4,552,840 A | 11/1985 | Riffer |
| 4,560,534 A | 12/1985 | Kung et al. |
| 4,569,589 A | 2/1986 | Neufeld |
| 4,571,292 A | 2/1986 | Liu et al. |
| 4,573,994 A | 3/1986 | Fischell et al. |
| 4,581,336 A | 4/1986 | Malloy et al. |
| 4,595,011 A | 6/1986 | Phillips |
| 4,595,479 A | 6/1986 | Kimura et al. |
| 4,601,707 A | 7/1986 | Albisser et al. |
| 4,619,754 A | 10/1986 | Niki et al. |
| 4,619,793 A | 10/1986 | Lee |
| 4,627,445 A | 12/1986 | Garcia et al. |
| 4,627,908 A | 12/1986 | Miller |
| 4,633,878 A | 1/1987 | Bombardien |
| 4,633,881 A | 1/1987 | Moore et al. |
| 4,637,403 A | 1/1987 | Garcia et al. |
| 4,648,408 A | 3/1987 | Hutcheson et al. |
| 4,650,547 A | 3/1987 | Gough |
| 4,653,513 A | 3/1987 | Dombrowski |
| 4,654,197 A | 3/1987 | Lilja et al. |
| 4,655,880 A | 4/1987 | Liu |
| 4,655,885 A | 4/1987 | Hill et al. |
| 4,658,463 A | 4/1987 | Sugita et al. |
| 4,671,288 A | 6/1987 | Gough |
| 4,674,652 A | 6/1987 | Aten et al. |
| 4,679,562 A | 7/1987 | Luksha |
| 4,680,268 A | 7/1987 | Clark, Jr. |
| 4,682,602 A | 7/1987 | Prohaska |
| 4,684,537 A | 8/1987 | Graetzel et al. |
| 4,685,463 A | 8/1987 | Williams |
| 4,685,903 A | 8/1987 | Cable et al. |
| 4,686,624 A | 8/1987 | Blum et al. |
| 4,703,756 A | 11/1987 | Gough et al. |
| 4,711,245 A | 12/1987 | Higgins et al. |
| 4,717,673 A | 1/1988 | Wrighton et al. |
| 4,721,601 A | 1/1988 | Wrighton et al. |
| 4,721,677 A | 1/1988 | Clark, Jr. |
| 4,726,378 A | 2/1988 | Kaplan |
| 4,726,716 A | 2/1988 | McGuire |
| 4,731,726 A | 3/1988 | Allen, III |
| 4,749,985 A | 6/1988 | Corsberg |
| 4,750,496 A | 6/1988 | Reinhardt |
| 4,757,022 A | 7/1988 | Shults et al. |
| 4,758,323 A | 7/1988 | Davis et al. |
| 4,759,371 A | 7/1988 | Franetzki |
| 4,759,828 A | 7/1988 | Young et al. |
| 4,764,416 A | 8/1988 | Ueyama et al. |
| 4,776,944 A | 10/1988 | Janata et al. |
| 4,777,953 A | 10/1988 | Ash et al. |
| 4,779,618 A | 10/1988 | Mund et al. |
| 4,781,798 A | 11/1988 | Gough |
| 4,784,736 A | 11/1988 | Lonsdale et al. |
| 4,795,707 A | 1/1989 | Niiyama et al. |
| 4,796,634 A | 1/1989 | Huntsman et al. |
| 4,803,625 A | 2/1989 | Fu et al. |
| 4,805,624 A | 2/1989 | Yao et al. |
| 4,813,424 A | 3/1989 | Wilkins |
| 4,815,469 A | 3/1989 | Cohen et al. |
| 4,820,399 A | 4/1989 | Senda et al. |
| 4,822,337 A | 4/1989 | Newhouse et al. |
| 4,830,959 A | 5/1989 | McNeil et al. |
| 4,832,797 A | 5/1989 | Vadgama et al. |
| 4,835,372 A | 5/1989 | Gombrich et al. |
| RE32,947 E | 6/1989 | Dormer et al. |
| 4,837,049 A | 6/1989 | Byers et al. |
| 4,840,893 A | 6/1989 | Hill et al. |
| RE32,974 E | 7/1989 | Porat et al. |

(56) References Cited

U.S. PATENT DOCUMENTS

| | | |
|---|---|---|
| 4,844,076 A | 7/1989 | Lesho et al. |
| 4,845,035 A | 7/1989 | Fanta et al. |
| 4,847,785 A | 7/1989 | Stephens |
| 4,848,351 A | 7/1989 | Finch |
| 4,854,322 A | 8/1989 | Ash et al. |
| 4,856,340 A | 8/1989 | Garrison |
| 4,857,713 A | 8/1989 | Brown |
| 4,858,617 A | 8/1989 | Sanders |
| 4,870,561 A | 9/1989 | Love et al. |
| 4,871,351 A | 10/1989 | Feingold |
| 4,871,440 A | 10/1989 | Nagata et al. |
| 4,874,499 A | 10/1989 | Smith et al. |
| 4,874,500 A | 10/1989 | Madou et al. |
| 4,890,620 A | 1/1990 | Gough |
| 4,890,621 A | 1/1990 | Hakky |
| 4,894,137 A | 1/1990 | Takizawa et al. |
| 4,897,162 A | 1/1990 | Lewandowski et al. |
| 4,897,173 A | 1/1990 | Nankai et al. |
| 4,899,839 A | 2/1990 | Dessertine et al. |
| 4,909,908 A | 3/1990 | Ross et al. |
| 4,911,794 A | 3/1990 | Parce et al. |
| 4,917,800 A | 4/1990 | Lonsdale et al. |
| 4,919,141 A | 4/1990 | Zier et al. |
| 4,919,767 A | 4/1990 | Vadgama et al. |
| 4,920,969 A | 5/1990 | Suzuki |
| 4,920,977 A | 5/1990 | Haynes |
| 4,923,586 A | 5/1990 | Katayama et al. |
| 4,925,268 A | 5/1990 | Iyer et al. |
| 4,927,516 A | 5/1990 | Yamaguchi et al. |
| 4,931,795 A | 6/1990 | Gord |
| 4,934,369 A | 6/1990 | Maxwell |
| 4,935,105 A | 6/1990 | Churchouse |
| 4,935,345 A | 6/1990 | Guibeau et al. |
| 4,936,956 A | 6/1990 | Wrighton |
| 4,938,860 A | 7/1990 | Wogoman |
| 4,942,127 A | 7/1990 | Wada et al. |
| 4,944,299 A | 7/1990 | Silvian |
| 4,945,045 A | 7/1990 | Forrest et al. |
| 4,950,378 A | 8/1990 | Nagara |
| 4,953,552 A | 9/1990 | DeMarzo |
| 4,954,129 A | 9/1990 | Giuliani et al. |
| 4,957,115 A | 9/1990 | Selker |
| 4,958,632 A | 9/1990 | Duggan |
| 4,968,400 A | 11/1990 | Shimomura et al. |
| 4,969,468 A | 11/1990 | Byers et al. |
| 4,970,145 A | 11/1990 | Bennetto et al. |
| 4,974,929 A | 12/1990 | Curry |
| 4,979,509 A | 12/1990 | Hakky |
| 4,986,271 A | 1/1991 | Wilkins |
| 4,990,845 A | 2/1991 | Gord |
| 4,991,582 A | 2/1991 | Byers et al. |
| 4,994,068 A | 2/1991 | Hufnagie |
| 4,994,167 A | 2/1991 | Shults et al. |
| 4,995,402 A | 2/1991 | Smith et al. |
| 5,000,180 A | 3/1991 | Kuypers et al. |
| 5,001,054 A | 3/1991 | Wagner |
| 5,002,054 A | 3/1991 | Ash et al. |
| 5,007,427 A | 4/1991 | Suzuki et al. |
| 5,016,172 A | 5/1991 | Dessertine |
| 5,016,201 A | 5/1991 | Bryan et al. |
| 5,019,974 A | 5/1991 | Beckers |
| 5,034,192 A | 7/1991 | Wrighton et al. |
| 5,035,860 A | 7/1991 | Kleingeld et al. |
| 5,036,860 A | 8/1991 | Leigh et al. |
| 5,036,861 A | 8/1991 | Sembrowich et al. |
| 5,037,527 A | 8/1991 | Hayashi et al. |
| 5,049,487 A | 9/1991 | Phillips et al. |
| 5,050,612 A | 9/1991 | Matsumura |
| 5,055,171 A | 10/1991 | Peck |
| 5,058,592 A | 10/1991 | Whisler |
| 5,063,081 A | 11/1991 | Cozzette et al. |
| 5,068,536 A | 11/1991 | Rosenthal |
| 5,070,535 A | 12/1991 | Hochmair et al. |
| 5,073,500 A | 12/1991 | Saito et al. |
| 5,077,476 A | 12/1991 | Rosenthal |
| 5,078,854 A | 1/1992 | Burgess et al. |
| 5,082,550 A | 1/1992 | Rishpon et al. |
| 5,082,786 A | 1/1992 | Nakamoto |
| 5,084,828 A | 1/1992 | Kaufman et al. |
| 5,089,112 A | 2/1992 | Skotheim et al. |
| 5,094,951 A | 3/1992 | Rosenberg |
| 5,095,904 A | 3/1992 | Seligman et al. |
| 5,096,560 A | 3/1992 | Takai et al. |
| 5,096,836 A | 3/1992 | Macho et al. |
| 5,097,834 A | 3/1992 | Skrabal |
| 5,101,814 A | 4/1992 | Palti |
| 5,106,365 A | 4/1992 | Hernandez |
| 5,108,564 A | 4/1992 | Szuminsky et al. |
| 5,109,850 A | 5/1992 | Blanco et al. |
| 5,111,539 A | 5/1992 | Hiruta et al. |
| 5,111,818 A | 5/1992 | Suzuji et al. |
| 5,114,678 A | 5/1992 | Crawford et al. |
| 5,120,420 A | 6/1992 | Nankai et al. |
| 5,120,421 A | 6/1992 | Glass et al. |
| 5,122,925 A | 6/1992 | Inpyn |
| 5,126,034 A | 6/1992 | Carter et al. |
| 5,126,247 A | 6/1992 | Palmer et al. |
| 5,130,009 A | 7/1992 | Marsoner et al. |
| 5,133,856 A | 7/1992 | Yamaguchi et al. |
| 5,134,391 A | 7/1992 | Okada |
| 5,135,003 A | 8/1992 | Souma |
| 5,139,023 A | 8/1992 | Stanley et al. |
| 5,140,393 A | 8/1992 | Hijikihigawa et al. |
| 5,141,868 A | 8/1992 | Shanks et al. |
| 5,161,532 A | 11/1992 | Joseph |
| 5,165,407 A | 11/1992 | Wilson et al. |
| 5,168,046 A | 12/1992 | Hamamoto et al. |
| 5,174,291 A | 12/1992 | Schoonen et al. |
| 5,176,644 A | 1/1993 | Srisathapat et al. |
| 5,176,662 A | 1/1993 | Bartholomew et al. |
| 5,182,707 A | 1/1993 | Cooper et al. |
| 5,184,359 A | 2/1993 | Tsukamura et al. |
| 5,185,256 A | 2/1993 | Nankai et al. |
| 5,190,041 A | 3/1993 | Palti |
| 5,192,415 A | 3/1993 | Yoshioka et al. |
| 5,192,416 A | 3/1993 | Wang et al. |
| 5,193,539 A | 3/1993 | Schulman et al. |
| 5,193,540 A | 3/1993 | Schulman et al. |
| 5,197,322 A | 3/1993 | Indravudh |
| 5,198,367 A | 3/1993 | Aizawa et al. |
| 5,200,051 A | 4/1993 | Cozzette et al. |
| 5,202,261 A | 4/1993 | Musho et al. |
| 5,205,920 A | 4/1993 | Oyama et al. |
| 5,206,145 A | 4/1993 | Cattell |
| 5,208,154 A | 5/1993 | Weaver et al. |
| 5,209,229 A | 5/1993 | Gilli |
| 5,215,887 A | 6/1993 | Saito |
| 5,216,597 A | 6/1993 | Beckers |
| 5,217,442 A | 6/1993 | Davis |
| 5,217,595 A | 6/1993 | Smith et al. |
| 5,227,042 A | 7/1993 | Zawodzinski et al. |
| 5,229,282 A | 7/1993 | Yoshioka et al. |
| 5,231,988 A | 8/1993 | Wernicke et al. |
| 5,236,143 A | 8/1993 | Dragon |
| 5,237,993 A | 8/1993 | Skrabal |
| 5,246,867 A | 9/1993 | Lakowicz et al. |
| 5,250,439 A | 10/1993 | Musho et al. |
| 5,251,126 A | 10/1993 | Kahn et al. |
| 5,257,971 A | 11/1993 | Lord et al. |
| 5,257,980 A | 11/1993 | Van Antwerp et al. |
| 5,261,401 A | 11/1993 | Baker et al. |
| 5,262,035 A | 11/1993 | Gregg et al. |
| 5,262,305 A | 11/1993 | Heller et al. |
| 5,264,103 A | 11/1993 | Yoshioka et al. |
| 5,264,104 A | 11/1993 | Gregg et al. |
| 5,264,105 A | 11/1993 | Gregg et al. |
| 5,264,106 A | 11/1993 | McAleer et al. |
| 5,265,888 A | 11/1993 | Yamamoto et al. |
| 5,266,179 A | 11/1993 | Nankai et al. |
| 5,269,212 A | 12/1993 | Peters et al. |
| 5,271,815 A | 12/1993 | Wong |
| 5,272,060 A | 12/1993 | Hamamoto et al. |
| 5,275,159 A | 1/1994 | Griebel |
| 5,278,079 A | 1/1994 | Gubinski et al. |

(56) References Cited

U.S. PATENT DOCUMENTS

| | | |
|---|---|---|
| 5,279,294 A | 1/1994 | Anderson |
| 5,282,950 A | 2/1994 | Dietze et al. |
| 5,284,156 A | 2/1994 | Schramm et al. |
| 5,285,792 A | 2/1994 | Sjoquist et al. |
| 5,286,362 A | 2/1994 | Hoenes et al. |
| 5,286,364 A | 2/1994 | Yacynych et al. |
| 5,288,636 A | 2/1994 | Pollmann et al. |
| 5,291,887 A | 3/1994 | Stanley et al. |
| 5,293,546 A | 3/1994 | Tadros et al. |
| 5,293,877 A | 3/1994 | O'Hara et al. |
| 5,299,571 A | 4/1994 | Mastrototaro |
| 5,304,468 A | 4/1994 | Phillips et al. |
| 5,307,263 A | 4/1994 | Brown |
| 5,309,919 A | 5/1994 | Snell et al. |
| 5,310,885 A | 5/1994 | Maier et al. |
| 5,320,098 A | 6/1994 | Davidson |
| 5,320,725 A | 6/1994 | Gregg et al. |
| 5,322,063 A | 6/1994 | Allen et al. |
| 5,324,303 A | 6/1994 | Strong et al. |
| 5,324,316 A | 6/1994 | Schulman et al. |
| 5,326,449 A | 7/1994 | Cunningham |
| 5,337,258 A | 8/1994 | Dennis |
| 5,337,747 A | 8/1994 | Neftei |
| 5,340,722 A | 8/1994 | Wolfbeis et al. |
| 5,342,789 A | 8/1994 | Chick et al. |
| 5,352,348 A | 10/1994 | Young et al. |
| 5,356,348 A | 10/1994 | Bellio et al. |
| 5,356,786 A | 10/1994 | Heller et al. |
| 5,358,514 A | 10/1994 | Schulman et al. |
| 5,360,404 A | 11/1994 | Novacek et al. |
| 5,364,797 A | 11/1994 | Olson et al. |
| 5,366,609 A | 11/1994 | White et al. |
| 5,368,028 A | 11/1994 | Palti |
| 5,370,622 A | 12/1994 | Livingston et al. |
| 5,371,687 A | 12/1994 | Holmes, II et al. |
| 5,372,133 A | 12/1994 | Hogen Esch |
| 5,372,427 A | 12/1994 | Padovani et al. |
| 5,376,070 A | 12/1994 | Purvis et al. |
| 5,376,251 A | 12/1994 | Kaneko et al. |
| 5,377,258 A | 12/1994 | Bro |
| 5,378,628 A | 1/1995 | Gratzel et al. |
| 5,379,238 A | 1/1995 | Stark |
| 5,380,422 A | 1/1995 | Negishis et al. |
| 5,382,346 A | 1/1995 | Uenoyama et al. |
| 5,384,547 A | 1/1995 | Lynk et al. |
| 5,387,327 A | 2/1995 | Khan |
| 5,390,671 A | 2/1995 | Lord et al. |
| 5,391,250 A | 2/1995 | Cheney, II et al. |
| 5,393,903 A | 2/1995 | Gratzel et al. |
| 5,395,504 A | 3/1995 | Saurer et al. |
| 5,399,823 A | 3/1995 | McCusker |
| 5,400,782 A | 3/1995 | Beaubiah |
| 5,408,999 A | 4/1995 | Singh et al. |
| 5,410,471 A | 4/1995 | Alyfuku et al. |
| 5,410,474 A | 4/1995 | Fox |
| 5,411,647 A | 5/1995 | Johnson et al. |
| 5,413,690 A | 5/1995 | Kost et al. |
| 5,422,246 A | 6/1995 | Koopal et al. |
| 5,429,602 A | 7/1995 | Hauser |
| 5,431,160 A | 7/1995 | Wilkins |
| 5,431,691 A | 7/1995 | Snell et al. |
| 5,431,921 A | 7/1995 | Thombre |
| 5,433,710 A | 7/1995 | Van Antwerp et al. |
| 5,437,973 A | 8/1995 | Vadgama et al. |
| 5,437,999 A | 8/1995 | Dieboid et al. |
| 5,445,611 A | 8/1995 | Eppstein et al. |
| 5,445,920 A | 8/1995 | Saito |
| 5,456,692 A | 10/1995 | Smith, Jr. et al. |
| 5,456,940 A | 10/1995 | Funderburk |
| 5,458,140 A | 10/1995 | Eppstein et al. |
| 5,460,618 A | 10/1995 | Harreld |
| 5,462,525 A | 10/1995 | Srisathapat et al. |
| 5,462,645 A | 10/1995 | Albery et al. |
| 5,466,218 A | 11/1995 | Srisathapat et al. |
| 5,469,846 A | 11/1995 | Khan |
| 5,472,317 A | 12/1995 | Field et al. |
| 5,476,460 A | 12/1995 | Montalvo |
| 5,477,855 A | 12/1995 | Schindler et al. |
| 5,482,473 A | 1/1996 | Lord et al. |
| 5,484,404 A | 1/1996 | Schulman et al. |
| 5,487,751 A | 1/1996 | Radons et al. |
| 5,489,414 A | 2/1996 | Schreiber et al. |
| 5,491,474 A | 2/1996 | Suni et al. |
| 5,494,562 A | 2/1996 | Maley et al. |
| 5,496,453 A | 3/1996 | Uenoyama et al. |
| 5,497,772 A | 3/1996 | Schulman et al. |
| 5,501,956 A | 3/1996 | Wada et al. |
| 5,505,709 A | 4/1996 | Funderburk |
| 5,505,713 A | 4/1996 | Van Antwerp et al. |
| 5,507,288 A | 4/1996 | Bocker et al. |
| 5,508,171 A | 4/1996 | Walling et al. |
| 5,509,410 A | 4/1996 | Hill et al. |
| 5,514,103 A | 5/1996 | Srisathapat et al. |
| 5,514,253 A | 5/1996 | Davis et al. |
| 5,514,718 A | 5/1996 | Lewis et al. |
| 5,518,006 A | 5/1996 | Mawhirt et al. |
| 5,520,787 A | 5/1996 | Hanagan et al. |
| 5,522,865 A | 6/1996 | Schulman et al. |
| 5,525,511 A | 6/1996 | D'Costa |
| 5,526,120 A | 6/1996 | Jina et al. |
| 5,527,307 A | 6/1996 | Srisathapat et al. |
| 5,529,676 A | 6/1996 | Maley et al. |
| 5,531,878 A | 7/1996 | Vadgama et al. |
| 5,538,511 A | 7/1996 | Van Antwerp et al. |
| 5,545,152 A | 8/1996 | Funderburk et al. |
| 5,545,191 A | 8/1996 | Mann et al. |
| 5,549,113 A | 8/1996 | Halleck et al. |
| 5,549,115 A | 8/1996 | Morgan et al. |
| 5,552,027 A | 9/1996 | Birkle et al. |
| 5,552,997 A | 9/1996 | Massart |
| 5,554,166 A | 9/1996 | Lange et al. |
| 5,556,524 A | 9/1996 | Albers |
| 5,560,357 A | 10/1996 | Faupei et al. |
| 5,562,713 A | 10/1996 | Silvian |
| 5,565,085 A | 10/1996 | Ikeda et al. |
| 5,567,302 A | 10/1996 | Song et al. |
| 5,568,400 A | 10/1996 | Stark et al. |
| 5,568,806 A | 10/1996 | Cheney, II et al. |
| 5,569,186 A | 10/1996 | Lord et al. |
| 5,569,212 A | 10/1996 | Brown |
| 5,573,647 A | 11/1996 | Maley et al. |
| 5,575,895 A | 11/1996 | Ikeda et al. |
| 5,580,527 A | 12/1996 | Bell et al. |
| 5,580,794 A | 12/1996 | Allen |
| 5,582,184 A | 12/1996 | Erickson et al. |
| 5,582,697 A | 12/1996 | Ikeda et al. |
| 5,582,698 A | 12/1996 | Flaherty et al. |
| 5,584,813 A | 12/1996 | Livingston et al. |
| 5,586,553 A | 12/1996 | Halli et al. |
| 5,589,326 A | 12/1996 | Deng et al. |
| 5,593,852 A | 1/1997 | Heller et al. |
| 5,594,906 A | 1/1997 | Holmes, II et al. |
| 5,596,150 A | 1/1997 | Arndy et al. |
| 5,596,994 A | 1/1997 | Bro |
| 5,601,435 A | 2/1997 | Quy |
| 5,601,694 A | 2/1997 | Maley et al. |
| 5,605,152 A | 2/1997 | Slate et al. |
| 5,609,575 A | 3/1997 | Larson et al. |
| 5,611,900 A | 3/1997 | Worden et al. |
| 5,615,671 A | 4/1997 | Schoonen et al. |
| 5,616,222 A | 4/1997 | Maley et al. |
| 5,617,851 A | 4/1997 | Lipkovker |
| 5,623,925 A | 4/1997 | Swenson et al. |
| 5,628,309 A | 5/1997 | Brown |
| 5,628,310 A | 5/1997 | Rao et al. |
| 5,628,890 A | 5/1997 | Carter et al. |
| 5,629,981 A | 5/1997 | Nerlikar |
| 5,637,095 A | 6/1997 | Nason et al. |
| 5,640,764 A | 6/1997 | Strojnik |
| 5,640,954 A | 6/1997 | Pfeiffer et al. |
| 5,643,212 A | 7/1997 | Coutre et al. |
| 5,647,853 A | 7/1997 | Feldmann et al. |
| 5,650,062 A | 7/1997 | Ikeda et al. |
| 5,651,767 A | 7/1997 | Schulman et al. |

(56) References Cited

U.S. PATENT DOCUMENTS

| | | |
|---|---|---|
| 5,651,869 A | 7/1997 | Yoshioka et al. |
| 5,653,239 A | 8/1997 | Pompei et al. |
| 5,660,163 A | 8/1997 | Schulman et al. |
| 5,665,065 A | 9/1997 | Colman et al. |
| 5,665,222 A | 9/1997 | Heller et al. |
| 5,667,983 A | 9/1997 | Abel et al. |
| 5,670,031 A | 9/1997 | Hintsche et al. |
| 5,678,571 A | 10/1997 | Brown |
| 5,679,690 A | 10/1997 | Andre et al. |
| 5,680,858 A | 10/1997 | Hansen et al. |
| 5,682,233 A | 10/1997 | Brinda |
| 5,686,717 A | 11/1997 | Knowles et al. |
| 5,695,623 A | 12/1997 | Michel et al. |
| 5,695,949 A | 12/1997 | Galen et al. |
| 5,701,894 A | 12/1997 | Cherry et al. |
| 5,704,922 A | 1/1998 | Brown |
| 5,707,502 A | 1/1998 | McCaffrey et al. |
| 5,708,247 A | 1/1998 | McAleer et al. |
| 5,710,630 A | 1/1998 | Essenpreis et al. |
| 5,711,001 A | 1/1998 | Bussan et al. |
| 5,711,297 A | 1/1998 | Iliff et al. |
| 5,711,861 A | 1/1998 | Ward et al. |
| 5,711,862 A | 1/1998 | Sakoda et al. |
| 5,711,868 A | 1/1998 | Maley et al. |
| 5,718,234 A | 2/1998 | Warden et al. |
| 5,720,733 A | 2/1998 | Brown |
| 5,720,862 A | 2/1998 | Hamamoto et al. |
| 5,721,783 A | 2/1998 | Anderson |
| 5,722,397 A | 3/1998 | Eppstein |
| 5,726,646 A | 3/1998 | Bane et al. |
| 5,727,548 A | 3/1998 | Hill et al. |
| 5,730,124 A | 3/1998 | Yamauchi |
| 5,730,654 A | 3/1998 | Brown |
| 5,735,273 A | 4/1998 | Kurnik et al. |
| 5,735,285 A | 4/1998 | Albert et al. |
| 5,740,431 A | 4/1998 | Rail |
| 5,741,211 A | 4/1998 | Renirie et al. |
| 5,741,688 A | 4/1998 | Oxenboll et al. |
| 5,746,217 A | 5/1998 | Erickson et al. |
| 5,748,103 A | 5/1998 | Flach et al. |
| 5,750,926 A | 5/1998 | Schulman et al. |
| 5,768,591 A | 6/1998 | Robinson |
| 5,770,028 A | 6/1998 | Maley et al. |
| 5,771,001 A | 6/1998 | Cobb |
| 5,771,890 A | 6/1998 | Tamada |
| 5,772,586 A | 6/1998 | Heinonen et al. |
| 5,777,060 A | 7/1998 | Van Antwerp |
| 5,779,665 A | 7/1998 | Mastrototaro et al. |
| 5,782,814 A | 7/1998 | Brown et al. |
| 5,785,681 A | 7/1998 | Indravudh |
| 5,786,439 A | 7/1998 | Van Antwerp et al. |
| 5,786,584 A | 7/1998 | Button et al. |
| 5,788,678 A | 8/1998 | Van Antwerp |
| 5,791,344 A | 8/1998 | Schulman et al. |
| 5,792,117 A | 8/1998 | Brown |
| 5,800,420 A | 9/1998 | Gross et al. |
| 5,804,048 A | 9/1998 | Wong et al. |
| 5,807,315 A | 9/1998 | Van Antwerp et al. |
| 5,807,375 A | 9/1998 | Gross et al. |
| 5,814,599 A | 9/1998 | Mitragotri et al. |
| 5,820,551 A | 10/1998 | Hill et al. |
| 5,820,570 A | 10/1998 | Erickson et al. |
| 5,820,622 A | 10/1998 | Gross et al. |
| 5,822,715 A | 10/1998 | Worthington et al. |
| 5,825,488 A | 10/1998 | Kohl et al. |
| 5,827,179 A | 10/1998 | Lichter et al. |
| 5,827,183 A | 10/1998 | Kurnik et al. |
| 5,827,184 A | 10/1998 | Netherly et al. |
| 5,828,943 A | 10/1998 | Brown |
| 5,830,341 A | 11/1998 | Gilmartin |
| 5,832,448 A | 11/1998 | Brown |
| 5,834,224 A | 11/1998 | Ruger et al. |
| 5,837,454 A | 11/1998 | Cozzette et al. |
| 5,837,546 A | 11/1998 | Allen et al. |
| 5,840,020 A | 11/1998 | Heinonen et al. |
| 5,842,983 A | 12/1998 | Abel et al. |
| 5,843,140 A | 12/1998 | Strojnik |
| 5,846,702 A | 12/1998 | Deng et al. |
| 5,846,744 A | 12/1998 | Athey et al. |
| 5,851,197 A | 12/1998 | Marano et al. |
| 5,854,078 A | 12/1998 | Asher et al. |
| 5,854,189 A | 12/1998 | Kruse et al. |
| 5,857,967 A | 1/1999 | Frid et al. |
| 5,857,983 A | 1/1999 | Douglas et al. |
| 5,860,917 A | 1/1999 | Comanor et al. |
| 5,872,713 A | 2/1999 | Douglas et al. |
| 5,876,484 A | 3/1999 | Raskin et al. |
| 5,879,163 A | 3/1999 | Brown et al. |
| 5,879,311 A | 3/1999 | Duchon et al. |
| 5,880,829 A | 3/1999 | Kauhaniemi et al. |
| 5,882,494 A | 3/1999 | Van Antwerp |
| 5,885,211 A | 3/1999 | Eppstein et al. |
| 5,887,133 A | 3/1999 | Brown et al. |
| 5,897,493 A | 4/1999 | Brown |
| 5,898,025 A | 4/1999 | Burg et al. |
| 5,899,855 A | 5/1999 | Brown |
| 5,913,310 A | 6/1999 | Brown |
| 5,914,026 A | 6/1999 | Blubaugh, Jr. et al. |
| 5,917,346 A | 6/1999 | Gord |
| 5,918,603 A | 7/1999 | Brown |
| 5,925,021 A | 7/1999 | Castellano et al. |
| 5,931,791 A | 8/1999 | Saltzstein et al. |
| 5,933,136 A | 8/1999 | Brown |
| 5,940,801 A | 8/1999 | Brown |
| 5,942,979 A | 8/1999 | Luppino |
| 5,945,345 A | 8/1999 | Blatt et al. |
| 5,947,921 A | 9/1999 | Johnson et al. |
| 5,948,512 A | 9/1999 | Kubota et al. |
| 5,950,632 A | 9/1999 | Reber et al. |
| 5,951,300 A | 9/1999 | Brown |
| 5,951,492 A | 9/1999 | Douglas et al. |
| 5,951,521 A | 9/1999 | Mastrototaro et al. |
| 5,951,836 A | 9/1999 | McAleer et al. |
| 5,954,643 A | 9/1999 | Van Antwerp |
| 5,954,685 A | 9/1999 | Tierny |
| 5,954,700 A | 9/1999 | Kovelman |
| 5,956,501 A | 9/1999 | Brown |
| 5,957,854 A | 9/1999 | Besson et al. |
| 5,957,890 A | 9/1999 | Mann et al. |
| 5,957,958 A | 9/1999 | Schulman et al. |
| 5,960,403 A | 9/1999 | Brown |
| 5,961,451 A | 10/1999 | Reber et al. |
| 5,964,993 A | 10/1999 | Blubaugh, Jr. et al. |
| 5,965,380 A | 10/1999 | Heller et al. |
| 5,968,839 A | 10/1999 | Blatt et al. |
| 5,971,922 A | 10/1999 | Arita et al. |
| 5,971,941 A | 10/1999 | Simons et al. |
| 5,974,124 A | 10/1999 | Schlueter, Jr. et al. |
| 5,977,476 A | 11/1999 | Guha et al. |
| 5,981,294 A | 11/1999 | Blatt et al. |
| 5,989,409 A | 11/1999 | Kurnik et al. |
| 5,994,476 A | 11/1999 | Shin et al. |
| 5,995,860 A | 11/1999 | Sun et al. |
| 5,997,476 A | 12/1999 | Brown |
| 5,999,848 A | 12/1999 | Gord et al. |
| 5,999,849 A | 12/1999 | Gord et al. |
| 6,001,067 A | 12/1999 | Shults et al. |
| 6,002,954 A | 12/1999 | Van Antwerp et al. |
| 6,002,961 A | 12/1999 | Mitragotri et al. |
| 6,004,441 A | 12/1999 | Fujiwara et al. |
| 6,011,984 A | 1/2000 | Van Antwerp et al. |
| 6,014,577 A | 1/2000 | Henning et al. |
| 6,018,678 A | 1/2000 | Mitragotri et al. |
| 6,023,629 A | 2/2000 | Tamada |
| 6,024,699 A | 2/2000 | Surwit et al. |
| 6,026,320 A | 2/2000 | Carlson et al. |
| 6,027,459 A | 2/2000 | Shain et al. |
| 6,027,692 A | 2/2000 | Galen et al. |
| 6,032,059 A | 2/2000 | Henning et al. |
| 6,032,199 A | 2/2000 | Lim et al. |
| 6,033,866 A | 3/2000 | Guo et al. |
| 6,035,237 A | 3/2000 | Schulman et al. |
| 6,040,194 A | 3/2000 | Chick et al. |
| 6,041,253 A | 3/2000 | Kost et al. |

(56) References Cited

U.S. PATENT DOCUMENTS

| | | | |
|---|---|---|---|
| 6,043,437 A | 3/2000 | Schulman et al. |
| 6,049,727 A | 4/2000 | Crothall |
| 6,056,718 A | 5/2000 | Funderburk et al. |
| 6,063,459 A | 5/2000 | Velte |
| 6,066,243 A | 5/2000 | Anderson et al. |
| 6,067,474 A | 5/2000 | Schulman et al. |
| 6,068,615 A | 5/2000 | Brown et al. |
| 6,071,249 A | 6/2000 | Cunningham et al. |
| 6,071,251 A | 6/2000 | Cunningham et al. |
| 6,071,294 A | 6/2000 | Simons et al. |
| 6,071,391 A | 6/2000 | Gotoh et al. |
| 6,073,031 A | 6/2000 | Helstab et al. |
| 6,081,736 A | 6/2000 | Colvin et al. |
| 6,083,710 A | 7/2000 | Heller et al. |
| 6,088,608 A | 7/2000 | Schulman et al. |
| 6,091,975 A | 7/2000 | Daddona et al. |
| 6,091,976 A | 7/2000 | Pfeiffer et al. |
| 6,093,156 A | 7/2000 | Cunningham et al. |
| 6,093,167 A | 7/2000 | Houben et al. |
| 6,093,172 A | 7/2000 | Funderburk et al. |
| 6,096,364 A | 8/2000 | Bok et al. |
| 6,097,831 A | 8/2000 | Wieck et al. |
| 6,099,484 A | 8/2000 | Douglas et al. |
| 6,101,478 A | 8/2000 | Brown |
| 6,103,033 A | 8/2000 | Say et al. |
| 6,106,780 A | 8/2000 | Douglas et al. |
| 6,110,148 A | 8/2000 | Brown et al. |
| 6,110,152 A | 8/2000 | Kovelman |
| 6,113,578 A | 9/2000 | Brown |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,125,978 A | 10/2000 | Ando et al. |
| 6,134,461 A | 10/2000 | Say et al. |
| 6,134,504 A | 10/2000 | Douglas et al. |
| 6,139,718 A | 10/2000 | Kurnik et al. |
| 6,141,573 A | 10/2000 | Kurnik et al. |
| 6,142,939 A | 11/2000 | Eppstein et al. |
| 6,143,164 A | 11/2000 | Heller et al. |
| 6,144,837 A | 11/2000 | Quy |
| 6,144,869 A | 11/2000 | Berner et al. |
| 6,144,922 A | 11/2000 | Douglas et al. |
| 6,148,094 A | 11/2000 | Kinsella |
| 6,150,128 A | 11/2000 | Uretsky |
| 6,151,586 A | 11/2000 | Brown |
| 6,153,062 A | 11/2000 | Saito et al. |
| 6,153,069 A | 11/2000 | Pottgen et al. |
| 6,159,147 A | 12/2000 | Lichter et al. |
| 6,161,095 A | 12/2000 | Brown |
| 6,162,611 A | 12/2000 | Heller et al. |
| 6,162,639 A | 12/2000 | Douglas |
| 6,167,362 A | 12/2000 | Brown et al. |
| 6,168,563 B1 | 1/2001 | Brown |
| 6,170,318 B1 | 1/2001 | Lewis |
| 6,175,752 B1 | 1/2001 | Say et al. |
| 6,180,416 B1 | 1/2001 | Kurnik et al. |
| 6,186,145 B1 | 2/2001 | Brown |
| 6,192,891 B1 | 2/2001 | Gravel et al. |
| 6,193,873 B1 | 2/2001 | Ohara et al. |
| 6,196,970 B1 | 3/2001 | Brown |
| 6,198,957 B1 | 3/2001 | Green |
| 6,200,265 B1 | 3/2001 | Walsh et al. |
| 6,201,979 B1 | 3/2001 | Kurnik et al. |
| 6,201,980 B1 | 3/2001 | Darrow et al. |
| 6,206,841 B1 | 3/2001 | Cunningham et al. |
| 6,207,400 B1 | 3/2001 | Kwon |
| 6,208,894 B1 | 3/2001 | Schulman et al. |
| 6,210,272 B1 | 4/2001 | Brown |
| 6,210,976 B1 | 4/2001 | Sabbadini |
| 6,212,416 B1 | 4/2001 | Ward et al. |
| 6,219,565 B1 | 4/2001 | Cupp et al. |
| 6,219,574 B1 | 4/2001 | Cormier et al. |
| 6,224,745 B1 | 5/2001 | Baltruschat |
| 6,232,130 B1 | 5/2001 | Wolf |
| 6,232,370 B1 | 5/2001 | Kubota et al. |
| 6,233,471 B1 | 5/2001 | Berner et al. |
| 6,233,539 B1 | 5/2001 | Brown |
| 6,239,925 B1 | 5/2001 | Ardrey et al. |
| 6,241,862 B1 | 6/2001 | McAleer et al. |
| 6,246,330 B1 | 6/2001 | Nielsen |
| 6,246,992 B1 | 6/2001 | Brown |
| 6,248,065 B1 | 6/2001 | Brown |
| 6,248,067 B1 | 6/2001 | Causey, III et al. |
| 6,248,093 B1 | 6/2001 | Moberg |
| 6,251,260 B1 | 6/2001 | Heller et al. |
| 6,252,032 B1 | 6/2001 | Van Antwerp et al. |
| 6,253,804 B1 | 7/2001 | Safabash |
| 6,254,586 B1 | 7/2001 | Mann et al. |
| 6,256,643 B1 | 7/2001 | Cork et al. |
| 6,259,587 B1 | 7/2001 | Sheldon et al. |
| 6,259,937 B1 | 7/2001 | Schulman et al. |
| 6,260,022 B1 | 7/2001 | Brown |
| 6,266,645 B1 | 7/2001 | Simpson |
| 6,267,724 B1 | 7/2001 | Taylor |
| 6,268,161 B1 | 7/2001 | Han et al. |
| 6,270,445 B1 | 8/2001 | Dean, Jr. et al. |
| 6,270,455 B1 | 8/2001 | Brown |
| 6,272,364 B1 | 8/2001 | Kurnik |
| 6,275,717 B1 | 8/2001 | Gross et al. |
| 6,280,416 B1 | 8/2001 | Van Antwerp et al. |
| 6,280,587 B1 | 8/2001 | Matsumoto |
| 6,281,006 B1 | 8/2001 | Heller et al. |
| 6,283,761 B1 | 9/2001 | Joao |
| 6,283,943 B1 | 9/2001 | Dy et al. |
| 6,284,126 B1 | 9/2001 | Kurnik et al. |
| 6,284,478 B1 | 9/2001 | Heller et al. |
| 6,293,925 B1 | 9/2001 | Safabash et al. |
| 6,294,281 B1 | 9/2001 | Heller |
| 6,295,463 B1 | 9/2001 | Stenzler |
| 6,295,506 B1 | 9/2001 | Heinonen et al. |
| 6,298,254 B2 | 10/2001 | Tamada |
| 6,299,578 B1 | 10/2001 | Kurnik et al. |
| 6,299,757 B1 | 10/2001 | Feldman et al. |
| 6,301,499 B1 | 10/2001 | Carlson et al. |
| 6,304,766 B1 | 10/2001 | Colvin, Jr. et al. |
| 6,306,104 B1 | 10/2001 | Cunningham et al. |
| 6,309,351 B1 | 10/2001 | Kurnik et al. |
| 6,309,884 B1 | 10/2001 | Cooper et al. |
| 6,314,317 B1 | 11/2001 | Willis |
| 6,315,721 B2 | 11/2001 | Schulman et al. |
| 6,319,540 B1 | 11/2001 | Van Antwerp et al. |
| 6,326,160 B1 | 12/2001 | Dunn et al. |
| 6,329,161 B1 | 12/2001 | Heller et al. |
| 6,329,929 B1 | 12/2001 | Weijand et al. |
| 6,330,426 B2 | 12/2001 | Brown et al. |
| 6,330,464 B1 | 12/2001 | Colvin, Jr. et al. |
| 6,331,518 B2 | 12/2001 | Hemm et al. |
| 6,334,778 B1 | 1/2002 | Brown |
| 6,336,900 B1 | 1/2002 | Alleckson et al. |
| 6,338,790 B1 | 1/2002 | Feldman et al. |
| 6,340,421 B1 | 1/2002 | Vachon et al. |
| 6,341,232 B1 | 1/2002 | Conn et al. |
| 6,348,640 B1 | 2/2002 | Navot et al. |
| 6,356,776 B1 | 3/2002 | Berner et al. |
| 6,359,444 B1 | 3/2002 | Grimes |
| 6,360,888 B1 | 3/2002 | McIvor et al. |
| 6,366,793 B1 | 4/2002 | Bell et al. |
| 6,366,794 B1 | 4/2002 | Moussy et al. |
| 6,368,141 B1 | 4/2002 | Van Antwerp et al. |
| 6,368,274 B1 | 4/2002 | Van Antwerp et al. |
| 6,370,410 B2 | 4/2002 | Kurnik et al. |
| 6,377,828 B1 | 4/2002 | Chaiken et al. |
| 6,379,301 B1 | 4/2002 | Worthington et al. |
| 6,383,767 B1 | 5/2002 | Polak |
| 6,387,048 B1 | 5/2002 | Schulman et al. |
| 6,391,643 B1 | 5/2002 | Chen et al. |
| 6,393,318 B1 | 5/2002 | Chen et al. |
| 6,398,562 B1 | 6/2002 | Butler et al. |
| 6,405,066 B1 | 6/2002 | Essenpreis et al. |
| 6,413,393 B1 | 7/2002 | Van Antwerp et al. |
| 6,418,332 B1 | 7/2002 | Mastrototaro et al. |

(56) References Cited

U.S. PATENT DOCUMENTS

| | | |
|---|---|---|
| 6,424,847 B1 | 7/2002 | Mastrototaro et al. |
| 6,427,088 B1 | 7/2002 | Bowman, IV et al. |
| 6,434,409 B1 | 8/2002 | Pfeiffer et al. |
| 6,438,414 B1 | 8/2002 | Conn et al. |
| 6,440,068 B1 | 8/2002 | Brown et al. |
| 6,442,637 B1 | 8/2002 | Hawkins et al. |
| 6,443,942 B2 | 9/2002 | Van Antwerp et al. |
| 6,454,710 B1 | 9/2002 | Ballerstadt et al. |
| 6,462,162 B2 | 10/2002 | Van Antwerp et al. |
| 6,464,848 B1 | 10/2002 | Matsumoto |
| 6,466,810 B1 | 10/2002 | Ward et al. |
| 6,468,222 B1 | 10/2002 | Mault et al. |
| 6,471,689 B1 | 10/2002 | Joseph et al. |
| 6,472,122 B1 | 10/2002 | Schulman et al. |
| 6,475,750 B1 | 11/2002 | Han et al. |
| 6,477,395 B2 | 11/2002 | Schulman et al. |
| 6,478,736 B1 | 11/2002 | Mault |
| 6,480,730 B2 | 11/2002 | Darrow et al. |
| 6,482,156 B2 | 11/2002 | Iliff |
| 6,482,158 B2 | 11/2002 | Mault |
| 6,482,604 B2 | 11/2002 | Kwon |
| 6,484,045 B1 | 11/2002 | Holker et al. |
| 6,484,046 B1 | 11/2002 | Say et al. |
| 6,485,138 B1 | 11/2002 | Kubota et al. |
| 6,494,830 B1 | 12/2002 | Wessel |
| 6,496,728 B2 | 12/2002 | Li et al. |
| 6,501,983 B1 | 12/2002 | Natarajan et al. |
| 6,505,059 B1 | 1/2003 | Kollias et al. |
| 6,512,939 B1 | 1/2003 | Colvin et al. |
| 6,513,532 B2 | 2/2003 | Mault et al. |
| 6,514,718 B2 | 2/2003 | Heller et al. |
| 6,515,593 B1 | 2/2003 | Stark et al. |
| 6,520,326 B2 | 2/2003 | McIvor et al. |
| 6,529,755 B2 | 3/2003 | Kurnik et al. |
| 6,529,772 B2 | 3/2003 | Carlson et al. |
| 6,530,915 B2 | 3/2003 | Eppstein et al. |
| 6,534,322 B1 | 3/2003 | Sabbadini |
| 6,534,323 B1 | 3/2003 | Sabbadini |
| 6,535,753 B1 | 3/2003 | Raskas |
| 6,537,243 B1 | 3/2003 | Henning et al. |
| 6,540,675 B2 | 4/2003 | Aceti et al. |
| 6,544,212 B2 | 4/2003 | Galley et al. |
| 6,546,269 B1 | 4/2003 | Kurnik |
| 6,549,796 B2 | 4/2003 | Sohrab |
| 6,551,276 B1 | 4/2003 | Mann et al. |
| 6,551,494 B1 | 4/2003 | Heller et al. |
| 6,553,244 B2 | 4/2003 | Lesho et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,571,200 B1 | 5/2003 | Mault |
| 6,572,542 B1 | 6/2003 | Houben et al. |
| 6,572,545 B2 | 6/2003 | Knobbe et al. |
| 6,574,490 B2 | 6/2003 | Abbink et al. |
| 6,576,101 B1 | 6/2003 | Heller et al. |
| 6,576,117 B1 | 6/2003 | Iketaki et al. |
| 6,577,899 B2 | 6/2003 | Lebel et al. |
| 6,579,498 B1 | 6/2003 | Eglise |
| 6,579,690 B1 | 6/2003 | Bonnecaze et al. |
| 6,584,335 B1 | 6/2003 | Haar et al. |
| 6,585,644 B2 | 7/2003 | Lebel et al. |
| 6,587,705 B1 | 7/2003 | Kim et al. |
| 6,587,995 B1 | 7/2003 | Duboc et al. |
| 6,591,125 B1 | 7/2003 | Buse et al. |
| 6,591,126 B2 | 7/2003 | Roeper et al. |
| 6,594,514 B2 | 7/2003 | Berner et al. |
| 6,595,919 B2 | 7/2003 | Berner et al. |
| 6,595,929 B2 | 7/2003 | Stivoric et al. |
| 6,600,997 B2 | 7/2003 | Deweese et al. |
| 6,602,678 B2 | 8/2003 | Kwon et al. |
| 6,602,909 B1 | 8/2003 | Jarowski |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,612,306 B1 | 9/2003 | Mault |
| 6,615,078 B1 | 9/2003 | Burson et al. |
| 6,618,603 B2 | 9/2003 | Varalli et al. |
| 6,620,106 B2 | 9/2003 | Mault |
| 6,622,045 B2 | 9/2003 | Snell et al. |
| 6,627,058 B1 | 9/2003 | Chan |
| 6,629,934 B2 | 10/2003 | Mault et al. |
| 6,633,772 B2 | 10/2003 | Ford et al. |
| 6,635,014 B2 | 10/2003 | Starkweather et al. |
| 6,641,533 B2 | 11/2003 | Causey, III et al. |
| 6,642,015 B2 | 11/2003 | Vachon et al. |
| 6,645,142 B2 | 11/2003 | Braig et al. |
| 6,648,821 B2 | 11/2003 | Lebel et al. |
| 6,653,091 B1 | 11/2003 | Dunn et al. |
| 6,654,625 B1 | 11/2003 | Say et al. |
| 6,656,114 B1 * | 12/2003 | Poulsen et al. ................. 600/300 |
| 6,658,396 B1 | 12/2003 | Tang et al. |
| 6,659,948 B2 | 12/2003 | Lebel et al. |
| 6,668,196 B1 | 12/2003 | Villegas et al. |
| 6,671,554 B2 | 12/2003 | Gibson et al. |
| 6,673,625 B2 | 1/2004 | Satcher, Jr. et al. |
| 6,675,030 B2 * | 1/2004 | Ciurczak et al. ............... 600/316 |
| 6,676,816 B2 | 1/2004 | Mao et al. |
| 6,682,938 B1 | 1/2004 | Satcher, Jr. et al. |
| 6,683,040 B2 | 1/2004 | Bragulla et al. |
| 6,687,522 B2 | 2/2004 | Tamada |
| 6,687,546 B2 | 2/2004 | Lebel et al. |
| 6,689,056 B1 | 2/2004 | Kilcoyne et al. |
| 6,693,069 B2 | 2/2004 | Korber et al. |
| 6,694,158 B2 | 2/2004 | Polak |
| 6,694,191 B2 | 2/2004 | Starkweather et al. |
| 6,695,860 B1 | 2/2004 | Ward et al. |
| 6,702,857 B2 | 3/2004 | Brauker et al. |
| 6,704,587 B1 | 3/2004 | Kumar et al. |
| 6,711,423 B2 | 3/2004 | Colvin, Jr. |
| 6,723,046 B2 | 4/2004 | Lichtenstein et al. |
| 6,728,560 B2 | 4/2004 | Kollias et al. |
| 6,731,976 B2 | 5/2004 | Penn et al. |
| 6,733,446 B2 | 5/2004 | Lebel et al. |
| 6,734,162 B2 | 5/2004 | Van Antwerp et al. |
| 6,736,777 B2 | 5/2004 | Kim et al. |
| 6,736,797 B1 | 5/2004 | Larsen et al. |
| 6,737,401 B2 | 5/2004 | Kim et al. |
| 6,738,654 B2 | 5/2004 | Sohrab |
| 6,740,075 B2 | 5/2004 | Lebel et al. |
| 6,741,163 B1 | 5/2004 | Roberts |
| 6,741,876 B1 | 5/2004 | Scecina et al. |
| 6,741,877 B1 | 5/2004 | Shults et al. |
| 6,744,350 B2 | 6/2004 | Blomquist |
| 6,746,582 B2 | 6/2004 | Heller et al. |
| 6,749,587 B2 | 6/2004 | Flaherty |
| 6,750,311 B1 | 6/2004 | Van Antwerp et al. |
| 6,758,810 B2 | 7/2004 | Lebel et al. |
| 6,766,183 B2 | 7/2004 | Walsh et al. |
| 6,766,201 B2 | 7/2004 | Von Arx et al. |
| 6,768,425 B2 | 7/2004 | Flaherty et al. |
| 6,770,030 B1 | 8/2004 | Schaupp et al. |
| 6,770,729 B2 | 8/2004 | Van Antwerp et al. |
| 6,771,995 B2 | 8/2004 | Kurnik et al. |
| 6,773,563 B2 | 8/2004 | Matsumoto |
| 6,780,297 B2 | 8/2004 | Matsumoto et al. |
| 6,780,871 B2 | 8/2004 | Glick et al. |
| 6,784,274 B2 | 8/2004 | Van Antwerp et al. |
| 6,790,178 B1 | 9/2004 | Mault et al. |
| 6,794,195 B2 | 9/2004 | Colvin, Jr. |
| 6,800,451 B2 | 10/2004 | Daniloff et al. |
| 6,804,544 B2 | 10/2004 | Van Antwerp et al. |
| 6,809,507 B2 | 10/2004 | Morgan et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |

(56) References Cited

U.S. PATENT DOCUMENTS

| | | |
|---|---|---|
| 6,811,659 B2 | 11/2004 | Vachon |
| 6,812,031 B1 | 11/2004 | Carlsson |
| 6,813,519 B2 | 11/2004 | Lebel et al. |
| 6,816,742 B2 | 11/2004 | Kim et al. |
| 6,835,553 B2 | 12/2004 | Han et al. |
| RE38,681 E | 1/2005 | Kurnik et al. |
| 6,840,912 B2 | 1/2005 | Kloepfer et al. |
| 6,844,023 B2 | 1/2005 | Schulman et al. |
| 6,849,237 B2 | 2/2005 | Housefield et al. |
| 6,850,790 B2 | 2/2005 | Berner et al. |
| 6,852,104 B2 | 2/2005 | Blomquist |
| 6,852,500 B1 | 2/2005 | Hoss et al. |
| 6,852,694 B2 | 2/2005 | Van Antwerp et al. |
| 6,853,854 B1 | 2/2005 | Proniewicz et al. |
| 6,856,928 B2 | 2/2005 | Harmon |
| 6,858,403 B2 | 2/2005 | Han et al. |
| 6,862,465 B2 | 3/2005 | Shults et al. |
| 6,862,466 B2 | 3/2005 | Ackerman |
| 6,865,407 B2 | 3/2005 | Kimball et al. |
| 6,872,200 B2 | 3/2005 | Mann et al. |
| 6,873,268 B2 | 3/2005 | Lebel et al. |
| 6,881,551 B2 | 4/2005 | Heller et al. |
| 6,882,940 B2 | 4/2005 | Potts et al. |
| 6,885,883 B2 | 4/2005 | Parris et al. |
| 6,892,085 B2 | 5/2005 | McIvor et al. |
| 6,895,263 B2 | 5/2005 | Shin et al. |
| 6,895,265 B2 | 5/2005 | Silver |
| 6,899,683 B2 | 5/2005 | Mault et al. |
| 6,899,684 B2 | 5/2005 | Mault et al. |
| 6,902,207 B2 | 6/2005 | Lickliter |
| 6,902,905 B2 | 6/2005 | Burson et al. |
| 6,904,301 B2 | 6/2005 | Raskas |
| 6,907,127 B1 | 6/2005 | Kravitz et al. |
| 6,915,147 B2 | 7/2005 | Lebel et al. |
| 6,918,874 B1 | 7/2005 | Hatch et al. |
| 6,922,578 B2 | 7/2005 | Eppstein et al. |
| RE38,775 E | 8/2005 | Kurnik et al. |
| 6,923,763 B1 | 8/2005 | Kovatchev et al. |
| 6,923,764 B2 | 8/2005 | Aceti et al. |
| 6,923,936 B2 | 8/2005 | Swanson et al. |
| 6,927,246 B2 | 8/2005 | Noronha et al. |
| 6,931,327 B2 | 8/2005 | Goode, Jr. et al. |
| 6,936,006 B2 | 8/2005 | Sabra |
| 6,936,029 B2 | 8/2005 | Mann et al. |
| 6,940,590 B2 | 9/2005 | Colvin, Jr. et al. |
| 6,941,163 B2 | 9/2005 | Ford et al. |
| 6,942,518 B2 | 9/2005 | Liamos et al. |
| 6,950,708 B2 | 9/2005 | Bowman, IV et al. |
| 6,952,603 B2 | 10/2005 | Gerber et al. |
| 6,954,673 B2 | 10/2005 | Von Arx et al. |
| 6,955,650 B2 | 10/2005 | Mault et al. |
| 6,957,102 B2 | 10/2005 | Silver et al. |
| 6,957,107 B2 | 10/2005 | Rogers et al. |
| 6,958,705 B2 | 10/2005 | Lebel et al. |
| 6,968,294 B2 | 11/2005 | Gutta et al. |
| 6,968,375 B1 | 11/2005 | Brown |
| 6,971,274 B2 | 12/2005 | Olin |
| 6,974,437 B2 | 12/2005 | Lebel et al. |
| 6,978,182 B2 | 12/2005 | Mazar et al. |
| 6,979,326 B2 | 12/2005 | Mann et al. |
| 6,983,176 B2 | 1/2006 | Gardner et al. |
| 6,990,366 B2 | 1/2006 | Say et al. |
| 6,991,096 B2 | 1/2006 | Gottlieb et al. |
| 6,997,907 B2 | 2/2006 | Safabash et al. |
| 6,997,920 B2 | 2/2006 | Mann et al. |
| 6,998,247 B2 | 2/2006 | Monfre et al. |
| 6,999,810 B2 | 2/2006 | Berner et al. |
| 7,003,336 B2 | 2/2006 | Holker et al. |
| 7,003,340 B2 | 2/2006 | Say et al. |
| 7,003,341 B2 | 2/2006 | Say et al. |
| 7,004,901 B2 | 2/2006 | Fish |
| 7,005,857 B2 | 2/2006 | Stiene et al. |
| 7,011,630 B2 | 3/2006 | Desai et al. |
| 7,015,817 B2 | 3/2006 | Copley et al. |
| 7,016,713 B2 | 3/2006 | Gardner et al. |
| 7,018,366 B2 | 3/2006 | Easter |
| 7,018,568 B2 | 3/2006 | Tierney |
| 7,022,072 B2 | 4/2006 | Fox et al. |
| 7,024,236 B2 | 4/2006 | Ford et al. |
| 7,024,245 B2 | 4/2006 | Lebel et al. |
| 7,025,425 B2 | 4/2006 | Kovatchev et al. |
| 7,025,743 B2 | 4/2006 | Mann et al. |
| 7,029,444 B2 | 4/2006 | Shin et al. |
| 7,039,810 B1 | 5/2006 | Nichols |
| 7,041,068 B2 | 5/2006 | Freeman et al. |
| 7,041,468 B2 | 5/2006 | Drucker et al. |
| 7,043,287 B1 | 5/2006 | Khalil et al. |
| 7,046,153 B2 | 5/2006 | Oja et al. |
| 7,049,277 B2 | 5/2006 | Bagulla et al. |
| 7,052,251 B2 | 5/2006 | Nason et al. |
| 7,052,472 B1 | 5/2006 | Miller et al. |
| 7,052,483 B2 | 5/2006 | Wojcik |
| 7,056,302 B2 | 6/2006 | Douglas |
| 7,074,307 B2 | 7/2006 | Simpson et al. |
| 7,079,977 B2 | 7/2006 | Osorio et al. |
| 7,081,195 B2 | 7/2006 | Simpson et al. |
| 7,092,891 B2 | 8/2006 | Maus et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,123,950 B2 | 10/2006 | Mannheimer |
| 7,133,710 B2 | 11/2006 | Acosta et al. |
| 7,134,999 B2 | 11/2006 | Brauker et al. |
| 7,136,689 B2 | 11/2006 | Shults et al. |
| 7,150,975 B2 | 12/2006 | Tamada et al. |
| 7,155,112 B2 | 12/2006 | Uno et al. |
| 7,163,511 B2 | 1/2007 | Conn et al. |
| 7,167,818 B2 | 1/2007 | Brown |
| 7,171,274 B2 | 1/2007 | Starkweather et al. |
| 7,183,068 B2 | 2/2007 | Burson et al. |
| 7,183,102 B2 | 2/2007 | Monfre et al. |
| 7,189,341 B2 | 3/2007 | Li et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,225,535 B2 | 6/2007 | Feldman et al. |
| 7,226,978 B2 | 6/2007 | Tapsak et al. |
| 7,228,163 B2 | 6/2007 | Ackerman |
| 7,233,817 B2 | 6/2007 | Yen |
| 7,261,691 B1 | 8/2007 | Asomani |
| 7,267,665 B2 | 9/2007 | Steil et al. |
| 7,276,029 B2 | 10/2007 | Goode, Jr. et al. |
| 7,278,983 B2 | 10/2007 | Ireland et al. |
| 7,295,867 B2 | 11/2007 | Berner et al. |
| 7,297,114 B2 | 11/2007 | Gill et al. |
| 7,299,082 B2 | 11/2007 | Feldman et al. |
| 7,310,544 B2 | 12/2007 | Brister et al. |
| 7,317,938 B2 | 1/2008 | Lorenz et al. |
| 7,318,816 B2 | 1/2008 | Bobroff et al. |
| 7,324,850 B2 | 1/2008 | Persen et al. |
| 7,335,294 B2 | 2/2008 | Heller et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,402,153 B2 | 7/2008 | Steil et al. |
| 7,404,796 B2 | 7/2008 | Ginsberg |
| 7,424,318 B2 | 9/2008 | Brister et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,474,992 B2 | 1/2009 | Ariyur |
| 7,494,465 B2 | 2/2009 | Brister et al. |
| 7,497,827 B2 | 3/2009 | Brister et al. |
| 7,499,002 B2 | 3/2009 | Blasko et al. |
| 7,502,644 B2 | 3/2009 | Gill et al. |
| 7,519,408 B2 | 4/2009 | Rasdal et al. |
| 7,524,287 B2 | 4/2009 | Bharmi |
| 7,547,281 B2 | 6/2009 | Hayes et al. |
| 7,569,030 B2 | 8/2009 | Lebel et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |

(56) References Cited

U.S. PATENT DOCUMENTS

| | | |
|---|---|---|
| 7,613,491 B2 | 11/2009 | Boock et al. |
| 7,615,007 B2 | 11/2009 | Shults et al. |
| 7,618,369 B2 | 11/2009 | Hayter et al. |
| 7,630,748 B2 | 12/2009 | Budiman |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,651,845 B2 | 1/2010 | Doyle, III et al. |
| 7,699,775 B2 | 4/2010 | Desai et al. |
| 7,699,964 B2 | 4/2010 | Feldman et al. |
| 7,736,310 B2 | 6/2010 | Taub et al. |
| 7,766,829 B2 | 8/2010 | Sloan et al. |
| 7,771,352 B2 | 8/2010 | Shults et al. |
| 7,774,145 B2 | 8/2010 | Bruaker et al. |
| 7,778,680 B2 | 8/2010 | Goode, Jr. et al. |
| 7,811,231 B2 | 10/2010 | Jin et al. |
| 7,826,981 B2 | 11/2010 | Goode, Jr. et al. |
| 7,889,069 B2 | 2/2011 | Fifolt et al. |
| 7,899,511 B2 | 3/2011 | Shults et al. |
| 7,905,833 B2 | 3/2011 | Brister et al. |
| 7,914,450 B2 | 3/2011 | Goode, Jr. et al. |
| 7,938,797 B2 | 5/2011 | Estes |
| 7,941,200 B2 | 5/2011 | Weinert et al. |
| 7,946,985 B2 | 5/2011 | Mastrototaro et al. |
| 7,972,296 B2 | 7/2011 | Braig et al. |
| 7,974,672 B2 | 7/2011 | Shults et al. |
| 8,010,174 B2 | 8/2011 | Goode et al. |
| 8,010,256 B2 | 8/2011 | Oowada |
| 8,160,900 B2 | 4/2012 | Taub et al. |
| 8,216,138 B1 | 7/2012 | McGarraugh et al. |
| 8,282,549 B2 | 10/2012 | Brauker et al. |
| 8,461,985 B2 | 6/2013 | Fennell et al. |
| 2001/0011224 A1 | 8/2001 | Brown |
| 2001/0016310 A1 | 8/2001 | Brown et al. |
| 2001/0016682 A1 | 8/2001 | Berner et al. |
| 2001/0016683 A1 | 8/2001 | Darrow et al. |
| 2001/0020124 A1 | 9/2001 | Tamada |
| 2001/0029340 A1 | 10/2001 | Mault et al. |
| 2001/0032278 A1 | 10/2001 | Brown et al. |
| 2001/0037060 A1 | 11/2001 | Thompson et al. |
| 2001/0037069 A1 | 11/2001 | Carlson et al. |
| 2001/0039504 A1 | 11/2001 | Linberg et al. |
| 2001/0041830 A1 | 11/2001 | Varalli et al. |
| 2001/0044581 A1 | 11/2001 | Mault |
| 2001/0044588 A1 | 11/2001 | Mault |
| 2001/0047125 A1 | 11/2001 | Quy |
| 2001/0049096 A1 | 12/2001 | Brown |
| 2001/0049470 A1 | 12/2001 | Mault et al. |
| 2002/0002326 A1 | 1/2002 | Causey, III et al. |
| 2002/0002328 A1 | 1/2002 | Tamada |
| 2002/0004640 A1 | 1/2002 | Conn et al. |
| 2002/0010414 A1 | 1/2002 | Coston et al. |
| 2002/0016530 A1 | 2/2002 | Brown |
| 2002/0016719 A1 | 2/2002 | Nemeth et al. |
| 2002/0019022 A1 | 2/2002 | Dunn et al. |
| 2002/0019586 A1 | 2/2002 | Teller et al. |
| 2002/0019748 A1 | 2/2002 | Brown |
| 2002/0026937 A1 | 3/2002 | Mault |
| 2002/0027164 A1 | 3/2002 | Mault et al. |
| 2002/0028995 A1 | 3/2002 | Mault |
| 2002/0040208 A1 | 4/2002 | Flaherty et al. |
| 2002/0042090 A1 | 4/2002 | Heller et al. |
| 2002/0047867 A1 | 4/2002 | Mault et al. |
| 2002/0053637 A1 | 5/2002 | Conn et al. |
| 2002/0062069 A1 | 5/2002 | Mault |
| 2002/0063060 A1 | 5/2002 | Gascoyne et al. |
| 2002/0068858 A1 | 6/2002 | Braig et al. |
| 2002/0068860 A1 | 6/2002 | Clark |
| 2002/0072858 A1 | 6/2002 | Cheng |
| 2002/0077765 A1 | 6/2002 | Mault |
| 2002/0077766 A1 | 6/2002 | Mault |
| 2002/0081559 A1 | 6/2002 | Brown et al. |
| 2002/0083461 A1 | 6/2002 | Hutcheson et al. |
| 2002/0087056 A1 | 7/2002 | Aceti et al. |
| 2002/0091312 A1 | 7/2002 | Berner et al. |
| 2002/0095076 A1 | 7/2002 | Krausman et al. |
| 2002/0103425 A1 | 8/2002 | Mault |
| 2002/0103499 A1 | 8/2002 | Perez et al. |
| 2002/0106709 A1 | 8/2002 | Potts et al. |
| 2002/0107433 A1 | 8/2002 | Mault |
| 2002/0107476 A1 | 8/2002 | Mann et al. |
| 2002/0109600 A1 | 8/2002 | Mault et al. |
| 2002/0119711 A1 | 8/2002 | Van Antwerp et al. |
| 2002/0124017 A1 | 9/2002 | Mault |
| 2002/0128594 A1 | 9/2002 | Das et al. |
| 2002/0130042 A1 | 9/2002 | Moerman et al. |
| 2002/0133378 A1 | 9/2002 | Mault et al. |
| 2002/0147135 A1 | 10/2002 | Schnell |
| 2002/0161286 A1 | 10/2002 | Gerber et al. |
| 2002/0161288 A1 | 10/2002 | Shin et al. |
| 2002/0169635 A1 | 11/2002 | Shillingburg |
| 2002/0177764 A1 | 11/2002 | Sohrab |
| 2003/0023182 A1 | 1/2003 | Mault et al. |
| 2003/0023317 A1 | 1/2003 | Brauker et al. |
| 2003/0023461 A1 | 1/2003 | Quintanilla et al. |
| 2003/0028089 A1 | 2/2003 | Galley et al. |
| 2003/0028120 A1 | 2/2003 | Mault et al. |
| 2003/0032077 A1 | 2/2003 | Itoh et al. |
| 2003/0032867 A1 | 2/2003 | Crothall et al. |
| 2003/0032868 A1 | 2/2003 | Graskov et al. |
| 2003/0032874 A1 | 2/2003 | Rhodes et al. |
| 2003/0036927 A1 | 2/2003 | Bowen |
| 2003/0040683 A1 | 2/2003 | Rule et al. |
| 2003/0042137 A1 | 3/2003 | Mao et al. |
| 2003/0050537 A1 | 3/2003 | Wessel |
| 2003/0050546 A1 | 3/2003 | Desai et al. |
| 2003/0060753 A1 | 3/2003 | Starkweather et al. |
| 2003/0065257 A1 | 4/2003 | Mault et al. |
| 2003/0065273 A1 | 4/2003 | Mault et al. |
| 2003/0065274 A1 | 4/2003 | Mault et al. |
| 2003/0065275 A1 | 4/2003 | Mault et al. |
| 2003/0065308 A1 | 4/2003 | Lebel et al. |
| 2003/0100040 A1 | 5/2003 | Bonnecaze et al. |
| 2003/0100821 A1 | 5/2003 | Heller et al. |
| 2003/0105407 A1 | 6/2003 | Pearce et al. |
| 2003/0108976 A1 | 6/2003 | Braig et al. |
| 2003/0122021 A1 | 7/2003 | McConnell et al. |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0135100 A1 | 7/2003 | Kim et al. |
| 2003/0135333 A1 | 7/2003 | Aceti et al. |
| 2003/0153820 A1 | 8/2003 | Berner et al. |
| 2003/0153821 A1 | 8/2003 | Berner et al. |
| 2003/0158472 A1 | 8/2003 | Sohrab |
| 2003/0158707 A1 | 8/2003 | Doi |
| 2003/0168338 A1 | 9/2003 | Gao et al. |
| 2003/0175806 A1 | 9/2003 | Rule et al. |
| 2003/0176183 A1 | 9/2003 | Drucker et al. |
| 2003/0176933 A1 | 9/2003 | Lebel et al. |
| 2003/0181851 A1 | 9/2003 | Mann et al. |
| 2003/0181852 A1 | 9/2003 | Mann et al. |
| 2003/0187338 A1 | 10/2003 | Say et al. |
| 2003/0187525 A1 | 10/2003 | Mann et al. |
| 2003/0191376 A1 | 10/2003 | Samuels et al. |
| 2003/0191377 A1 | 10/2003 | Robinson et al. |
| 2003/0191431 A1 | 10/2003 | Mann et al. |
| 2003/0195403 A1 | 10/2003 | Berner et al. |
| 2003/0195462 A1 | 10/2003 | Mann et al. |
| 2003/0199790 A1 | 10/2003 | Boecker et al. |
| 2003/0199791 A1 | 10/2003 | Boecker et al. |
| 2003/0199903 A1 | 10/2003 | Boecker et al. |
| 2003/0208110 A1 | 11/2003 | Mault et al. |
| 2003/0208113 A1 | 11/2003 | Mault et al. |
| 2003/0208133 A1 | 11/2003 | Mault |
| 2003/0208409 A1 | 11/2003 | Mault |
| 2003/0212364 A1 | 11/2003 | Mann et al. |
| 2003/0212379 A1 | 11/2003 | Bylund et al. |
| 2003/0217966 A1 | 11/2003 | Tapsak et al. |
| 2003/0226695 A1 | 12/2003 | Mault |
| 2003/0229514 A2 | 12/2003 | Brown |
| 2003/0232370 A1 | 12/2003 | Trifiro |
| 2003/0235817 A1 | 12/2003 | Bartkowiak et al. |
| 2004/0010186 A1 | 1/2004 | Kimball et al. |

(56) References Cited

U.S. PATENT DOCUMENTS

| | | |
|---|---|---|
| 2004/0010207 A1 | 1/2004 | Flaherty et al. |
| 2004/0011671 A1 | 1/2004 | Shults et al. |
| 2004/0018486 A1 | 1/2004 | Dunn et al. |
| 2004/0024553 A1 | 2/2004 | Monfre et al. |
| 2004/0039256 A1 | 2/2004 | Kawatahara et al. |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0059201 A1 | 3/2004 | Ginsberg |
| 2004/0064068 A1 | 4/2004 | DeNuzzio et al. |
| 2004/0069164 A1 | 4/2004 | Nakamura et al. |
| 2004/0072357 A1 | 4/2004 | Stiene et al. |
| 2004/0073095 A1 | 4/2004 | Causey, III et al. |
| 2004/0096959 A1 | 5/2004 | Stiene et al. |
| 2004/0099529 A1 | 5/2004 | Mao et al. |
| 2004/0106858 A1 | 6/2004 | Say et al. |
| 2004/0108226 A1 | 6/2004 | Polychronakos et al. |
| 2004/0122353 A1 | 6/2004 | Shahmirian et al. |
| 2004/0122489 A1 | 6/2004 | Mazar et al. |
| 2004/0122530 A1 | 6/2004 | Hansen et al. |
| 2004/0133164 A1 | 7/2004 | Funderburk et al. |
| 2004/0133390 A1 | 7/2004 | Osorio et al. |
| 2004/0135684 A1 | 7/2004 | Steinthal et al. |
| 2004/0138588 A1 | 7/2004 | Saikley et al. |
| 2004/0147872 A1 | 7/2004 | Thompson |
| 2004/0152622 A1 | 8/2004 | Keith et al. |
| 2004/0153585 A1 | 8/2004 | Kawatahara et al. |
| 2004/0162473 A1 | 8/2004 | Sohrab |
| 2004/0164961 A1 | 8/2004 | Bal et al. |
| 2004/0167383 A1 | 8/2004 | Kim et al. |
| 2004/0167464 A1 | 8/2004 | Ireland et al. |
| 2004/0167801 A1 | 8/2004 | Say et al. |
| 2004/0171921 A1 | 9/2004 | Say et al. |
| 2004/0172284 A1 | 9/2004 | Sullivan et al. |
| 2004/0176672 A1 | 9/2004 | Silver et al. |
| 2004/0176913 A1 | 9/2004 | Kawatahara et al. |
| 2004/0186362 A1 | 9/2004 | Brauker et al. |
| 2004/0186365 A1 | 9/2004 | Jin et al. |
| 2004/0193025 A1 | 9/2004 | Steil et al. |
| 2004/0193090 A1 | 9/2004 | Lebel et al. |
| 2004/0199056 A1 | 10/2004 | Husemann et al. |
| 2004/0199059 A1 | 10/2004 | Brauker et al. |
| 2004/0202576 A1 | 10/2004 | Aceti et al. |
| 2004/0204687 A1 | 10/2004 | Mogensen et al. |
| 2004/0208780 A1 | 10/2004 | Faries et al. |
| 2004/0225338 A1 | 11/2004 | Lebel et al. |
| 2004/0248204 A1 | 12/2004 | Moerman |
| 2004/0249250 A1 | 12/2004 | McGee et al. |
| 2004/0249253 A1 | 12/2004 | Racchini et al. |
| 2004/0249254 A1 | 12/2004 | Racchini et al. |
| 2004/0249420 A1 | 12/2004 | Olson et al. |
| 2004/0249999 A1 | 12/2004 | Connolly et al. |
| 2004/0253736 A1 | 12/2004 | Stout et al. |
| 2004/0254429 A1 | 12/2004 | Yang |
| 2004/0254433 A1 | 12/2004 | Bandis et al. |
| 2004/0254434 A1 | 12/2004 | Goodnow et al. |
| 2004/0260363 A1 | 12/2004 | Von Arx et al. |
| 2004/0260478 A1 | 12/2004 | Schwamm |
| 2004/0263354 A1 | 12/2004 | Mann et al. |
| 2004/0267300 A1 | 12/2004 | Mace |
| 2005/0003470 A1 | 1/2005 | Nelson et al. |
| 2005/0004494 A1 | 1/2005 | Perez et al. |
| 2005/0010087 A1 | 1/2005 | Banet et al. |
| 2005/0010269 A1 | 1/2005 | Lebel et al. |
| 2005/0016276 A1 | 1/2005 | Guan et al. |
| 2005/0017864 A1 | 1/2005 | Tsoukalis |
| 2005/0027177 A1 | 2/2005 | Shin et al. |
| 2005/0027179 A1 | 2/2005 | Berner et al. |
| 2005/0027180 A1 | 2/2005 | Goode, Jr. et al. |
| 2005/0027181 A1 | 2/2005 | Goode, Jr. et al. |
| 2005/0027462 A1 | 2/2005 | Goode, Jr. et al. |
| 2005/0027463 A1 | 2/2005 | Goode, Jr. et al. |
| 2005/0031689 A1 | 2/2005 | Shults et al. |
| 2005/0033132 A1 | 2/2005 | Shults et al. |
| 2005/0038674 A1 | 2/2005 | Braig et al. |
| 2005/0038680 A1 | 2/2005 | McMahon |
| 2005/0043598 A1 | 2/2005 | Goode, Jr. et al. |
| 2005/0043894 A1 | 2/2005 | Fernandez |
| 2005/0049179 A1 | 3/2005 | Davidson et al. |
| 2005/0049473 A1 | 3/2005 | Desai et al. |
| 2005/0054909 A1 | 3/2005 | Petisce et al. |
| 2005/0055474 A1 | 3/2005 | Yang |
| 2005/0065464 A1 | 3/2005 | Talbot et al. |
| 2005/0090607 A1 | 4/2005 | Tapsak et al. |
| 2005/0096516 A1 | 5/2005 | Soykan et al. |
| 2005/0112169 A1 | 5/2005 | Brauker et al. |
| 2005/0113653 A1 | 5/2005 | Fox et al. |
| 2005/0113657 A1 | 5/2005 | Alarcon et al. |
| 2005/0113658 A1 | 5/2005 | Jacobson et al. |
| 2005/0114068 A1 | 5/2005 | Chey et al. |
| 2005/0118726 A1 | 6/2005 | Schultz et al. |
| 2005/0121322 A1 | 6/2005 | Say et al. |
| 2005/0124873 A1 | 6/2005 | Shults et al. |
| 2005/0131346 A1 | 6/2005 | Douglas |
| 2005/0137471 A1 | 6/2005 | Haar et al. |
| 2005/0137530 A1 | 6/2005 | Campbell et al. |
| 2005/0143635 A1 | 6/2005 | Kamath et al. |
| 2005/0143636 A1 | 6/2005 | Zhang et al. |
| 2005/0148003 A1 | 7/2005 | Keith et al. |
| 2005/0154271 A1 | 7/2005 | Rasdal et al. |
| 2005/0161346 A1 | 7/2005 | Simpson et al. |
| 2005/0171503 A1 | 8/2005 | Van Den Berghe et al. |
| 2005/0171513 A1 | 8/2005 | Mann et al. |
| 2005/0173245 A1 | 8/2005 | Feldman et al. |
| 2005/0176136 A1 | 8/2005 | Burd et al. |
| 2005/0177036 A1 | 8/2005 | Shults et al. |
| 2005/0181012 A1 | 8/2005 | Saint et al. |
| 2005/0182306 A1 | 8/2005 | Sloan |
| 2005/0182451 A1 | 8/2005 | Griffin et al. |
| 2005/0187442 A1 | 8/2005 | Cho et al. |
| 2005/0187720 A1 | 8/2005 | Goode, Jr. et al. |
| 2005/0192557 A1 | 9/2005 | Brauker et al. |
| 2005/0195930 A1 | 9/2005 | Spital et al. |
| 2005/0199494 A1 | 9/2005 | Say et al. |
| 2005/0203360 A1 | 9/2005 | Brauker et al. |
| 2005/0203707 A1 | 9/2005 | Tsutsui et al. |
| 2005/0214892 A1 | 9/2005 | Kovatchev et al. |
| 2005/0215871 A1 | 9/2005 | Feldman et al. |
| 2005/0215872 A1 | 9/2005 | Berner et al. |
| 2005/0221504 A1 | 10/2005 | Petruno et al. |
| 2005/0239154 A1 | 10/2005 | Feldman et al. |
| 2005/0239156 A1 | 10/2005 | Drucker et al. |
| 2005/0245795 A1 | 11/2005 | Goode, Jr. et al. |
| 2005/0245799 A1 | 11/2005 | Brauker et al. |
| 2005/0251083 A1 | 11/2005 | Carr-Brendel et al. |
| 2005/0261660 A1 | 11/2005 | Choi |
| 2005/0267780 A1 | 12/2005 | Ray et al. |
| 2005/0271546 A1 | 12/2005 | Gerber et al. |
| 2005/0271547 A1 | 12/2005 | Gerber et al. |
| 2005/0272640 A1 | 12/2005 | Doyle, III et al. |
| 2005/0272985 A1 | 12/2005 | Kotulla et al. |
| 2005/0277164 A1 | 12/2005 | Drucker et al. |
| 2005/0277912 A1 | 12/2005 | John |
| 2005/0287620 A1 | 12/2005 | Heller et al. |
| 2006/0001538 A1 | 1/2006 | Kraft et al. |
| 2006/0001550 A1 | 1/2006 | Mann et al. |
| 2006/0001551 A1 | 1/2006 | Kraft et al. |
| 2006/0003398 A1 | 1/2006 | Heller et al. |
| 2006/0004271 A1 | 1/2006 | Peyser et al. |
| 2006/0007017 A1 | 1/2006 | Mann et al. |
| 2006/0010098 A1 | 1/2006 | Goodnow et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0017923 A1 | 1/2006 | Ruchti et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0025663 A1 | 2/2006 | Talbot et al. |

(56) References Cited

U.S. PATENT DOCUMENTS

| | | |
|---|---|---|
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0036187 A1 | 2/2006 | Vos et al. |
| 2006/0040402 A1 | 2/2006 | Brauker et al. |
| 2006/0052679 A1 | 3/2006 | Kotulla et al. |
| 2006/0058588 A1 | 3/2006 | Zdeblick |
| 2006/0058602 A1 | 3/2006 | Kwiatkowski et al. |
| 2006/0063218 A1 | 3/2006 | Bartkowiak et al. |
| 2006/0074564 A1 | 4/2006 | Bartowiak et al. |
| 2006/0079740 A1 | 4/2006 | Silver et al. |
| 2006/0142651 A1 | 6/2006 | Brister et al. |
| 2006/0167365 A1 | 7/2006 | Bharmi |
| 2006/0167517 A1 | 7/2006 | Gill et al. |
| 2006/0167518 A1 | 7/2006 | Gill et al. |
| 2006/0167519 A1 | 7/2006 | Gill et al. |
| 2006/0173406 A1 | 8/2006 | Hayes et al. |
| 2006/0173444 A1 | 8/2006 | Choy et al. |
| 2006/0189863 A1 | 8/2006 | Peyser et al. |
| 2006/0193375 A1 | 8/2006 | Lee et al. |
| 2006/0195029 A1 | 8/2006 | Shults et al. |
| 2006/0222566 A1 | 10/2006 | Brauker et al. |
| 2006/0226985 A1 | 10/2006 | Goodnow et al. |
| 2006/0229512 A1 | 10/2006 | Petisce et al. |
| 2006/0247508 A1 | 11/2006 | Fennell |
| 2006/0247685 A1 | 11/2006 | Bharmi |
| 2006/0247710 A1 | 11/2006 | Goetz et al. |
| 2006/0247985 A1 | 11/2006 | Liamos et al. |
| 2006/0253296 A1 | 11/2006 | Liisberg et al. |
| 2006/0258929 A1 | 11/2006 | Goode et al. |
| 2006/0264785 A1 | 11/2006 | Dring et al. |
| 2006/0272652 A1 | 12/2006 | Stocker et al. |
| 2006/0277443 A1 | 12/2006 | You et al. |
| 2007/0016381 A1 | 1/2007 | Kamath et al. |
| 2007/0017983 A1 | 1/2007 | Frank et al. |
| 2007/0027381 A1 | 2/2007 | Stafford |
| 2007/0027385 A1 | 2/2007 | Brister et al. |
| 2007/0032706 A1 | 2/2007 | Kamath et al. |
| 2007/0032717 A1 | 2/2007 | Brister et al. |
| 2007/0033074 A1 | 2/2007 | Nitzan et al. |
| 2007/0038044 A1 | 2/2007 | Dobbles et al. |
| 2007/0060803 A1 | 3/2007 | Liljeryd et al. |
| 2007/0060814 A1 | 3/2007 | Stafford |
| 2007/0060869 A1 | 3/2007 | Tolle et al. |
| 2007/0073129 A1 | 3/2007 | Shah et al. |
| 2007/0078314 A1 | 4/2007 | Grounsell et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0093786 A1 | 4/2007 | Goldsmith et al. |
| 2007/0106135 A1 | 5/2007 | Sloan et al. |
| 2007/0118405 A1 | 5/2007 | Campbell et al. |
| 2007/0149873 A1 | 6/2007 | Say et al. |
| 2007/0149874 A1 | 6/2007 | Say et al. |
| 2007/0151869 A1 | 7/2007 | Heller et al. |
| 2007/0156033 A1 | 7/2007 | Causey, III et al. |
| 2007/0161879 A1 | 7/2007 | Say et al. |
| 2007/0161880 A1 | 7/2007 | Say et al. |
| 2007/0163880 A1 | 7/2007 | Woo et al. |
| 2007/0173706 A1 | 7/2007 | Neinast et al. |
| 2007/0173709 A1 | 7/2007 | Petisce et al. |
| 2007/0173710 A1 | 7/2007 | Petisce et al. |
| 2007/0173761 A1 | 7/2007 | Kanderian, Jr. et al. |
| 2007/0179370 A1 | 8/2007 | Say et al. |
| 2007/0179372 A1 | 8/2007 | Say et al. |
| 2007/0179434 A1 | 8/2007 | Weinert et al. |
| 2007/0191699 A1 | 8/2007 | Say et al. |
| 2007/0191700 A1 | 8/2007 | Say et al. |
| 2007/0191702 A1 | 8/2007 | Yodfat et al. |
| 2007/0203407 A1 | 8/2007 | Hoss et al. |
| 2007/0203408 A1 | 8/2007 | Say et al. |
| 2007/0203410 A1 | 8/2007 | Say et al. |
| 2007/0203411 A1 | 8/2007 | Say et al. |
| 2007/0203966 A1 | 8/2007 | Brauker et al. |
| 2007/0208247 A1 | 9/2007 | Say et al. |
| 2007/0213610 A1 | 9/2007 | Say et al. |
| 2007/0213657 A1 | 9/2007 | Jennewine et al. |
| 2007/0215491 A1 | 9/2007 | Heller et al. |
| 2007/0218097 A1 | 9/2007 | Heller et al. |
| 2007/0232878 A1 | 10/2007 | Kovatchev et al. |
| 2007/0232880 A1 | 10/2007 | Siddiqui et al. |
| 2007/0235331 A1 | 10/2007 | Simpson et al. |
| 2007/0244380 A1 | 10/2007 | Say et al. |
| 2007/0249919 A1 | 10/2007 | Say et al. |
| 2007/0249920 A1 | 10/2007 | Say et al. |
| 2007/0249922 A1 | 10/2007 | Peyser et al. |
| 2007/0255321 A1* | 11/2007 | Gerber et al. ............. 607/2 |
| 2007/0271285 A1 | 11/2007 | Eichorn et al. |
| 2007/0282299 A1 | 12/2007 | Hellwig |
| 2008/0004515 A1 | 1/2008 | Jennewine et al. |
| 2008/0004601 A1 | 1/2008 | Jennewine et al. |
| 2008/0009692 A1 | 1/2008 | Stafford |
| 2008/0021666 A1 | 1/2008 | Goode, Jr. et al. |
| 2008/0029391 A1 | 2/2008 | Mao et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0052317 A1 | 2/2008 | Francis et al. |
| 2008/0058625 A1 | 3/2008 | McGarraugh et al. |
| 2008/0064937 A1 | 3/2008 | McGarraugh et al. |
| 2008/0067627 A1 | 3/2008 | Boeck et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0081977 A1 | 4/2008 | Hayter et al. |
| 2008/0083617 A1 | 4/2008 | Brister et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0092638 A1 | 4/2008 | Brenneman et al. |
| 2008/0097289 A1 | 4/2008 | Steil et al. |
| 2008/0108942 A1 | 5/2008 | Brister et al. |
| 2008/0114228 A1 | 5/2008 | McCluskey et al. |
| 2008/0119703 A1 | 5/2008 | Brister et al. |
| 2008/0119708 A1 | 5/2008 | Budiman |
| 2008/0139910 A1 | 6/2008 | Mastrototaro et al. |
| 2008/0154513 A1 | 6/2008 | Kovatchev et al. |
| 2008/0161666 A1 | 7/2008 | Feldman et al. |
| 2008/0163001 A1 | 7/2008 | Ko et al. |
| 2008/0167543 A1 | 7/2008 | Say et al. |
| 2008/0172205 A1 | 7/2008 | Breton et al. |
| 2008/0177149 A1 | 7/2008 | Weinert et al. |
| 2008/0183060 A1 | 7/2008 | Steil et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0188796 A1 | 8/2008 | Steil et al. |
| 2008/0189051 A1 | 8/2008 | Goode et al. |
| 2008/0194934 A1 | 8/2008 | Ray et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0201325 A1 | 8/2008 | Doniger et al. |
| 2008/0208025 A1 | 8/2008 | Shults et al. |
| 2008/0208113 A1 | 8/2008 | Damiano et al. |
| 2008/0214900 A1 | 9/2008 | Fennell et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0234943 A1 | 9/2008 | Ray et al. |

(56) References Cited

U.S. PATENT DOCUMENTS

| | | |
|---|---|---|
| 2008/0242961 A1 | 10/2008 | Brister et al. |
| 2008/0242963 A1 | 10/2008 | Essenpreis et al. |
| 2008/0254544 A1 | 10/2008 | Modzelewski et al. |
| 2008/0255434 A1 | 10/2008 | Hayter et al. |
| 2008/0255437 A1 | 10/2008 | Hayter |
| 2008/0255808 A1 | 10/2008 | Hayter |
| 2008/0256048 A1 | 10/2008 | Hayter |
| 2008/0262469 A1 | 10/2008 | Brister et al. |
| 2008/0267823 A1 | 10/2008 | Wang et al. |
| 2008/0269714 A1 | 10/2008 | Mastrototaro et al. |
| 2008/0275313 A1 | 11/2008 | Brister et al. |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0296155 A1 | 12/2008 | Shults et al. |
| 2008/0300572 A1 | 12/2008 | Rankers et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312518 A1 | 12/2008 | Jina et al. |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2008/0314395 A1 | 12/2008 | Kovatchev et al. |
| 2008/0319085 A1 | 12/2008 | Wright et al. |
| 2008/0319279 A1 | 12/2008 | Ramsay et al. |
| 2008/0319295 A1 | 12/2008 | Bernstein et al. |
| 2008/0319296 A1 | 12/2008 | Bernstein et al. |
| 2009/0005665 A1 | 1/2009 | Hayter et al. |
| 2009/0005666 A1 | 1/2009 | Shin et al. |
| 2009/0006034 A1 | 1/2009 | Hayter et al. |
| 2009/0006061 A1 | 1/2009 | Thukral et al. |
| 2009/0006133 A1 | 1/2009 | Weinert et al. |
| 2009/0012379 A1 | 1/2009 | Goode et al. |
| 2009/0018424 A1 | 1/2009 | Kamath et al. |
| 2009/0018425 A1 | 1/2009 | Ouyang et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048503 A1 | 2/2009 | Dalal et al. |
| 2009/0054745 A1 | 2/2009 | Jennewine et al. |
| 2009/0054747 A1 | 2/2009 | Fennell |
| 2009/0054748 A1 | 2/2009 | Feldman et al. |
| 2009/0055149 A1 | 2/2009 | Hayter et al. |
| 2009/0062633 A1 | 3/2009 | Brauker et al. |
| 2009/0062635 A1 | 3/2009 | Brauker et al. |
| 2009/0062767 A1 | 3/2009 | VanAntwerp et al. |
| 2009/0063402 A1 | 3/2009 | Hayter |
| 2009/0068954 A1 | 3/2009 | Reggiardo et al. |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0085768 A1 | 4/2009 | Patel et al. |
| 2009/0093687 A1 | 4/2009 | Telfort et al. |
| 2009/0099436 A1 | 4/2009 | Brister et al. |
| 2009/0105554 A1 | 4/2009 | Stahmann et al. |
| 2009/0105560 A1 | 4/2009 | Solomon |
| 2009/0105570 A1 | 4/2009 | Sloan et al. |
| 2009/0105571 A1 | 4/2009 | Fennell et al. |
| 2009/0105636 A1 | 4/2009 | Hayter et al. |
| 2009/0112478 A1 | 4/2009 | Mueller, Jr. et al. |
| 2009/0118589 A1 | 5/2009 | Ueshima et al. |
| 2009/0124877 A1 | 5/2009 | Goode, Jr. et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0150186 A1 | 6/2009 | Cohen et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0253973 A1 | 10/2009 | Bashan et al. |
| 2009/0287073 A1 | 11/2009 | Boock et al. |
| 2009/0287074 A1 | 11/2009 | Shults et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010329 A1 | 1/2010 | Taub et al. |
| 2010/0010331 A1 | 1/2010 | Brauker et al. |
| 2010/0010332 A1 | 1/2010 | Brauker et al. |
| 2010/0011130 A1 | 1/2010 | Tasher et al. |
| 2010/0025238 A1 | 2/2010 | Gottlieb et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063372 A1 | 3/2010 | Potts et al. |
| 2010/0081906 A1 | 4/2010 | Hayter et al. |
| 2010/0081909 A1 | 4/2010 | Budiman et al. |
| 2010/0105999 A1 | 4/2010 | Dixon et al. |
| 2010/0119881 A1 | 5/2010 | Patel et al. |
| 2010/0141656 A1 | 6/2010 | Krieftewirth |
| 2010/0152554 A1 | 6/2010 | Steine et al. |
| 2010/0160759 A1 | 6/2010 | Celentano et al. |
| 2010/0168538 A1 | 7/2010 | Keenan et al. |
| 2010/0168546 A1 | 7/2010 | Kamath et al. |
| 2010/0174266 A1 | 7/2010 | Estes |
| 2010/0185175 A1 | 7/2010 | Kamen et al. |
| 2010/0190435 A1 | 7/2010 | Cook et al. |
| 2010/0191085 A1 | 7/2010 | Budiman |
| 2010/0191472 A1 | 7/2010 | Doniger et al. |
| 2010/0198142 A1 | 8/2010 | Sloan et al. |
| 2010/0213080 A1 | 8/2010 | Celentano et al. |

(56) References Cited

U.S. PATENT DOCUMENTS

| | | |
|---|---|---|
| 2010/0234710 A1 | 9/2010 | Hoss et al. |
| 2010/0274515 A1 | 10/2010 | Hoss et al. |
| 2010/0280441 A1 | 11/2010 | Willinska et al. |
| 2010/0312176 A1 | 12/2010 | Hans-Martin et al. |
| 2010/0313105 A1 | 12/2010 | Nekoomaram et al. |
| 2010/0324403 A1 | 12/2010 | Brister et al. |
| 2011/0004276 A1 | 1/2011 | Blair et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0031986 A1 | 2/2011 | Bhat et al. |
| 2011/0077490 A1 | 3/2011 | Simpson et al. |
| 2011/0148905 A1 | 6/2011 | Simmons et al. |
| 2011/0208027 A1 | 8/2011 | Wagner et al. |
| 2011/0208155 A1 | 8/2011 | Palerm et al. |
| 2011/0257895 A1 | 10/2011 | Brauker et al. |
| 2011/0263958 A1 | 10/2011 | Brauker et al. |
| 2011/0287528 A1 | 11/2011 | Fern et al. |
| 2011/0320130 A1 | 12/2011 | Valdes et al. |
| 2012/0078071 A1 | 3/2012 | Bohm et al. |
| 2012/0108934 A1 | 5/2012 | Valdes et al. |
| 2012/0173200 A1 | 7/2012 | Breton et al. |
| 2013/0035575 A1 | 2/2013 | Mayou et al. |
| 2013/0235166 A1 | 9/2013 | Jones et al. |

FOREIGN PATENT DOCUMENTS

| | | |
|---|---|---|
| CA | 2498682 | 9/2005 |
| CA | 2555749 | 9/2005 |
| CA | 2632709 | 6/2007 |
| CA | 2615575 | 6/2008 |
| CA | 2701374 | 4/2009 |
| CN | 1236824 | 1/2002 |
| DE | 4234553 | 1/1995 |
| DE | 4401400 | 7/1995 |
| EP | 0010375 | 4/1980 |
| EP | 1579690 | 11/1980 |
| EP | 0026995 | 4/1981 |
| EP | 0048090 | 3/1982 |
| EP | 0078636 | 5/1983 |
| EP | 0080304 | 6/1983 |
| EP | 0096228 | 12/1983 |
| EP | 0096288 | 12/1983 |
| EP | 0098592 | 1/1984 |
| EP | 0125139 | 11/1984 |
| EP | 0127958 | 12/1984 |
| EP | 0136362 | 4/1985 |
| EP | 0170375 | 2/1986 |
| EP | 0177743 | 4/1986 |
| EP | 0184909 | 6/1986 |
| EP | 0206218 | 12/1986 |
| EP | 0230472 | 8/1987 |
| EP | 0241309 | 10/1987 |
| EP | 0245073 | 11/1987 |
| EP | 0255291 | 2/1988 |
| EP | 0278647 | 8/1988 |
| EP | 0320109 | 6/1989 |
| EP | 0353328 | 2/1990 |
| EP | 0359831 | 3/1990 |
| EP | 0368209 | 5/1990 |
| EP | 0368290 | 5/1990 |
| EP | 0390390 | 10/1990 |
| EP | 0396788 | 11/1990 |
| EP | 0400918 | 12/1990 |
| EP | 0453283 | 10/1991 |
| EP | 0470290 | 2/1992 |
| EP | 0504835 | 9/1992 |
| EP | 0286118 | 1/1995 |
| EP | 0653718 | 5/1995 |
| EP | 0800082 | 10/1997 |
| EP | 0880936 | 12/1998 |
| EP | 0970655 | 1/2000 |
| EP | 1034734 | 9/2000 |
| EP | 1048264 | 11/2000 |
| EP | 1445746 | 8/2004 |
| EP | 1956371 | 8/2008 |
| EP | 2260757 | 12/2010 |
| GB | 1394171 | 5/1975 |
| GB | 1579690 | 11/1980 |
| GB | 1599241 | 9/1981 |
| GB | 2073891 | 10/1981 |
| GB | 2154003 | 8/1985 |
| GB | 2194892 | 3/1988 |
| GB | 2204408 | 11/1988 |
| GB | 2225637 | 6/1990 |
| GB | 2254436 | 10/1992 |
| JP | 8-154903 | 6/1996 |
| JP | 2004-000555 | 8/2004 |
| WO | WO-85/05119 | 11/1985 |
| WO | WO-86/00513 | 1/1986 |
| WO | WO-87/00513 | 1/1987 |
| WO | WO-87/06040 | 10/1987 |
| WO | WO-89/02246 | 3/1989 |
| WO | WO-89/05119 | 6/1989 |
| WO | WO-89/08713 | 9/1989 |
| WO | WO-90/00367 | 1/1990 |
| WO | WO-90/05300 | 5/1990 |
| WO | WO-90/05910 | 5/1990 |
| WO | WO-91/01680 | 2/1991 |
| WO | WO-91/04704 | 4/1991 |
| WO | WO-91/15993 | 10/1991 |
| WO | WO-92/13271 | 8/1992 |
| WO | WO-94/20602 | 9/1994 |
| WO | WO-94/27140 | 11/1994 |
| WO | WO-95/06240 | 3/1995 |
| WO | WO-96/07908 | 3/1996 |
| WO | WO-96/25089 | 8/1996 |
| WO | WO-96/30431 | 10/1996 |
| WO | WO-96/35370 | 11/1996 |
| WO | WO-97/02847 | 1/1997 |
| WO | WO-97/19344 | 5/1997 |
| WO | WO-97/20207 | 6/1997 |
| WO | WO-97/41421 | 11/1997 |
| WO | WO-97/42882 | 11/1997 |
| WO | WO-97/42883 | 11/1997 |
| WO | WO-97/42886 | 11/1997 |
| WO | WO-97/42888 | 11/1997 |
| WO | WO-97/43962 | 11/1997 |
| WO | WO-97/46868 | 12/1997 |
| WO | WO-98/09167 | 3/1998 |
| WO | WO-98/24366 | 6/1998 |
| WO | WO-98/35053 | 8/1998 |
| WO | WO-98/52045 | 11/1998 |
| WO | WO-98/52293 | 11/1998 |
| WO | WO-99/05966 | 2/1999 |
| WO | WO-99/32883 | 7/1999 |
| WO | WO-99/56613 | 11/1999 |
| WO | WO-00/13580 | 3/2000 |
| WO | WO-00/18294 | 4/2000 |
| WO | WO-00/19887 | 4/2000 |
| WO | WO-00/20626 | 4/2000 |
| WO | WO-00/32088 | 6/2000 |
| WO | WO-00/33065 | 6/2000 |
| WO | WO-00/49940 | 8/2000 |
| WO | WO-00/59370 | 10/2000 |
| WO | WO-00/62664 | 10/2000 |
| WO | WO-00/62665 | 10/2000 |
| WO | WO-00/78210 | 12/2000 |
| WO | WO-00/78992 | 12/2000 |
| WO | WO-01/24038 | 4/2001 |
| WO | WO-01/33216 | 5/2001 |
| WO | WO-01/52727 | 7/2001 |
| WO | WO-01/52935 | 7/2001 |
| WO | WO-01/54753 | 8/2001 |
| WO | WO-01/57238 | 8/2001 |
| WO | WO-01/57239 | 8/2001 |
| WO | WO-01/67009 | 9/2001 |
| WO | WO-02/13686 | 2/2002 |
| WO | WO-02/16905 | 2/2002 |

(56) References Cited

FOREIGN PATENT DOCUMENTS

| | | |
|---|---|---|
| WO | WO-02/17210 | 2/2002 |
| WO | WO-02/058537 | 8/2002 |
| WO | WO-02/078512 | 10/2002 |
| WO | WO-03/036583 | 5/2003 |
| WO | WO-03/076893 | 9/2003 |
| WO | WO-03/082091 | 10/2003 |
| WO | WO-2004/015539 | 2/2004 |
| WO | WO-2004/061420 | 7/2004 |
| WO | WO-2004/084820 | 10/2004 |
| WO | WO-2005/089103 | 9/2005 |
| WO | WO-2006/037109 | 4/2006 |
| WO | WO-2006/118947 | 11/2006 |
| WO | WO-2006/119084 | 11/2006 |
| WO | WO-2007/016399 | 2/2007 |
| WO | WO-2007/027381 | 3/2007 |
| WO | WO-2007/027788 | 3/2007 |
| WO | WO-2007/041069 | 4/2007 |
| WO | WO-2007/041070 | 4/2007 |
| WO | WO-2007/041072 | 4/2007 |
| WO | WO-2007/041248 | 4/2007 |
| WO | WO-2007/053832 | 5/2007 |
| WO | WO-2007/056638 | 5/2007 |
| WO | WO-2007/065285 | 6/2007 |
| WO | WO-2007/101260 | 9/2007 |
| WO | WO-2007/120363 | 10/2007 |
| WO | WO-2007/143225 | 12/2007 |
| WO | WO-2007/149319 | 12/2007 |
| WO | WO-2008/001366 | 1/2008 |
| WO | WO-2008/003003 | 1/2008 |
| WO | WO-2008/005780 | 1/2008 |
| WO | WO-2011/104616 | 9/2011 |

OTHER PUBLICATIONS

Morbiducci, U, et al., "Improved Usability of the Minimal Model of Insulin Sensitivity Based on an Automated Approach and Genetic Algorithms for Parameter Estimation", *Clinical Science*, vol. 112, 2007, pp. 257-263.

Parker, R., et al., "Robust H∞ Glucose Control in Diabetes Using a Physiological Model", *AIChE Journal*, vol. 46, No. 12, 2000, pp. 2537-2549.

PCT Application No. PCT/US2008/054187, International Preliminary Report on Patentability and Written Opinion of the International Searching Authority mailed Aug. 27, 2009.

PCT Application No. PCT/US2008/054187, International Search Report and Written Opinion of the International Searching Authority mailed Aug. 15, 2008.

U.S. Appl. No. 12/032,617, Office Action mailed Dec. 4, 2012.
U.S. Appl. No. 12/032,617, Office Action mailed Jun. 8, 2010.
U.S. Appl. No. 12/032,617, Office Action mailed Mar. 30, 2012.
U.S. Appl. No. 12/032,617, Office Action mailed Sep. 19, 2011.

Aussedat, B., et al., "A User-Friendly Method for Calibrating a Subcutaneous Glucose Sensor-Based Hypoglycemic Alarm", *Biosensors & Bioelectronics*, vol. 12, No. 11, 1997, pp. 1061-1070.

Bremer, T. M., et al., "Benchmark Data from the Literature for Evaluation of New Glucose Sensing Technologies", *Diabetes Technology & Therapeutics*, vol. 3, No. 3, 2001, pp. 409-418.

Cheyne, E. H., et al., "Performance of a Continuous Glucose Monitoring System During Controlled Hypoglycaemia in Healthy Volunteers", *Diabetes Technology & Therapeutics*, vol. 4, No. 5, 2002, pp. 607-613.

Garg, S., et al., "Improvement in Glycemic Excursions with a Transcutaneous, Real-Time Continuous Glucose Sensor", *Diabetes Care*, vol. 29, No. 1, 2006, pp. 44-50.

Li, Y., et al., "In Vivo Release From a Drug Delivery MEMS Device", *Journal of Controlled Release*, vol. 100, 2004, 99. 211-219.

Lodwig, V., et al., "Continuous Glucose Monitoring with Glucose Sensors: Calibration and Assessment Criteria", *Diabetes Technology & Therapeutics*, vol. 5, No. 4, 2003, pp. 573-587.

Panteleon, A. E., et al., "The Role of the Independent Variable to Glucose Sensor Calibration", *Diabetes Technology & Therapeutics*, vol. 5, No. 3, 2003, pp. 401-410.

Chinese Patent Application No. 201080006628.2, Original Language and English Translation of Office Action mailed Sep. 26, 2013.
U.S. Appl. No. 12/032,617, Notice of Allowance mailed Jan. 27, 2014.
U.S. Appl. No. 12/032,617, Office Action mailed Aug. 29, 2013.
U.S. Appl. No. 12/032,617, Office Action mailed Feb. 14, 2013.

Abruna, H. D., et al., "Rectifying Interfaces Using Two-Layer Films of Electrochemically Polymerized Vinylpyridine and Vinylbipyridine Complexes of Ruthenium and Iron on Electrodes", *Journal of the American Chemical Society*, vol. 103, No. 1, 1981, pp. 1-5.

Abstract of Japanese Publication No. JP-55-010581, Published Jan. 5, 1980.

Abstract of Japanese Publication No. JP-55-010583, Published Jan. 5, 1980.

Abstract of Japanese Publication No. JP-55-010584, Published Jan. 5, 1980.

Albery, W. J., et al., "Amperometric Enzyme Electrodes Part II: Conducting Salts as Electrode Materials for the Oxidation of Glucose Oxidase", *Journal of ElectroAnalytical Chemistry*, vol. 194, 1985, pp. 223-235.

Albery, W. J., et al., "Amperometric Enzyme Electrodes", *Philosophical Transactions of The Royal Society of London*, vol. 316, 1987, pp. 107-119.

Alcock, S. J., et al., "Continuous Analyte Monitoring to Aid Clinical Practice", *IEEE Engineering in Medicine and Biology Magazine*, 1994, pp. 319-325.

Anderson, L. B., et al., "Thin-Layer Electrochemistry: Steady-State Methods of Studying Rate Processes", *Journal of ElectroAnalytical Chemistry*, vol. 10, 1965, pp. 295-305.

Armour, J. C., et al., "Application of Chronic Intravascular Blood Glucose Sensor in Dogs", *Diabetes*, vol. 39, 1990, pp. 1519-1526.

Bartlett, P. N., et al., "Covalent Binding of Electron Relays to Glucose Oxidase", *Journal of the Chemical Society, Chemical Communications*, 1987, pp. 1603-1604.

Bartlett, P. N., et al., "Modification of Glucose Oxidase by Tetrathiafulvalene", *Journal of the Chemical Society, Chemical Communications*, 1990, pp. 1135-1136.

Bartlett, P. N., et al., "Strategies for the Development of Amperometric Enzyme Electrodes", *Biosensors*, vol. 3, 1987/88, pp. 359-379.

Bennion, N., et al., "Alternate Site Glucose Testing: A Crossover Design", *Diabetes Technology & Therapeutics*, vol. 4, No. 1, 2002, pp. 25-33.

Bindra, D. S., et al., "Design and in Vitro Studies of a Needle-Type Glucose Sensor for Subcutaneous Monitoring", *Analytical Chemistry*, vol. 63, No. 17, 1991, pp. 1692-1696.

Blank, T. B., et al., "Clinical Results From a Non-Invasive Blood Glucose Monitor", *Optical Diagnostics and Sensing of Biological Fluids and Glucose and Cholesterol Monitoring II, Proceedings of SPIE*, vol. 4624, 2002, pp. 1-10.

Bobbioni-Harsch, E., et al., "Lifespan of Subcutaneous Glucose Sensors and Their Performances During Dynamic Glycaemia Changes in Rats", *Journal of Biomedical Engineering*, vol. 15, 1993, pp. 457-463.

Boedeker Plastics, Inc., "Polyethylene Specifications", Web Page of Boedeker.com, 2007, pp. 1-3.

Brandt, J., et al., "Covalent Attachment of Proteins to Polysaccharide Carriers by Means of Benzoquinone", *Biochimica et Biophysica Acta*, vol. 386, 1975, pp. 196-202.

Brooks, S. L., et al., "Development of an On-Line Glucose Sensor for Fermentation Monitoring", *Biosensors*, vol. 3, 1987/88, pp. 45-56.

Brownlee, M., et al., "A Glucose-Controlled Insulin-Delivery System: Semisynthetic Insulin Bound to Lectin", *Science*, vol. 206, 1979, 1190-1191.

Cass, A. E., et al., "Ferricinum Ion as an Electron Acceptor for Oxido-Reductases", *Journal of ElectroAnalytical Chemistry*, vol. 190, 1985, pp. 117-127.

Cass, A. E., et al., "Ferrocene-Medicated Enzyme Electrode for Amperometric Determination of Glucose", *Analytical Chemistry*, vol. 56, No. 4, 1984, 667-671.

(56) References Cited

OTHER PUBLICATIONS

Castner, J. F., et al., "Mass Transport and Reaction Kinetic Parameters Determined Electrochemically for Immobilized Glucose Oxidase", *Biochemistry*, vol. 23 No. 10, 1984, 2203-2210.

Claremont, D. J., et al., "Biosensors for Continuous In Vivo Glucose Monitoring", *Proceedings of the Annual International Conference of the IEEE Engineering in Medicine and Biology Society*, vol. 10, 1988.

Clark Jr., L. C., et al., "Differential Anodic Enzyme Polarography for the Measurement of Glucose", *Oxygen Transport to Tissue: Instrumentation, Methods, and Physiology*, 1973, pp. 127-133.

Clark Jr., L. C., et al., "Electrode Systems for Continuous Monitoring in Cardiovascular Surgery", *Annals New York Academy of Sciences*, 1962, pp. 29-45.

Clark Jr., L. C., et al., "Long-term Stability of Electroenzymatic Glucose Sensors Implanted in Mice", *American Society of Artificial Internal Organs Transactions*, vol. XXXIV, 1988, pp. 259-265.

Clarke, W. L., et al., "Evaluating Clinical Accuracy of Systems for Self-Monitoring of Blood Glucose", *Diabetes Care*, vol. 10, No. 5, 1987, pp. 622-628.

Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.

Csoregi, E., et al., "Design, Characterization, and One-Point in Vivo Calibration of a Subcutaneously Implanted Glucose Electrode", *Analytical Chemistry*, vol. 66 No. 19, 1994, pp. 3131-3138.

Csoregi, E., et al., "On-Line Glucose Monitoring by Using Microdialysis Sampling and Amperometric Detection Based on 'Wired' Glucose Oxidase in Carbon Paste", *Mikrochimica Acta*, vol. 121, 1995, pp. 31-40.

Dai, W. S., et al., "Hydrogel Membranes with Mesh Size Asymmetry Based on the Gradient Crosslinking of Poly(vinyl alcohol)," *Journal of Membrane Science*, vol. 156, 1999, pp. 67-79.

Davis, G., "Electrochemical Techniques for the Development of Amperometric Biosensors", *Biosensors*, vol. 1, 1985, pp. 161-178.

Degani, Y., et al., "Direct Electrical Communication Between Chemically Modified Enzymes and Metal Electrodes. 1. Electron Transfer from Glucose Oxidase to Metal Electrodes via Electron Relays, Bound Covalently to the Enzyme", *The Journal of Physical Chemistry*, vol. 91, No. 6, 1987, pp. 1285-1289.

Degani, Y., et al., "Direct Electrical Communication Between Chemically Modified Enzymes and Metal Electrodes. 2. Methods for Bonding Electron-Transfer Relays to Glucose Oxidase and D-Amino-Acid Oxidase", *Journal of the American Chemical Society*, vol. 110, No. 8, 1988, pp. 2615-2620.

Degani, Y., et al., "Electrical Communication Between Redox Centers of Glucose Oxidase and Electrodes via Electrostatically and Covalently Bound Redox Polymers", *Journal of the American Chemical Society*, vol. 111, 1989, pp. 2357-2358.

Denisevich, P., et al., "Unidirectional Current Flow and Charge State Trapping at Redox Polymer Interfaces on Bilayer Electrodes: Principles, Experimental Demonstration, and Theory", *Journal of the American Chemical Society*, vol. 103, 1981, pp. 4727-4737.

Dicks, J. M., et al., "Ferrocene Modified Polypyrrole with Immobilised Glucose Oxidase and its Application in Amperometric Glucose Microbiosensors", *Annales de Biologie Clinique*, vol. 47, 1989, pp. 607-619.

Ellis, C. D., et al., "Selectivity and Directed Charge Transfer through an Electroactive Metallopolymer Film", *Journal of the American Chemical Society*, vol. 103, No. 25, 1981, pp. 7480-7483.

Engstrom, R. C., "Electrochemical Pretreatment of Glassy Carbon Electrodes", *Analytical Chemistry*, vol. 54, No. 13, 1982, pp. 2310-2314.

Engstrom, R. C., et al., "Characterization of Electrochemically Pretreated Glassy Carbon Electrodes", *Analytical Chemistry*, vol. 56, No. 2, 1984, pp. 136-141.

Feldman, B., et al., "A Continuous Glucose Sensor Based on Wired Enzyme™ Technology—Results from a 3-Day Trial in Patients with Type 1 Diabetes", *Diabetes Technology & Therapeutics*, vol. 5, No. 5, 2003, pp. 769-779.

Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*.

Feldman, B., et al., "Electron Transfer Kinetics at Redox Polymer/Solution Interfaces Using Microelectrodes and Twin Electrode Thin Layer Cells", *Journal of ElectroAnalytical Chemistry*, vol. 194, 1985, pp. 63-81.

Fischer, H., et al., "Intramolecular Electron Transfer Medicated by 4,4'-Bypyridine and Related Bridging Groups", *Journal of the American Chemical Society*, vol. 98, No. 18, 1976, pp. 5512-5517.

Flentge, F., et al., "An Enzyme-Reactor for Electrochemical Monitoring of Choline and Acetylcholine: Applications in High-Performance Liquid Chromatography, Bran Tissue, Microdialysis and Cerebrospinal Fluid," *Analytical Biochemistry*, vol. 204, 1992, pp. 305-310.

Foulds, N. C., et al., "Enzyme Entrapment in Electrically Conducting Polymers: Immobilisation of Glucose Oxidase in Polypyrrole and its Application in Amperometric Glucose Sensors", *Journal of the Chemical Society, Faraday Transactions 1*, vol. 82, 1986, pp. 1259-1264.

Foulds, N. C., et al , "Immobilization of Glucose Oxidase in Ferrocene-Modified Pyrrole Polymers", *Analytical Chemistry*, vol. 60, No. 22, 1988, pp. 2473-2478.

Frew, J. E., et al., "Electron-Transfer Biosensors", *Philosophical Transactions of The Royal Society of London*, vol. 316, 1987, pp. 95-106.

Godsland, I. F., et al., "Maximizing the Success Rate of Minimal Model Insulin Sensitivity Measurement in Humans: The Importance of Basal Glucose Levels," *Clinical Science*, vol. 101, 2001, pp. 1-9.

Gorton, L., et al., "Selective Detection in Flow Analysis Based on the Combination of Immobilized Enzymes and Chemically Modified Electrodes", *Analytica Chimica Acta*, vol. 250, 1991, pp. 203-248.

Graham, N. B., "Poly(ethylene oxide) and Related Hydrogels," *Hydrogels in Medicine and Pharmacy*, vol. II: Polymers, Chapter 4, 1987, pp. 95-113.

Gregg, B. A., et al., "Cross-Linked Redox Gels Containing Glucose Oxidase for Amperometric Bionsensor Applications", *Analytical Chemistry*, vol. 62, No. 3, 1990, pp. 258-263.

Gregg, B. A., et al., "Redox Polymer Films Containing Enzymes. 1. A Redox-Conducting Epoxy Cement: Synthesis, Characterization, and Electrocatalytic Oxidation of Hydroquinone", *Journal of Physical Chemistry*, vol. 95, No. 15, 1991, 5970-5975.

Hale, P. D., et al., "A New Class of Amperometric Biosensor Incorporating a Polymeric Electron-Transfer Mediator", *Journal of the American Chemical Society*, vol. 111, No. 9, 1989, pp. 3482-3484.

Hamilton, "Hamilton Needle Gauge Index", www.hamiltoncompany.com.

Harrison, D. J., et al., "Characterization of Perfluorosulfonic Acid Polymer Coated Enzyme Electrodes and a Miniatureized Integrated Potentiostat for Glucose Analysis in Whole Blood", *Analytical Chemistry*, vol. 60, No. 19, 1988, pp. 2002-2007.

Hawkridge, F. M., et al., "Indirect Coulometric Titration of Biological Electron Transport Components", *Analytical Chemistry*, vol. 45, No. 7, 1973, pp. 1021-1027.

Heller, A., "Electrical Connection Enzyme Redox Centers to Electrodes", *Journal of Physical Chemistry*, vol. 96, No. 9, 1990, pp. 3579-3587.

Heller, A., "Electrical Wiring of Redox Enzymes", *Accounts Chemical Research* vol. 23, No. 5, 1990, 128-134.

Heller, A., et al., "Amperometric Biosensors Based on Three-Dimensional Hydrogel-Forming Epoxy Networks", *Sensors and Actuators B*, vol. 13-14, 1993, pp. 180-183.

Ianniello, R. M., et al., "Differential Pulse Voltammetric Study of Direct Electron Transfer in Glucose Oxidase Chemically Modified Graphite Electrodes", *Analytical Chemistry*, vol. 54, No. 7, 1982, pp. 1098-1101.

Ianniello, R. M., et al , "Immobilized Enzyme Chemically Modified Electrode as an Amperometric Sensor", *Analytical Chemistry*, vol. 53, No. 13, 1981, pp. 2090-2095.

Ikeda, T., et al., "Glucose Oxidase-Immobilized Benzoquinone-Carbon Paste Electrode as a Glucose Sensor", *Agricultural and Biological Chemistry*, vol. 49, No. 2, 1985, pp. 541-543.

(56) References Cited

OTHER PUBLICATIONS

Ikeda, T., et al., "Kinetics of Outer-Sphere Electron Transfers Between Metal Complexes in Solutions and Polymeric Films on Modified Electrodes", *Journal of the American Chemical Society*, vol. 103, No. 25, 1981, pp. 7422-7425.

Isermann, R., "Supervision, Fault-Detection and Fault-Diagnosis Methods—An Introduction", *Control Engineering Practice*, vol. 5, No. 5, 1997, pp. 639-652.

Isermann, R., et al., "Trends in the Application of Model-Based Fault Detection and Diagnosis of Technical Processes", *Control Engineering Practice*, vol. 5, No. 5, 1997, pp. 709-719.

Johnson, J. M., et al., "Potential-Dependent Enzymatic Activity in an Enzyme Thin-Layer Cell", *Analytical Chemistry*, vol. 54, No. 8, 1982, pp. 1377-1383.

Johnson, K. W., "Reproducible Electrodeposition of Biomolecules for the Fabrication of Miniature Electroenzymatic Biosensors", *Sensors and Actuators B*, vol. 5, 1991, pp. 85-89.

Johnson, K. W., et al., "In vivo Evaluation of an Electroenzymatic Glucose Sensor Implanted in Subcutaneous Tissue", *Biosensors & Bioelectronics*, vol. 7, 1992, pp. 709-714.

Johnson, P. C., "Peripheral Circulation", *John Wiley & Sons*, 1978, pp. 198.

Jonsson, G., et al., "An Amperometric Glucose Sensor Made by Modification of a Graphite Electrode Surface With Immobilized Glucose Oxidase and Adsorbed Mediator", *Biosensors*, vol. 1, 1985, pp. 355-368.

Josowicz, M., et al., "Electrochemical Pretreatment of Thin Film Platinum Electrodes", *Journal of the Electrochemical Society*, vol. 135 No. 1, 1988, pp. 112-115.

Jungheim, K., et al., "How Rapid Does Glucose Concentration Change in Daily Life of Patients with Type 1 Diabetes?", pp. 250.

Jungheim, K., et al., "Risky Delay of Hypoglycemia Detection by Glucose Monitoring at the Arm", *Diabetes Care*, vol. 24, No. 7, 2001, pp. 1303-1304.

Kaplan, S. M., "Wiley Electrical and Electronics Engineering Dictionary", *IEEE Press*, 2004, pp. 141, 142, 548, 549.

Katakis, I., et al., "Electrostatic Control of the Electron Transfer Enabling Binding of Recombinant Glucose Oxidase and Redox Polyelectrolytes", *Journal of the American Chemical Society*, vol. 116, No. 8, 1994, pp. 3617-3618.

Katakis, I., et al., "L-α-Glycerophosphate and L-Lactate Electrodes Based on the Electrochemical 'Wiring' of Oxidases", *Analytical Chemistry*, vol. 64, No. 9, 1992, pp. 1008-1013.

Kemp, G. J., "Theoretical Aspects of One-Point Calibration: Causes and Effects of Some Potential Errors, and Their Dependence on Concentration," *Clinical Chemistry*, vol. 30, No. 7, 1984, pp. 1163-1167.

Kenausis, G., et al., "'Wiring' of Glucose Oxidase and Lactate Oxidase Within a Hydrogel Made with Poly(vinyl pyridine) complexed with [Os(4,4'-dimethoxy-2,2'-bipyridine)$_2$Cl]$^{+/2+}$", *Journal of the Chemical Society, Faraday Transactions*, vol. 92, No. 20, 1996, pp. 4131-4136.

Kerner, W., et al., "The Function of a Hydrogen Peroxide-Detecting Electroenzymatic Glucose Electrode is Markedly Impaired in Human Subcutaneous Tissue and Plasma," *Biosensors & Bioelectronics*, vol. 8, 1993, pp. 473-482.

Korf, J., et al., "Monitoring of Glucose and Lactate Using Microdialysis: Applications in Neonates and Rat Brain," *Developmental Neuroscience*, vol. 15, 1993, pp. 240-246.

Koudelka, M., et al., "In-Vivo Behaviour of Hypodermically Implanted Microfabricated Glucose Sensors", *Biosensors & Bioelectronics*, vol. 6, 1991, pp. 31-36.

Kulys, J., et al., "Mediatorless Peroxidase Electrode and Preparation of Bienzyme Sensors", *Bioelectrochemistry and Bioenergetics*, vol. 24, 1990, pp. 305-311.

Lager, W., et al., "Implantable Electrocatalytic Glucose Sensor", *Hormone Metabolic Research*, vol. 26, 1994, pp. 526-530.

Laurell, T., "A Continuous Glucose Monitoring System Based on Microdialysis", *Journal of Medical Engineering & Technology*, vol. 16, No. 5, 1992, pp. 187-193.

Lindner, E., et al., "Flexible (Kapton-Based) Microsensor Arrays of High Stability for Cardiovascular Applications", *Journal of the Chemical Society, Faraday Transactions*, vol. 89, No. 2, 1993, pp. 361-367.

Lortz, J., et al., "What is Bluetooth? We Explain The Newest Short-Range Connectivity Technology", *Smart Computing Learning Series, Wireless Computing*, vol. 8, Issue 5, 2002, pp. 72-74.

Maidan, R., et al., "Elimination of Electrooxidizable Interferant-Produced Currents in Amperometric Biosensors", *Analytical Chemistry*, vol. 64, No. 23, 1992, pp. 2889-2896.

Malin, S. F., et al., "Noninvasive Prediction of Glucose by Near-Infrared Diffuse Reflectance Spectoscopy", *Clinical Chemistry*, vol. 45, No. 9, 1999, pp. 1651-1658.

Marko-Varga, G., et al., "Enzyme-Based Biosensor as a Selective Detection Unit in Column Liquid Chromatography", *Journal of Chromatography A*, vol. 660, 1994, pp. 153-167.

Mastrototaro, J. J., et al., "An Electroenzymatic Glucose Sensor Fabricated on a Flexible Substrate", *Sensors and Actuators B*, vol. 5, 1991, pp. 139-144.

Mauras, N., et al., "Lack of Accuracy of Continuous Glucose Sensors in Healthy, Nondiabetic Children: Results of the Diabetes Research in Children Network (DirecNet) Accuracy Study," *Journal of Pediatrics*, 2004, pp. 770-775.

McGarraugh, G., et al., "Glucose Measurements Using Blood Extracted from the Forearm and the Finger", *TheraSense, Inc.*, 16 Pages.

McGarraugh, G., et al., "Physiological Influences on Off-Finger Glucose Testing", *Diabetes Technology & Therapeutics*, vol. 3, No. 3, 2001, pp. 367-376.

McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.

McNeil, C. J., et al., "Thermostable Reduced Nicotinamide Adenine Dinucleotide Oxidase: Application to Amperometric Enzyme Assay", *Analytical Chemistry*, vol. 61, No. 1, 1989, pp. 25-29.

Miyawaki, O., et al., "Electrochemical and Glucose Oxidase Coenzyme Activity of Flavin Adenine Dinucleotide Covalently Attached to Glassy Carbon at the Adenine Amino Group", *Biochimica et Biophysica Acta*, vol. 838, 1985, pp. 60-68.

Moatti-Sirat, D., et al., "Evaluating In Vitro and In Vivo the Interference of Ascorbate and Acetaminophen on Glucose Detection by a Needle-Type Glucose Sensor", *Biosensors & Bioelectronics*, vol. 7, 1992, pp. 345-352.

Moatti-Sirat, D., et al., "Reduction of Acetaminophen Interference in Glucose Sensors by a Composite Nafion Membrane: Demonstration in Rats and Man", *Diabetologia*, vol. 37, 1994, pp. 610-616.

Moatti-Sirat, D., et al., "Towards Continuous Glucose Monitoring: In Vivo Evaluation of a Miniaturized Glucose Sensor Implanted for Several Days in Rat Subcutaneous Tissue", *Diabetologia*, vol. 35, 1992, pp. 224-330.

Nagy, G., et al., "A New Type of Enzyme Electrode: The Ascorbic Acid Eliminator Electrode", *Life Sciences*, vol. 31, No. 23, 1982, pp. 2611-2616.

Nakamura, S., et al., "Effect of Periodate Oxidation on the Structure and Properties of Glucose Oxidase", *Biochimica et Bio h sica Acta.*, vol. 445, 1976, pp. 294-308.

Narasimham, K., et al., "p-Benzoquinone Activation of Metal Oxide Electrodes for Attachment of Enzymes", *Enzyme and Microbial Technology*, vol. 7, 1985, pp. 283-286.

Ohara, T. J., "Osmium Bipyridyl Redox Polymers Used in Enzyme Electrodes", *Platinum Metals Review*, vol. 39, No. 2, 1995, pp. 54-62.

Ohara, T. J., et al., "'Wired' Enzyme Electrodes for Amperometric Determination of Glucose or Lactate in the Presence of Interfering Substances", *Analytical Chemistry*, vol. 66, No. 15, 1994, pp. 2451-2457.

Ohara, T. J., et al., "Glucose Electrodes Based on Cross-Linked [Os(bpy)$_2$Cl]$^{+/2+}$ Complexed Poly(1-Vinylimidazole) Films", *Analytical Chemistry*, vol. 65, No. 23, 1993, pp. 3512-3517.

Olievier, C. N., et al., "In Vivo Measurement of Carbon Dioxide Tension with a Miniature Electrodes", *Pflugers Archiv: European Journal of Physiology*, vol. 373, 1978, pp. 269-272.

(56) References Cited

OTHER PUBLICATIONS

Paddock, R. M., et al., "Electrocatalytic Reduction of Hydrogen Peroxide via Direct Electron Transfer From Pyrolytic Graphite Electrodes to Irreversibly Adsorbed Cyctochrome C Peroxidase", *Journal of ElectroAnalytical Chemistry*, vol. 260, 1989, pp. 487-494.
Palleschi, G., et al., "A Study of Interferences in Glucose Measurements in Blood by Hydrogen Peroxide Based Glucose Probes", *Analytical Biochemistry*, vol. 159, 1986, pp. 114-121.
Pankratov, I., et al., "Sol-Gel Derived Renewable-Surface Biosensors", *Journal of ElectroAnalytical Chemistry*, vol. 393, 1995, pp. 35-41.
Pathak, C., et al., "Rapid Photopolymerization of Immunoprotective Gels in Contact with Cells and Tissue", *Journal of the American Chemical Society*, vol. 114, No. 21, 1992, pp. 8311-8312.
Pickup, J., "Developing Glucose Sensors for In Vivo Use", *Tibtech*, vol. 11, 1993, pp. 285-291.
Pickup, J., et al., "Implantable Glucose Sensors: Choosing the Appropriate Sensing Strategy", *Biosensors*, vol. 3, 1987/88, pp. 335-346.
Pickup, J., et al., "In Vivo Molecular Sensing in Diabetes Mellitus: An Implantable Glucose Sensor with Direct Electron Transfer", *Diabetologia*, vol. 32, 1989, pp. 213-217.
Pickup, J., et al., "Potentially-Implantable, Amperometric Glucose Sensors with Mediated Electron Transfer: Improving the Operating Stability", *Biosensors*, vol. 4, 1989, pp. 109-119.
Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.
Poitout, V., et al., "A Glucose Monitoring System for On Line Estimation in Man of Blood Glucose Concentration Using a Miniaturized Glucose Sensor Implanted in the Subcutaneous Tissue and a Wearable Control Unit", *Diabetolgia*, vol. 36, 1993, pp. 658-663.
Poitout, V., et al., "Calibration in Dogs of a Subcutaneous Miniaturized Glucose Sensor Using a Glucose Meter for Blood Glucose Determination", *Biosensors & Bioelectronics*, vol. 7, 1992, pp. 587-592.
Poitout, V., et al., "In Vitro and In Vivo Evaluation in Dogs of a Miniaturized Glucose Sensor", *ASAIO Transactions*, vol. 37, No. 3, 1991, pp. M298-M300.
Pollak, A., et al., "Enzyme Immobilization by Condensation Copolymerization into Cross-Linked Polyacrylamide Gels", *Journal of the American Chemical Society*, vol. 102, No. 20, 1980, pp. 6324-6336.
Quinn, C. P., et al., "Kinetics of Glucose Delivery to Subcutaneous Tissue in Rats Measured with 0.3-mm Amperometric Microsensors", *The American Physiological Society*, 1995, E155-E161.
Reach, G., et al., "Can Continuous Glucose Monitoring Be Used for the Treatment of Diabetes?", *Analytical Chemistry*, vol. 64, No. 6, 1992, pp. 381-386.
Rebrin, K., et al., "Automated Feedback Control of Subcutaneous Glucose Concentration in Diabetic Dogs", *Diabetologia*, vol. 32, 1989, pp. 573-576.
Reusch, W., "Other Topics: Organometallic Chemistry: Organometallic Compounds: Main Group Organometallic Compounds," *Virtual Textbook of Organic Chemistry*, 1999, Rev. 2007, 25 pages.
Roe, J. N., et al., "Bloodless Glucose Measurements", *Critical Review in Therapeutic Drug Carrier Systems*, vol. 15, Issue 3, 1998, pp. 199-241.
Sacks (ED), "Guidelines and Recommendations for Laboratory Analysis in the Diagnosis and Management of Diabetes Mellitus," *The National Academy of Clinical Biochemistry Presents Laboratory Medicine Practice Guidelines*, vol. 13, 2002, pp. 8-11, 21-23, 52-56, 63.
Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.
Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.
Salehi, C., et al., "A Telemetry-Instrumentation System for Long-Term Implantable Glucose and Oxygen Sensors", *Analytical Letters*, vol. 29, No. 13, 1996, pp. 2289-2308.
Samuels, G. J., et al., "An Electrode-Supported Oxidation Catalyst Based on Ruthenium (IV). pH 'Encapsulation' in a Polymer Film", *Journal of the American Chemical Society*, vol. 103, No. 1981, pp. 307-312.
Sasso, S. V., et al., "Electropolymerized 1,2-Diaminobenzene as a Means to Prevent Interferences and Fouling and to Stabilize Immobilized Enzyme in Electrochemical Biosensors", *Analytical Chemistry*, vol. 62, No. 11, 1990, pp. 1111-1117.
Scheller, F. W., et al., "Second Generation Biosensors," *Biosensors & Bioelectronics*, vol. 6, 1991, pp. 245-253.
Scheller, F., et al., "Enzyme Electrodes and Their Application", Philosophical Transactions of The Royal Society of London B, vol. 316, 1987, pp. 85-94.
Schmehl, R. H., et al., "The Effect of Redox Site Concentration on the Rate of Mediated Oxidation of Solution Substrates by a Redox Copolymer Film", *Journal of ElectroAnalytical Chemistry*, vol. 152, 1983, pp. 97-109.
Schmidt, F. J., et al., "Calibration of a Wearable Glucose Sensor", *The International Journal of Artificial Organs*, vol. 15, No. 1, 1992, pp. 55-61.
Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.
Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.
Shichiri, M., et al., "Glycaemic Control in Pancreatectomized Dogs with a Wearable Artificial Endocrine Pancreas", *Diabetologia*, vol. 24, 1983, pp. 179-184.
Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.
Shichiri, M., et al., "Membrane Design for Extending the Long-Life of an Implantable Glucose Sensor", *Diabetes Nutrition and Metabolism*, vol. 2, 1989, pp. 309-313.
Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.
Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 1986, pp. 298-301.
Shichiri, M., et al., "Wearable Artificial Endocrine Pancreas With Needle-Type Glucose Sensor", *The Lancet*, 1982, pp. 1129-1131.
Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.
Sittampalam, G., et al., "Surface-Modified Electrochemical Detector for Liquid Chromatography", *Analytical Chemistry*, vol. 55, No. 9, 1983, pp. 1608-1610.
Skoog, D. A., et al., "Evaluation of Analytical Data," *Fundamentals of Analytical Chemistry*, 1966, pp. 55.
Soegijoko, S., et al., "External Artificial Pancreas: A New Control Unit Using Microprocessor", *Hormone and Metabolic Research Supplement Series*, vol. 12, 1982, pp. 165-169.
Sprules, S. D., et al., "Evaluation of a New Disposable Screen-Printed Sensor Strip for the Measurement of NADH and Its Modification to Produce a Lactate Biosensor Employing Microliter Volumes", *Electroanalysis*, vol. 8, No. 6, 1996, pp. 539-543.
Sternberg, F., et al., "Calibration Problems of Subcutaneous Glucosensors when Applied 'In-Situ' in Man", *Hormone and Metabolic Research*, vol. 26, 1994, pp. 523-526.
Sternberg, R., et al., "Covalent Enzyme Coupling on Cellulose Acetate Membranes for Glucose Sensor Development", *Analytical Chemistry*, vol. 60, No. 24, 1988, pp. 2781-2786.

(56) References Cited

OTHER PUBLICATIONS

Sternberg, R., et al., "Study and Development of Multilayer Needle-Type Enzyme-Based Glucose Microsensors", *Biosensors*, vol. 4, 1988, pp. 27-40.

Suekane, M , "Immobilization of Glucose Isomerase", *Zettschrift fur Allgemeine Mikrobiologie*, vol. 22, No. 8, 1982, pp. 565-576.

Tajima, S., et al., "Simultaneous Determination of Glucose and 1,5-Anydroglucitol", *Chemical Abstracts*, vol. 111, No. 25, 1989, pp. 394.

Takamura, A., et al., Drug release from Poly(vinyl alcohol) Gel Prepared by Freeze-Thaw Procedure, *Journal of Controlled Release*, vol. 20, 1992, pp. 21-27.

Tarasevich, M. R., "Bioelectrocatalysis", *Comprehensive Treatise of Electrochemistry*, vol. 10, 1985, pp. 231-295.

Tatsuma, T., et al., "Enzyme Monolayer- and Bilayer-Modified Tin Oxide Electrodes for the Determination of Hydrogen Peroxide and Glucose", *Analytical Chemistry*, vol. 61, No. 21, 1989, pp. 2352-2355.

Taylor, C., et al., "'Wiring' of Glucose Oxidase Within a Hydrogel Made with Polyvinyl Imidazole Complexed with [(Os-4,4'-dimethoxy-2,2'-bipyridine)Cl]$^{+/2+}$", *Journal of ElectroAnalytical Chemistry*, vol. 396, 1995, pp. 511-515.

Thompson, M., et al., "In Vivo Probes: Problems and Perspectives", *Clinical Biochemistry*, vol. 19, 1986, pp. 255-261.

Travenol Laboratories, Inc., An Introduction to "Eugly", Book 1, 1985, pp. 1-22.

Trojanowicz, M., et al., "Enzyme Entrapped Polypyrrole Modified Electrode for Flow-Injection Determination of Glucose", *Biosensors & Bioelectronics*, vol. 5, 1990, pp. 149-156.

Tsalikian, E., et al., "Accuracy of the GlucoWatch G2® Biographer and the Continuous Glucose Monitoring System During Hypoglycemia: Experience of the Diabetes Research in Children Network", *Diabetes Care*, vol. 27, No. 3, 2004, pp. 722-726.

Turner, A., et al., "Diabetes Mellitus: Biosensors for Research and Management", *Biosensors*, vol. 1, 1985, pp. 85-115.

Turner, R. F., et al., "A Biocompatible Enzyme Electrode for Continuous in vivo Glucose Monitoring in Whole Blood", *Sensors and Actuators B*, vol. 1, 1990, pp. 561-564.

Tuzhi, P., et al., "Constant Potential Pretreatment of Carbon Fiber Electrodes for In Vivo Electrochemistry", *Analytical Letters*, vol. 24, No. 6, 1991, pp. 935-945.

Umana, M., "Protein-Modified Electrochemically Active Biomaterial Surface", *U.S. Army Research Office, Analytical and Chemical Sciences Research Triangle Institute*, 1988, pp. 1-9.

Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring, Chapter 4*, 1997, pp. 117-137.

Urban, G., et al., "Miniaturized Thin-Film Biosensors Using Covalently Immobilized Glucose Oxidase", *Biosensors & Bioelectronics*, vol. 6, 1991, pp. 555-562.

Velho, G., et al., "In Vitro and In Vivo Stability of Electrode Potentials in Needle-Type Glucose Sensors", *Diabetes*, vol. 38, No. 2, 1989, pp. 164-171.

Velho, G., et al., "Strategies for Calibrating a Subcutaneous Glucose Sensor", *Biomedica Biochimica Acta*, vol. 48, 1989, pp. 957-964.

Von Woedtke, T., et al., "In Situ Calibration of Implanted Electrochemical Glucose Sensors", *Biomedica Biochimica Acta*, vol. 48, 1989, pp. 943-952.

Vreeke, M. S., et al., "Hydrogen Peroxide Electrodes Based on Electrical Connection of Redox Centers of Various Peroxidases to Electrodes through a Three-Dimensional Electron-Relaying Polymer Network", *Diagnostic Biosensors Polymers, Chapter 15*, 1993, pp. 180-193.

Vreeke, M., et al., "Hydrogen Peroxide and β-Nicotinamide Adenine Dinucleotide Sensing Amperometric Electrodes Based on Electrical Connection of Horseradish Peroxidase Redox Centers to Electrodes through a Three-Dimensional Electron Relaying Polymer Network", *Analytical Chemistry*, vol. 64, No. 24, 1992, pp. 3084-3090.

Wang, D. L., et al., "Miniaturized Flexible Amperometric Lactate Probe", *Analytical Chemistry*, vol. 65, No. 8, 1993, pp. 1069-1073.

Wang, J., et al., "Activation of Glassy Carbon Electrodes by Alternating Current Electrochemical Treatment", *Analytica Chimica Acta*, vol. 167, 1985, pp. 325-334.

Wang, J., et al., "Amperometric Biosensing of Organic Peroxides with Peroxidase-Modified Electrodes", *Analytica Chimica Acta*, vol. 254, 1991, pp. 81-88.

Wang, J., et al., "Screen-Printable Sol-Gel Enzyme-Containing Carbon Inks", *Analytical Chemistry*, vol. 68, No. 15, 1996, pp. 2705-2708.

Wang, J., et al., "Sol-Gel-Derived Metal-Dispersed Carbon Composite Amperometric Biosensors", *Electroanalysis*, vol. 9, No. 1, 1997, pp. 52-55.

Williams, D. L., et al., "Electrochemical-Enzymatic Analysis of Blood Glucose and Lactate", *Analytical Chemistry*, vol. 42, No. 1, 1970, pp. 118-121.

Wilson, G. S., et al., "Progress Toward the Development of an Implantable Sensor for Glucose", *Clinical Chemistry*, vol. 38, No. 9, 1992, pp. 1613-1617.

Yabuki, S., et al., "Electro-Conductive Enzyme Membrane", *Journal of the Chemical Society, Chemical Communications*, 1989, pp. 945-946.

Yang, C., et al., "A Comparison of Physical Properties and Fuel Cell Performance of Nafion and Zirconium Phosphate/Nafion Composite Membranes," *Journal of Membrane Science*, vol. 237, 2004, pp. 145-161.

Yang, L., et al., "Determination of Oxidase Enzyme Substrates Using Cross-Flow Thin-Layer Amperometry", *Electroanalysis*, vol. 8, No. 8-9, 1996, pp. 716-721.

Yao, S. J., et al., "The Interference of Ascorbate and Urea in Low-Potential Electrochemical Glucose Sensing", *Proceedings of the Twelfth Annual International Conference of the IEEE Engineering in Medicine and Biology Society*, vol. 12, Part 2, 1990, pp. 487-489.

Yao, T., "A Chemically-Modified Enzyme Membrane Electrode as an Amperometric Glucose Sensor", *Analytica Chimica Acta*, vol. 148, 1983, pp. 27-33.

Ye, L., et al., "High Current Density 'Wired' Quinoprotein Glucose Dehydrogenase Electrode", *Analytical Chemistry*, vol. 65, No. 3, 1993, pp. 238-241.

Yildiz, A., et al., "Evaluation of an Improved Thin-Layer Electrode", *Analytical Chemistry*, vol. 40, No. 7, 1968, pp. 1018-1024.

Zamzow, K., et al., "New Wearable Continuous Blood Glucose Monitor (BGM) and Artificial Pancreas (AP)", *Diabetes*, vol. 39, 1990, pp. 5A-20.

Zhang, Y., et al., "Application of Cell Culture Toxicity Tests to the Development of Implantable Biosensors", *Biosensors & Bioelectronics*, vol. 6, 1991, pp. 653-661.

Zhang, Y., et al., "Elimination of the Acetaminophen Interference in an Implantable Glucose Sensor", *Analytical Chemistry*, vol. 66, No. 7, 1994, pp. 1183-1188.

* cited by examiner

620

700

MULTI-FUNCTION ANALYTE TEST DEVICE AND METHODS THEREFOR

RELATED APPLICATIONS

The present application claims priority under 35 U.S.C. §119(e) to U.S. provisional application No. 61/149,989 filed Feb. 4, 2009 entitled "Multi-Function Analyte Test Device and Methods Therefor", the disclosure of which is incorporated herein by reference for all purposes. The present application is also a continuation-in-part of U.S. patent application Ser. No. 12/032,617 filed Feb. 15, 2008, now U.S. Pat. No. 8,732,188, which claims priority to U.S. provisional application No. 60/890,492 filed Feb. 18, 2007, the disclosures of each of which are incorporated herein by reference for all purposes. The present application is related to U.S. patent application Ser. No. 12/699,653 concurrently filed on Feb. 3, 2010 entitled "Multi-Function Analyte Test Device and Methods Therefor", which is assigned to the assignee of the present application, Abbott Diabetes Care Inc., and the disclosure of which is incorporated herein by reference for all purposes.

BACKGROUND

In diabetes management, there exists devices which allow diabetic patients to measure their blood glucose levels. One such device is a hand-held electronic meter such as a blood glucose meter such as the Freestyle® blood glucose monitoring system available from Abbott Diabetes Care Inc., of Alameda, Calif. which receives blood samples via enzyme-based test strips. Typically, the patient lances a finger or alternate body site to obtain a blood sample, applies the drawn blood sample to the test strip, and inserts the test strip into a test strip opening or port in the meter housing for analysis and determination of the corresponding blood glucose value which is displayed or otherwise provided to the patient to show the level of glucose at the time of testing.

With the decreasing cost of electronic components and a corresponding increase in data processing capabilities of microprocessors, computational capability of electronic devices have been rapidly increasing. However, currently available glucose meters are generally configured with limited functionalities related to glucose testing. Additionally, patients who rely on the usage of glucose meters or other health related devices to monitor and treat health conditions, such as diabetes, also rely on a supply of consumable products employed by said glucose meters or other health related devices.

For patients who are frequent users of the health related devices, such as diabetics that test glucose levels and possibly administer insulin several times daily, having a sufficient supply of the test strips and insulin is critical. More often than not, it is the case that patients run out of the test strips or insulin, which necessitates a trip to the drugstore or healthcare professional office, which in some cases, may not be practical or convenient. Furthermore, it is also inconvenient to consistently maintain a log or keep track of the number of test strips and amount of insulin that remains until replenishment strips and insulin are purchased. On the other hand, it is wasteful to simply purchase a large quantity of test strips and insulin for storage, which may eventually be lost, that take up storage space, may have an expiration date after which use of the item may be undesirable to the health of the patient, and include an up front cost. This is also true for many other medical testing or monitoring devices, including, for example, measurement of blood coagulation times, cholesterol and lipids, and other diagnostic monitoring tests.

SUMMARY

In view of the foregoing, in accordance with the various embodiments of the present disclosure, there are provided methods, devices and/or systems for providing a medication dosage calculation function into a health monitor device, such as a blood glucose meter, configured to perform data analysis and management based on, for example, the glucose level detected using the health monitor device. More specifically, in accordance with the various aspects of the present disclosure, methods, systems and devices for detecting an analyte sample, determining an analyte concentration associated with the detected analyte sample, retrieving stored one or more dose determination information and associated analyte concentration associated with the retrieved one or more dose determination information, and determining a current dose level based at least in part on the determined analyte concentration and the retrieved prior dose determination information, where the determined current dose level includes a predetermined type of medication classification are provided.

These and other objects, features and advantages of the present disclosure will become more fully apparent from the following detailed description of the embodiments, the appended claims and the accompanying drawings.

INCORPORATION BY REFERENCE

The following patents, applications and/or publications are incorporated herein by reference for all purposes: U.S. Pat. Nos. 4,545,382; 4,711,245; 5,262,035; 5,262,305; 5,264,104; 5,320,715; 5,356,786; 5,509,410; 5,543,326; 5,593,852; 5,601,435; 5,628,890; 5,820,551; 5,822,715; 5,899,855; 5,918,603; 6,071,391; 6,103,033; 6,120,676; 6,121,009; 6,134,461; 6,143,164; 6,144,837; 6,161,095; 6,175,752; 6,270,455; 6,284,478; 6,299,757; 6,338,790; 6,377,894; 6,461,496; 6,503,381; 6,514,460; 6,514,718; 6,540,891; 6,560,471; 6,579,690; 6,591,125; 6,592,745; 6,600,997; 6,605,200; 6,605,201; 6,616,819; 6,618,934; 6,650,471; 6,654,625; 6,676,816; 6,730,200; 6,736,957; 6,746,582; 6,749,740; 6,764,581; 6,773,671; 6,881,551; 6,893,545; 6,932,892; 6,932,894; 6,942,518; 7,041,468; 7,167,818; and 7,299,082; U.S. Published Application Nos. 2004/0186365; 2005/0182306; 2006/0025662; 2006/0091006; 2007/0056858; 2007/0068807; 2007/0095661; 2007/0108048; 2007/0199818; 2007/0227911; 2007/0233013; 2008/0066305; 2008/0081977; 2008/0102441; 2008/0148873; 2008/0161666; 2008/0267823; and 2009/0054748; U.S. patent application Ser. No. 11/461,725, now U.S. Pat. No. 7,866,026; Ser. Nos. 12/131,012; 12/242,823, now U.S. Pat. No. 8,219,173; Ser. No. 12/363,712, now U.S. Pat. No. 8,346,335; Ser. No. 12/495,709; and Ser. No. 12/698,124; and U.S. Provisional Application Serial Nos. 61/149,639; 61/155,889; 61/155,891; 61/155,893; 61/165,499; 61/230,686; 61/227,967 and 61/238,461.

DETAILED DESCRIPTION

As described in further detail below, in accordance with the various embodiments of the present disclosure, there are provided health monitor devices, such as blood glucose meter devices, that include therapy management including for example, medication dosage calculation functions, such as a single-dose calculation function for administration of rapid acting insulin and/or long acting insulin, and/or related data analysis capabilities incorporated in the health monitor devices. In certain aspects of the present disclosure, method, device or system are provided to determine therapy management profile, recommended medication dose information based on, for example, fast or rapid acting and/or long acting insulin, to treat physiological conditions associated with diabetes or other appropriate conditions. In the manner described, in aspects of the present disclosure, patients with Type-1 or Type-2 diabetic conditions may improve their diabetes management, and further, the patients, users or healthcare providers may be provided with tools to improve the treatment of such conditions.

Figure 1:
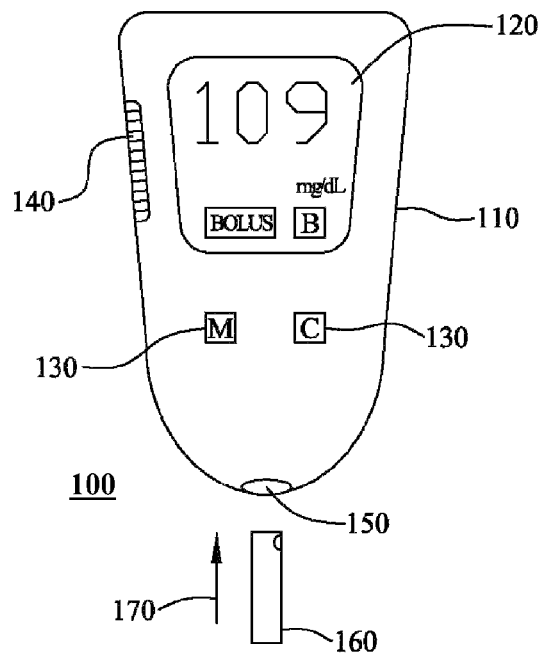
FIG. 1 is a health monitor device with a medication dose calculation function in accordance with one embodiment of the present disclosure.

FIG. 1 shows a health monitor device with a medication dose calculation function in accordance with one embodiment of the present disclosure. Health monitor device with a medication dose calculation function 100 includes a housing 110 with a display unit 120 provided thereon. Also shown in FIG. 1 is a plurality of input buttons 130, each configured to allow the user of the health monitor device with a medication dose calculation function 100 to input or enter data or relevant information associated with the operation of the health monitor device with a medication dose calculation function 100. For example, the user of the health monitor device with a medication dose calculation function may operate the one or more input buttons 130 to enter a calibration code associated with a test strip 160, or other fluid sample reception means, for use in conjunction with the health monitor device with a medication dose calculation function 100.

In one embodiment, the health monitor device with a medication dose calculation function 100 may include a blood glucose meter with bolus calculation function configured to calculate a single dose bolus dosage of a medication such as insulin such as long acting, fast acting or rapid acting insulin. The test strip 160 for use in conjunction with the health monitor device with a medication dose calculation function 100, may be a blood glucose test strip configured to receive a blood sample thereon, in order to determine a blood glucose level of the received blood sample. Additionally, the user may operate the one or more input buttons 130 to adjust time and/or date information, as well as other features or settings associated with the operation of the health monitor device with a medication dose calculation function 100.

In aspects of the present disclosure, the strip port for receiving the test strip 160 may be integrated with the housing of the health monitor device 100, or alternatively, may be provided in a separate housing or as a separate component that may be physically or electrically coupled to the health monitoring device 100. In one aspect, a component including the strip port may be provided in a separate snap-on type housing which physically snaps onto the housing of the health monitor device 100. Additional information is provided in U.S. Pat. No. 7,041,468 issued on May 9, 2006 titled "Blood Glucose Tracking Apparatus and Method" and in US Patent Application Publication No. US2004/0254434 published Dec. 16, 2004 titled "Glucose Measuring Module and Insulin Pump Combination", the disclosure of each of which is incorporated herein by reference for all purposes.

Referring back to FIG. 1, also shown is input unit 140 which, in one embodiment, may be configured as a jog dial, or the like, and provided on the housing 110 of the health monitor device with a medication dose calculation function 100. In one embodiment, as discussed in further detail below, the user or the patient may operate the input unit 140 to perform calculations and determinations associated with one or more medication dose estimation functions, such as a bolus dose estimation function, of the health monitor device with a medication dose calculation function 100. Also shown in FIG. 1 is a strip port 150 which is configured to receive the test strip 160 (with fluid sample provided thereon) substantially in the direction as shown by the directional arrow 170.

In operation, when the test strip 160 with the patient's fluid sample such as a blood sample is inserted into the strip port 150 of the health monitor device with a medication dose calculation function 100, a microprocessor or a controller unit 210 (FIG. 2) of the health monitor device with a medication dose calculation function 100 may be configured to determine the associated analyte level in the fluid sample, and display the determined analyte level on the display unit 120.

In addition, in accordance with the various embodiments of the present disclosure, the health monitor device with a medication dose calculation function 100 may be configured to automatically enter into a medication dosage calculation mode to, for example, estimate a medication dosage amount based on information stored in the health monitor device with a medication dose calculation function 100 (such as the patient's insulin sensitivity, for example), and/or prompt the patient to provide additional information, such as the amount of carbohydrate to be ingested by the patient for determination of, for example, a carbohydrate bolus dosage determination. The patient may operate the input unit 140 in conjunction with the user interface menu provided on the display unit 120 to provide the appropriate information.

In another embodiment, the health monitor device with a medication dose calculation function 100 may be configured to prompt the patient to select whether to retrieve a predetermined or preprogrammed medication dosage amount such as, for example, a correction bolus or a carbohydrate bolus, following the display of the determined analyte level from the test strip 160. In this manner, in one embodiment of the present disclosure, the health monitor device with a medication dose calculation function 100 may be configured to automatically prompt the user or patient to select whether a medication dosage determination is desired following an analyte test using the test strip 160.

Example embodiments of the present disclosure are directed mainly toward measuring the levels of glucose, such as a blood glucose level, however it is to be understood that the present embodiments may also be configured to measure the levels of other analytes, drugs, or physiological conditions. For example, analyte levels that may be determined include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones (e.g., ketone bodies), lactate, oxygen, peroxide, prostate-specific antigen, prothrombin, RNA, thyroid stimulating hormone, and troponin. Assays suitable for determining the concentration of DNA and/or RNA are disclosed in U.S. Pat. No. 6,281,006 and U.S. Pat. No. 6,638,716, the disclosures of each of which are incorporated by reference herein. Furthermore, the concentration of drugs, such as, for example, antibiotics (e.g., gentamicin, vancomycin, and the like), digitoxin, digoxin, drugs of abuse, theophylline, and warfarin, may also be determined.

Figure 2:
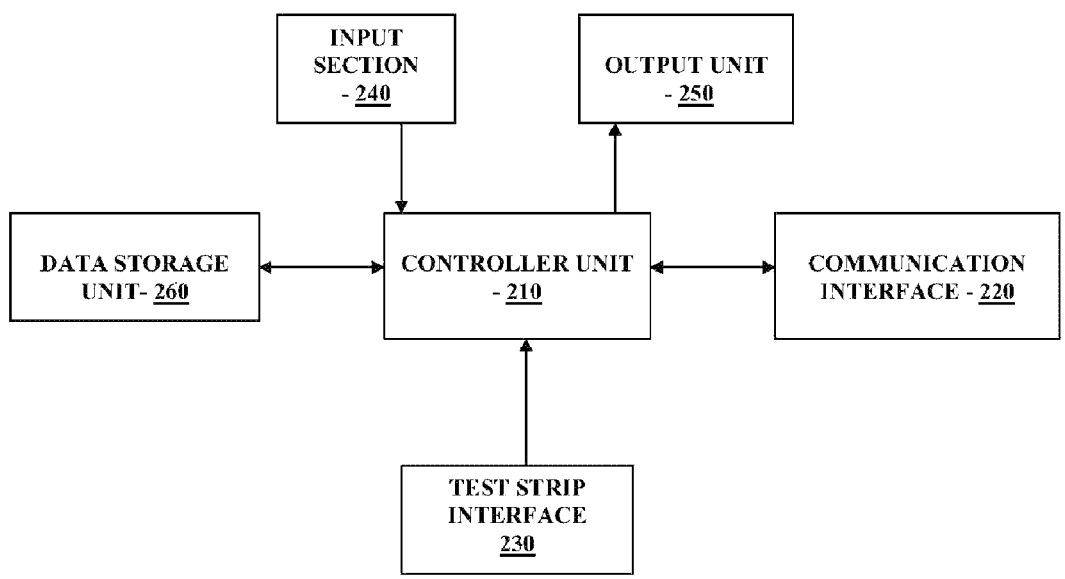
FIG. 2 is a block diagram of the health monitor device with a medication dose calculation function of FIG. 1 in one embodiment of the present disclosure.

FIG. 2 is a block diagram of the health monitor device with a medication dose calculation function of FIG. 1 in one embodiment of the present disclosure. Referring to FIG. 2, the health monitor device with a medication dose calculation function 100 (FIG. 1) includes a controller unit 210 operatively coupled to a communication interface 220 and configured for bidirectional communication. The controller unit 210 is further operatively coupled to a test strip interface 230, an input section 240 (which, for example, may include the input unit 140 and the plurality of input buttons 130 as shown in FIG. 1), an output unit 250, and a data storage unit 260.

Referring to FIG. 2, in one embodiment of the present disclosure, the test strip interface 230 is configured for signal communication with the inserted test strip 160 (FIG. 1) for determination of the fluid sample on the test strip 160. In addition, the test strip interface 230 may include an illumination segment which may be configured to illuminate the strip port 150 (FIG. 1) using a light emitting diode (LED), for example, during the test strip 160 insertion process to assist the user in properly and accurately inserting the test strip 160 into the strip port 150.

Moreover, in a further aspect of the present disclosure, the test strip interface 230 may be additionally configured with a physical latch or securement mechanism internally provided within the housing 110 of the health monitor device with a medication dose calculation function 100 (FIG. 1) such that when the test strip 160 is inserted into the strip port 150, the test strip 160 is retained in the received position within the strip port 150 until the sample analysis is completed. Examples of such physical latch or securement mechanism may include a uni-directionally biased anchor mechanism, or a pressure application mechanism to retain the test strip 160 in place by applying pressure on one or more surfaces of the test strip 160 within the strip port 150.

Referring back to FIG. 2 the output unit 250 may be configured to output display data or information including the determined analyte level on the display unit 120 (FIG. 1) of the health monitor device with a medication dose calculation function 100. In addition, in still a further aspect of the present disclosure, the output unit 250 and the input section 240 may be integrated, for example, in the case where the display unit 120 is configured as a touch sensitive display where the patient may enter information or commands via the display area using, for example, a finger or stylus or any other suitable input device, and where, the touch sensitive display is configured as the user interface in an icon or motion driven environment, for example.

Referring yet again to FIG. 2, the communication interface 220 in one embodiment of the present disclosure includes a wireless communication section configured for bi-directional radio frequency (RF) communication with other devices to transmit and/or receive data to and from the health monitor device with a medication dose calculation function 100. In addition, the communication interface 220 may also be configured to include physical ports or interfaces such as a USB port, an RS-232 port, or any other suitable electrical connection port to allow data communication between the health monitor device with a medication dose calculation function 100 and other external devices such as a computer terminal (for example, at a physician's office or in a hospital environment), an external medical device, such as an infusion device or including an insulin delivery device, or other devices that are configured for similar complementary data communication.

In one embodiment, the wireless communication section of the communication interface 220 may be configured for infrared communication, Bluetooth® communication, or any other suitable wireless communication mechanism to enable the health monitor device with a medication dose calculation function for communication with other devices such as infusion devices, analyte monitoring devices, computer terminals, communication enabled mobile telephones, personal digital assistants, or any other communication devices which the patient or user of the health monitor device with a medication dose calculation function 100 may use in conjunction therewith, in managing the treatment of a health condition, such as diabetes.

Figure 3:
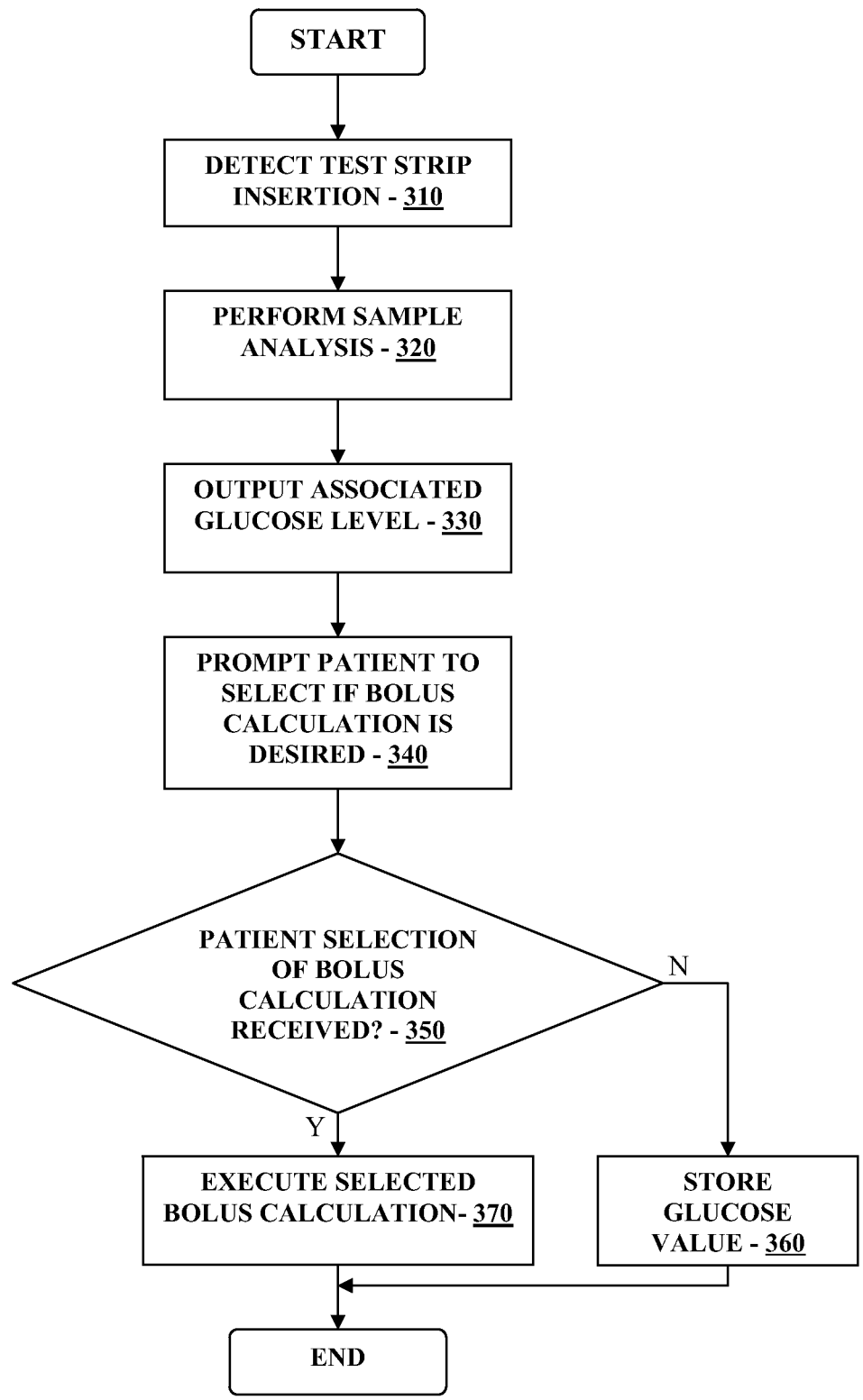
FIG. 3 is a flowchart illustrating the analyte level determination and medication dose calculation procedure in accordance with one embodiment of the present disclosure.

FIG. 3 is a flowchart illustrating the analyte level determination and medical dose calculation procedure in accordance with one embodiment of the present disclosure. Referring to FIG. 3, a test strip 160 is detected by the controller unit 210 (or the test strip interface 230) (310) of the health monitor device with a medication dose calculation function 100 (FIG. 1). Thereafter, the fluid sample, such as a blood sample, received from the inserted test strip 160 is analyzed (320) to determine the corresponding analyte level, such as a glucose level, and the determined analyte level is output (330) on the display unit 120 (FIG. 1) for example, in units of mg/dL.

Referring back to FIG. 3, after determining the analyte level and displaying the measured analyte level to the patient (330), a prompt command is generated and output to the patient to select if the medication dosage calculation is desired (340). More specifically, in one embodiment of the present disclosure, the controller unit 210 (FIG. 2) is configured to generate a command and display in the display unit 120 to query the user as to whether a medication dosage calculation determination is desired by the patient. Thereafter, a determination of whether or not the patient has selected to have the medication dosage calculation performed by the controller unit 210 is made (350). In one embodiment, the patient may operate one or more of the input buttons 130 or the input unit 140 to select whether or not to have the medication dosage calculation performed.

Referring again to FIG. 3, if it is determined that the patient has selected not to have the medication dosage determination performed, then the determined analyte value is displayed and/or stored (360), e.g., in memory of the health monitor device, and the routine terminates. For example, in one embodiment, the controller unit 210 (FIG. 2) may be configured to store the determined analyte value in the data storage unit 260 with associated time and/or date information of when the analyte value determination is performed. In an alternate embodiment, the measured analyte value may be stored substantially concurrently with the display of the analyte value.

On the other hand, if it is determined that the patient has selected to have the medication dosage calculation performed, the health monitor device with a medication dose calculation function 100 is configured to enter the medication dosage determination mode (370), described in further detail below in conjunction with FIG. 4, where the desired type of medication dosage is determined and provided to the patient. In another embodiment, the health monitor device with a medication dose calculation function 100 may be configured to store the glucose data even in the event the user selects to perform the medication dose calculation.

Figure 4:
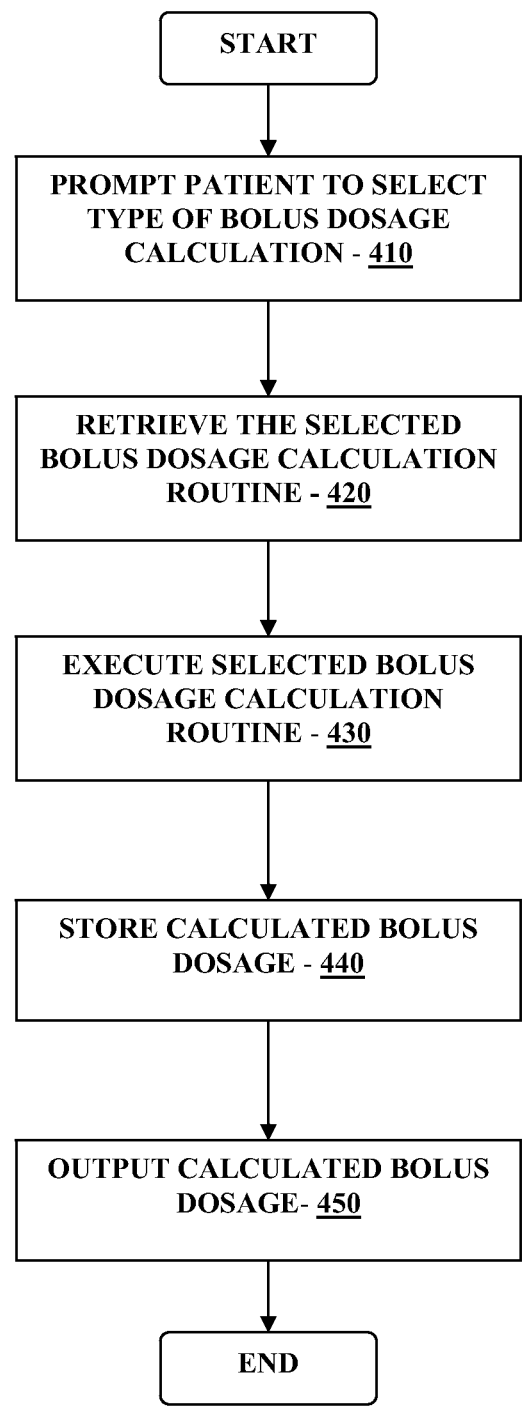
FIG. 4 is a flowchart illustrating the medication dose calculation procedure of FIG. 3 in accordance with one embodiment of the present disclosure.

FIG. 4 is a flowchart illustrating the medication dose calculation procedure of FIG. 3 in accordance with one embodiment of the present disclosure. Referring to FIG. 4, when the health monitor device with a medication dose calculation function 100 (FIG. 1) enters the medication dosage determination mode as described above, the controller unit 210 (FIG. 2) is configured to prompt the patient (for example, by displaying the options to the patient on the display unit 120 (FIG. 1)) to select the type of desired medication dosage calculation 410. For example, the controller unit 210 may be configured to output a list of available medication dosage calculation options including, for example, bolus calculation options such as a carbohydrate bolus, a correction bolus, a dual or extended bolus, a square wave bolus, or any other suitable medication calculation function which may be programmed into the health monitor device with a medication dose calculation function 100 (and for example, stored in the data storage unit 260).

Referring back to FIG. 4, after the patient selects the desired medication dosage calculation in response to the prompt for medication type selection (410), the selected medication dosage calculation routine is retrieved (420) from the data storage unit 260, and thereafter executed (430). In one embodiment, the execution of the selected medication dosage calculation (430) may include one or more input prompts to the patient to enter additional information as may be required to perform the selected medication dosage calculation.

For example, in the case of calculating a carbohydrate bolus, the patient may be prompted to provide or enter an estimate of the carbohydrate amount that the patient is planning on ingesting. In this regard, a food database may be stored in the data storage unit 260 or elsewhere for easy access (e.g., personal computers (PCs), personal digital assistants (PDAs), mobile telephones, or the like and to which the health monitor device may be coupled (e.g., wirelessly or by physical connection) to easily retrieve such information) to conveniently determine the corresponding carbohydrate amount associated with the type of food which the patient will be ingesting. Alternatively, the patient may provide the actual estimated carbohydrate count if such information is readily available by the patient.

Alternatively, in the case of calculating a dual bolus of insulin, the patient is prompted to provide, in addition to a dose amount, a time duration information for the extended portion of the bolus dosage to be infused or otherwise delivered to the patient. Similarly, the patient may further be prompted to provide insulin sensitivity information, and any other information as may be necessary to determine the selected bolus dosage amount in conjunction with other relevant information such as insulin on board information, and the time of the most recently administered bolus (so as to provide a warning to the patient if a bolus dosage has been administered within a predetermined time period, and a subsequent administration of the additional bolus dosage may potentially be harmful).

Referring back to FIG. 4, after the execution of the selected medication dosage calculation routine (430), the calculated medication dosage amount is stored (440) in the data storage unit 260, and the calculated medication dosage amount is output displayed to the patient (450) on the display unit 120 of the health monitor device with a medication dose calculation function 100, or audibly if the health monitor device is so configured. In certain embodiments, storing and output displaying the calculated medication dosage amount may be substantially concurrently performed, rather than sequentially.

Figure 5:
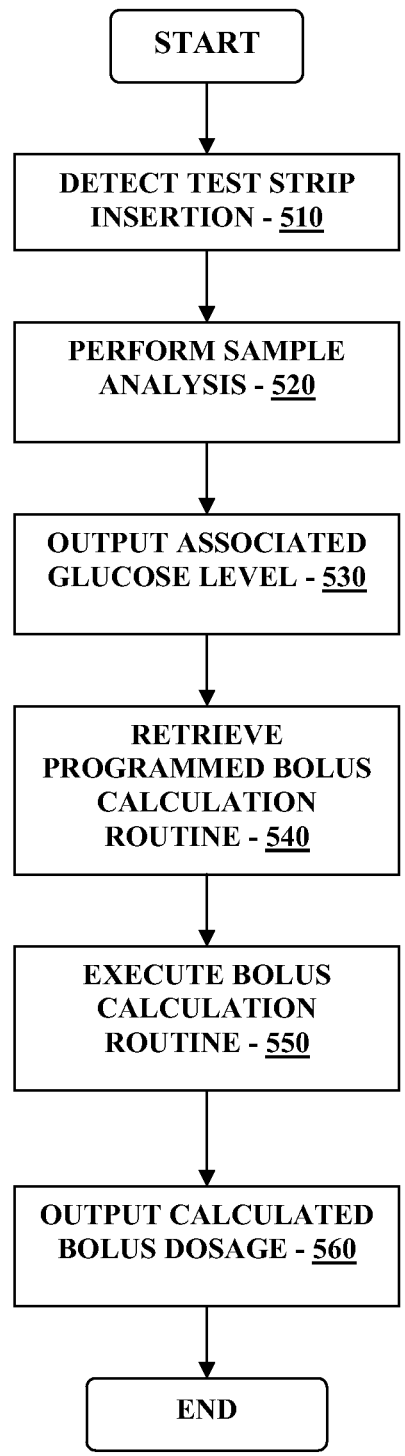
FIG. 5 is a flowchart illustrating the analyte level determination and medication dose calculation procedure in accordance with another embodiment of the present disclosure.

FIG. 5 is a flowchart illustrating the analyte level determination and medication dose calculation procedure in accordance with another embodiment of the present disclosure. Referring to FIG. 5, a test strip 160 is inserted into the strip port 150 of the health monitor device with a medication dose calculation function 100 and detected (510), the fluid sample on the test strip 160 is analyzed to determine the corresponding analyte level (520), and thereafter, output displayed (530).

Referring back to FIG. 5, after the analyte level from the fluid sample received from the test strip 160 is determined (530), a medication dosage calculation routine is retrieved (540). The controller unit 210 (FIG. 2) is configured to enter into the medication dosage determination mode, and to execute pre-programmed or predetermined medication calculation routine (550), and thereafter, output display the calculated medication dosage amount (560). In this manner, in one embodiment of the present disclosure, the health monitor device with a medication dose calculation function 100 may be programmed or configured to automatically enter into the medication determination mode upon completion of the fluid sample analysis for analyte level determination.

In one embodiment of the present disclosure, the health monitor device with a medication dose calculation function 100 may be configured to execute different types of medication dosage calculation based on the patient specified parameters. For example, the health monitor device with a medication dose calculation function 100 may be configured to perform a carbohydrate bolus determination when the test strip sample analysis is performed within a predetermined time period of a meal event. For example, the health monitor device with a medication dose calculation function 100 may be programmed by the patient to automatically select the carbohydrate bolus determination if the test strip fluid sample analysis is performed within one hour prior to a meal time (which may be programmed into the health monitor device with a medication dose calculation function 100).

Figure 6A:
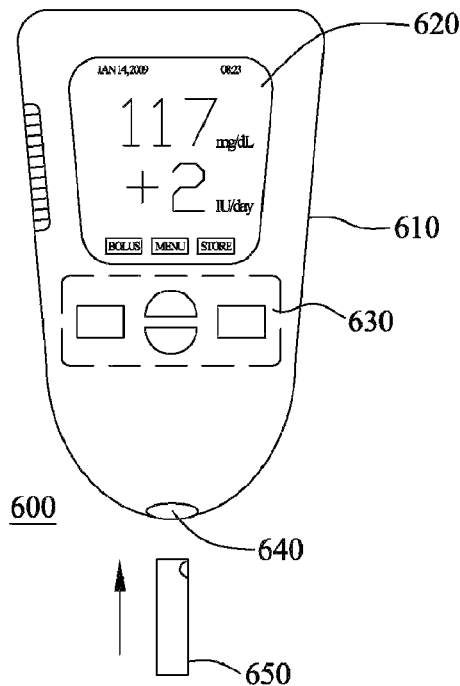
FIG. 6A shows a health monitor device with medication dose calculation function in accordance with another embodiment of the present disclosure.

FIG. 6A shows a health monitor device with medication dose calculation function in accordance with another embodiment of the present disclosure. A health monitor device 600 in accordance with one or more embodiments may be used for determining a concentration of an analyte in blood or interstitial fluid. In one embodiment, the health monitor device 600 may be an analyte test meter, such as a glucose test meter that may be used for determining an analyte concentration, such as a blood glucose concentration, of a sample for determination of a blood glucose level of a patient, such as a patient with Type-1 or Type-2 diabetes.

Referring to FIG. 6A, in one embodiment, the health monitor device 600 may be a small portable device designed to be palm-sized and/or adapted to fit into, for example, a pocket or purse of a patient. The portable health monitor device 600 may have the appearance of a personal electronic device, such as a mobile phone or personal digital assistant (PDA), so that the user may not be identified as a person using a medical device. Additional information is provided in U.S. Pat. No. 7,041,468 issued on May 9, 2006 titled "Blood Glucose Tracking Apparatus and Method" and in US Patent Application Publication No. US2004/0254434 published Dec. 16, 2004 titled "Glucose Measuring Module and Insulin Pump Combination", the disclosure of each of which is incorporated herein by reference for all purposes.

In another embodiment, the health monitor device 600 may be a larger unit for home use and designed to sit on a shelf or nightstand. In yet another embodiment, the health monitor device 600 may be designed for use in a hospital or doctor's office. The larger health monitor device units 600 may have the same functionality as the portable health monitor device 600 as described in further detail below.

Figure 6B:
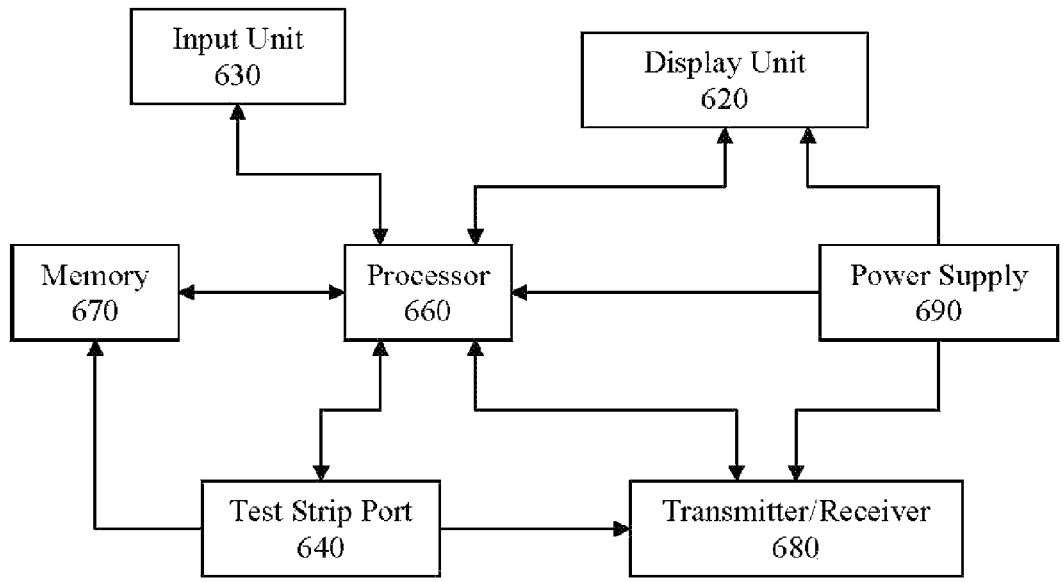
FIG. 6B is a block diagram of a configuration of the health monitor device shown in FIG. 6A in one embodiment.

Referring back to FIGS. 6A and 6B, a health monitor device 600 includes a housing 610 and a display unit 620 provided thereon. In one embodiment, the display unit 620 may be a dot-matrix display. In other embodiments, other display types, such as liquid-crystal displays (LCD), plasma displays, light-emitting diode (LED) displays, or seven-segment displays, among others, may alternatively be used. The display unit 620 may display, in numerical or graphical form, for example, information related to, among others, a patient's current analyte concentration. Also incorporated within the housing 610 of the health monitor device 600 may be a processor 660 (FIG. 6B) and a memory device 670 (FIG. 6B). The memory device 670 (FIG. 6B) may store raw and/or analyzed data as well as store instructions which, when executed by the processor 660 (FIG. 6B), may provide, among others, instructions to the display unit 620, and may be used for analysis functions, such as analyte concentration analysis and medication dosage calculations.

In embodiments of the present disclosure, the memory device 670 (FIG. 6B) may include a readable and/or writable memory device such as, for example, but not limited to a read only memory (ROM), random access memory (RAM), flash memory device, or static random access memory (SRAM). In another embodiment, an optional transmitter/receiver unit 680 (FIG. 6B) may be incorporated into the housing 610 of the health monitor device 600. The transmitter/receiver unit 680 (FIG. 6B) may be used to transmit and/or receive analyzed or raw data or instructions to/from, for example, optional peripheral devices, such as a data analysis unit or a medication administration unit in a data network.

In another embodiment, the transmitter/receiver unit 680 (FIG. 6B) is a transceiver capable of both transmitting and receiving data. The transmitter/receiver unit 680 (FIG. 6B) may be configured for wired or wireless transmission, including, but not limited to, radio frequency (RF) communication, RFID (radio frequency identification) communication, WiFi or Bluetooth® communication protocols, and cellular communication, such as code division multiple access (CDMA) or Global System for Mobile communications (GSM). In another embodiment, the health monitor device 600 may include a rechargeable power supply 690 (FIG. 6B), such as a rechargeable battery.

Referring back to FIG. 6A, in one embodiment, the health monitor device 600 may also include a plurality of input buttons 630. Each of the plurality of input buttons 630 may be designated for a specific task, or alternatively, each of the plurality of input buttons 630 may be 'soft buttons'. In the case that the plurality of input buttons are 'soft buttons', each of the plurality of buttons may be used for a variety of functions. The variety of functions may be determined based on the current mode of the health monitor device 600, and may be distinguishable to a user by the use of button instructions shown on the display unit 620. Other input methods may also be incorporated including, but not limited to, a touch-pad, jog-wheel, or capacitive sensing slider inputs. Yet another input method may be a touch-sensitive display unit, as described further below and shown in FIG. 7.

Referring back to FIG. 6A, the health monitor device 600 may also include a strip port 640 which may be configured for receiving a test strip 650. The test strip 650 is configured to receive a fluid sample, such as a blood sample, from a patient. The test strip 650 may then be inserted into the strip port 640, whereby the health monitor device 600 may analyze the sample and determine the concentration of an analyte, such as glucose, in the sample. The analyte concentration of the sample may then be displayed on the display unit 620 as the analyte level of the patient. In another aspect, the health monitor device 600 may use a conversion function to convert a measured analyte concentration of a sample to a blood analyte concentration of a host. In another embodiment, the analyte concentration of the analyzed sample may be stored in the memory 670 (FIG. 6B) of the health monitor device 600. The stored analyte concentration data may additionally be tagged with date and/or time data related to the date and/or time the fluid sample was taken and analyzed. In another embodiment, the analyte concentration data may be transmitted via the transmitter/receiver unit 680 (FIG. 6B) to one or more peripheral devices for storage and/or further analysis.

As discussed above, in certain embodiments, strip port to receive the test strip may be provided as a separate component that is configured to physically or electrically couple to the health monitoring device 600. Additional information is provided in U.S. Pat. No. 7,041,468 issued on May 9, 2006 titled "Blood Glucose Tracking Apparatus and Methods" and in US Patent Application Publication No. US2004/0254434 published Dec. 16, 2004 titled "Glucose Measuring Module and Insulin Pump Combination" the disclosures of each of which are incorporated herein by reference for all purposes.

In another embodiment, the health monitor device 600 may include instructions for calculating a medication dosage. The medication dosage may be, for example, a dosage of insulin in response to a blood glucose concentration data determined from the fluid sample on the test strip 650 received at the strip port 640. In one aspect, the medication dosage calculation may be based, at least in part, on a current patient analyte concentration data averaged with stored values of previous analyte concentration data.

In another aspect, the instructions for calculating a medication dosage may include instructions for calculating a dosage for a variety of types of medication, such as a variety of types of insulin. Insulin types may include, but are not limited to, long-acting insulin types such as LANTUS® (insulin glargine), available from Sanofi-Aventis, and LEVEMIR®, available from NovoNordisk, intermediate-acting insulin types such as Neutral Protamine Hagedorn (NPH), and LENTE insulin, fast-acting insulin types including recombinant human insulin such as HUMULIN®, available from Eli Lilly and Company, and NOVALIN®, available from NovoNordisk, bovine insulin, and porcine insulin, rapid-acting insulin types such as HUMALOG® (Lysine-Proline insulin), available from Eli Lilly and Company, APIDRA® (glulisine insulin), available from Sanofi-Aventis, and NOVOLOG® (aspart insulin), available from NovoNordisk, and very-rapid-acting insulin types such as VIAJECT™, available from Biodel, Inc.

In another embodiment, the instructions for calculating a medication dosage may be instructions for calculating a recommended update to an existing medication dosage regimen. Data related to a current medication dosage regimen may be stored in the memory 670 of the health monitor device 600, including current prescribed medication types and dosages and an algorithm for calculating recommended medication dosage changes. Calculated medication dosage recommendations may be displayed to the patient on the display unit 620 of the health monitor device 600 for patient intervention, or further may be transmitted directly to a medication administration device, such as an insulin pump, for a medication dosage regimen update.

In another embodiment, the health monitor device 600 may include programming for alarm functions. Alarms may be used to inform patients when current analyte concentrations are outside threshold levels, when medication dosage regimens need to be updated, or when an error is detected. Alarms may be in the form of a visual, auditory, or vibratory alarm.

In yet another embodiment, the health monitor device 600 may include an integrated medication delivery system (not shown). Additional information is provided in US Patent Publication No. US2006/0224141 published on Oct. 5, 2006, titled "Method and System for Providing Integrated Medication Infusion and Analyte Monitoring System", the disclosure of which is incorporated by reference for all purposes.

The integrated medication delivery system may be in the form of a drug delivery injection pen such as a pen-type injection device incorporated within the housing 610 of the health monitor device 600. Additional information is provided in U.S. Pat. Nos. 5,536,249 and 5,925,021, disclosure of each of which are incorporated herein by reference for all purposes.

The integrated medication delivery system may be used for injecting a dose of medication, such as insulin, into a patient based on a prescribed medication dosage, and may be automatically updated with dosage information received from the medication dosage calculator described above. In another embodiment, the medication dosage of the medication delivery system may include manual entry of dosage changes made through, for example, the input buttons 630 of the health monitor device 600. Medication dosage information associated with the medication delivery system may be displayed on the display unit 620 of the health monitor device 600.

Figure 6C:
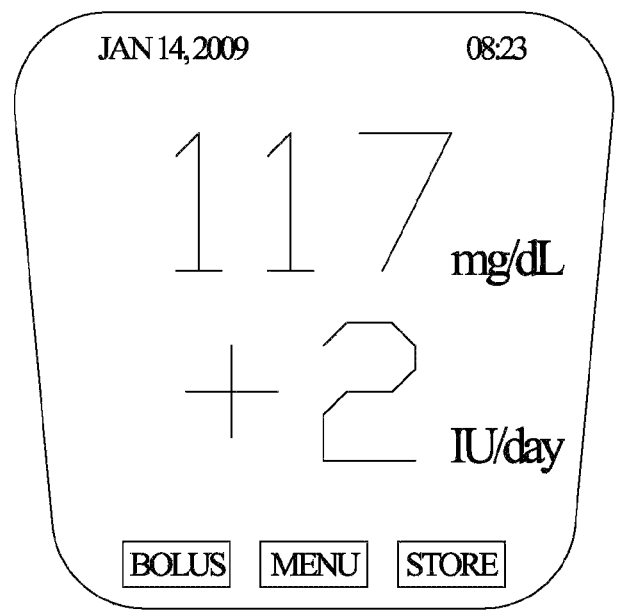
FIG. 6C is an illustration of a display of the health monitor device shown in FIG. 6A in one embodiment.

FIG. 6C is an illustration of a display of the health monitor device shown in FIG. 6A in one embodiment. Referring to FIG. 6C, the display unit 620 of the health monitor device 600 (FIG. 6A) may display a variety of data values to a patient. In one embodiment, the display unit 620 may display a current analyte concentration, such as the current blood glucose concentration of a patient, a recommended update to the patient's medication dosage regimen, such as insulin dosage updates, and the date and/or time of the current or most recent analyte test. Further, if the health monitor device 600 includes 'soft buttons', the display unit 620 may show the current function of said 'soft buttons' for the particular current operational mode of the health monitor device 600. Other information that may be displayed on the display unit 620 may include, but is not limited to, current medication dosage regimen data, recommended medication type, and historical patient analyte concentration data.

Information on the display unit 620 may be displayed in a variety of manners or format including, for example, numerical data, graphical data, symbols, pictures, and/or animations. In one aspect, the user may be able to choose the display style, for example, by pushing one of the input buttons 630. The display unit 620 may be a black and white display unit, or may alternatively be a color display unit, whereby, information may be displayed in a variety of colors. Colors may be used as indicators to a patient of changes in the current displayed information, or may be used for aesthetic purposes to allow for easier navigation of the data and/or menus. In another aspect, the brightness, contrast, tint, and/or color settings of the display unit 620 may be adjustable.

In another embodiment, the health monitor device 600 (FIG. 6) may incorporate a continuous analyte monitoring device, where a transcutaneously implanted sensor may continually or substantially continually measure an analyte concentration of a bodily fluid. Examples of such sensors and continuous analyte monitoring devices include systems and devices described in U.S. Pat. Nos. 6,175,752, 6,560,471, 5,262,305, 5,356,786, U.S. patent application Ser. No. 12/698,124 and U.S. provisional application No. 61/149,639 titled "Compact On-Body Physiological Monitoring Device and Methods Thereof", the disclosures of each of which are incorporated herein by reference for all purposes.

Accordingly, in certain embodiments, the health monitor device 600 may be configured to operate or function as a data receiver or controller to receive analyte related data from a transcutaneously positioned in vivo analyte sensor such as an implantable glucose sensor. The analyte monitoring system may include a sensor, for example an in vivo analyte sensor configured for continuous or substantially continuous measurement of an analyte level of a body fluid, a data processing unit (e.g., sensor electronics) connectable to the sensor, and the health monitor device 600 configured to communicate with the data processing unit via a communication link. In aspects of the present disclosure, the sensor and the data processing unit (sensor electronics) may be configured as a single integrated assembly. In certain embodiments, the integrated sensor and sensor electronics assembly may be configured as a compact, low profile on-body patch device assembled in a single integrated housing and positioned on a skin surface of the user or the patient with a portion of the analyte sensor maintained in fluid contact with a bodily fluid such as an interstitial fluid during the sensor life time period (for example, sensor life time period including about 5 days or more, or about 7 days or more, or about 14 days or more, or in certain embodiments, about 30 days or more). In such embodiments, the on-body patch device may be configured for, for example, RFID or RF communication with the health monitor device 600 to wirelessly provide monitored or detected analyte related data to the health monitor device 600 based on a predetermined transmission schedule or when requested from the health monitor device 600. Predetermined transmission schedule may be programmed or configured to coincide with the analyte sample detection by the analyte sensor (for example, but not limited to including once every minute, once every 5 minutes, once every 15 minutes). Alternatively, the health monitor device 600 may be programmed or programmable to acquire the sampled analyte data (real time information and/or stored historical data) in response to one or more requests transmitted from the health monitor device 600 to the on-body patch device.

As discussed, embodiments include the on-body patch device including the data processing unit coupleable to the analyte sensor so that both devices are positioned in or on the user's body, with at least a portion of the analyte sensor positioned transcutaneously. The data processing unit in certain embodiments may include a portion of the sensor (proximal section of the sensor in electrical communication with the data processing unit) which is encapsulated within or on the printed circuit board of the data processing unit with, for example, potting material or other protective material. The data processing unit performs data processing functions, where such functions may include but are not limited to, filtering and encoding of analyte related signals, for transmission to the health monitor device 600. In certain embodiments, the sensor or the data processing unit or a combined sensor/data processing unit may be wholly implantable under the skin layer of the user.

In certain embodiments, transmitter/receiver section 680 of the health monitor device 600 includes an RF receiver and an antenna that is configured to communicate with the data processing unit, and the processor 660 of the health monitor device 600 is configured for processing the received data from the data processing unit such as data decoding, error detection and correction, data clock generation, and/or data bit recovery.

In operation, the health monitor device 600 in certain embodiments is configured to synchronize with the data processing unit to uniquely identify the data processing unit, based on, for example, an identification information of the data processing unit, and thereafter, to periodically receive signals transmitted from the data processing unit associated with the monitored analyte levels detected by the sensor.

As described, in aspects of the present disclosure, the analyte monitoring system may include an on-body patch device with a thin profile that may be comfortably worn on the arm or other locations on the body (under clothing worn by the user or the patient, for example), the on-body patch device including an analyte sensor and circuitry and components for operating the sensor and processing and storing signals received from the sensor as well as for communication with the health monitor device 600. For example, one aspect of the on-body patch device may include electronics to sample the voltage signal received from the analyte sensor in fluid contact with the body fluid, and to process the sampled voltage signals into the corresponding glucose values and/or store the sampled voltage signal as raw data.

The on-body patch device in one aspect may further include an antenna such as a loop antenna to receive RF power from an external device such as the health monitor device 600 described above, electronics to convert the RF power received via the antenna into DC (direct current) power for the on-body patch device circuitry, communication module or electronics to detect commands received from the health monitor device 600, and communication component such as an RF transmitter to transmit data to the health monitor device 600, a low capacity battery for providing power to sensor sampling circuitry (for example, the analog front end circuitry of the on-body patch device in signal communication with the analyte sensor), one or more non-volatile memory or storage device to store data including raw signals from the sensor or processed data based on the raw sensor signals.

In certain embodiments, the health monitor device 600 may also be configured to operate as a data logger, interacting or communicating with the on-body patch device by, for example, periodically transmitting requests for analyte level information from the on-body patch device, and storing the received analyte level information from the on-body patch device in one or more memory components 670.

The various processes described above including the processes operating in the software application execution environment in the analyte monitoring system including the on-body patch device and/or the health monitor device 600 performing one or more routines described above may be embodied as computer programs developed using an object oriented language that allows the modeling of complex systems with modular objects to create abstractions that are representative of real world, physical objects and their interrelationships. The software required to carry out the inventive process, which may be stored in a memory or storage device of the storage unit of the various components of the analyte monitoring system described above in conjunction to the Figures including the on-body patch device or the health monitor device 600 may be developed by a person of ordinary skill in the art and may include one or more computer program products.

In one embodiment, an apparatus for bi-directional communication with an analyte monitoring system may comprise a storage device having stored therein one or more routines, a processing unit operatively coupled to the storage device and configured to retrieve the stored one or more routines for execution, a data transmission component operatively coupled to the processing unit and configured to transmit data based at least in part on the one or more routines executed by the processing unit, and a data reception component operatively coupled to the processing unit and configured to receive analyte related data from a remote location and to store the received analyte related data in the storage device for retransmission, wherein the data transmission component is programmed to transmit a query to a remote location, and further wherein the data reception component receives the analyte related data from the remote location in response to the transmitted query when one or more electronics in the remote location transitions from an inactive state to an active state upon detection of the query from the data transmission component.

Embodiments also include the on-body patch device including sensor electronics coupled to an analyte sensor is positioned on a skin surface of a patient or a user. In one aspect, an introducer mechanism may be provided for the transcutaneous placement of the analyte sensor such that when the on-body patch device is positioned on the skin surface, a portion of the sensor is inserted through the skin surface and in fluid contact with a body fluid of the patient or the user under the skin layer.

In certain embodiments, when the health monitor device 600 is positioned or placed in close proximity or within a predetermined range of the on-body patch device, the RF power supply in the health monitor device 600 may be configured to provide the necessary power to operate the electronics in the on-body patch device, and accordingly, the on-body patch device may be configured to, upon detection of the RF power from the health monitor device 600, perform preprogrammed routines including, for example, transmitting one or more signals to the health monitor device 600 indicative of the sampled analyte level measured by the analyte sensor. In one embodiment, communication and/or RF power transfer between the health monitor device 600 and the on-body patch device may be automatically initiated when the health monitor device 600 is placed in close proximity to the on-body patch device. Alternatively, the health monitor device 600 may be configured such that user intervention, such as a confirmation request and subsequent confirmation by the user using, for example, the display 620 and/or input components 630 of the health monitor device 600, may be required prior to the initiation of communication and/or RF power transfer between the health monitor device 600 and the on-body patch device. In a further embodiment, the health monitor device 600 may be user configurable between multiple modes, such that the user may choose whether the communication between the health monitor device 600 and on-body patch device is performed automatically or requires a user confirmation.

As discussed, some or all of the electronics in the on-body patch device in one embodiment may be configured to rely on the RF power received from the health monitor device 600 to perform analyte data processing and/or transmission of the processed analyte information to the health monitor device 600. That is, the on-body patch device may be discreetly worn on the body of the user or the patient, and under clothing, for example, and when desired, by positioning the health monitor device 600 within a predetermined distance from the on-body patch device, real time glucose level information may be received by the health monitor device 600. This routine may be repeated as desired by the patient (or on-demand or upon request, for example) to acquire monitored real time glucose levels at any time during the time period that the on-body patch device is worn by the user or the patient.

In another embodiment, the health monitor device 600 may include an integrated analyte test meter and lancing device for lancing a bodily fluid sample, such as a blood sample, and measuring an analyte concentration, such as a blood glucose concentration. Examples of such integrated devices include systems and devices described in US Published Application Nos. 2007/0149897 and 2008/0167578, the disclosures of each of which are incorporated herein by reference for all purposes.

Figure 7:
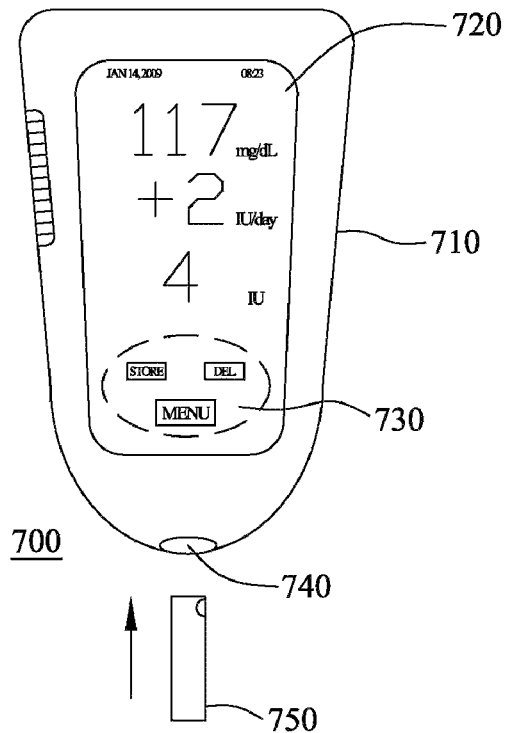
FIG. 7 shows a touch-screen health monitor device in accordance with one embodiment of the present disclosure.

FIG. 7 shows a touch-screen health monitor device in accordance with one embodiment of the present disclosure. Referring to FIGS. 7 and 6A, a touch-screen health monitor device 700 may include the same functions and basic design as a health monitor device 600 without a touch-screen. Typically, a touch-screen health monitor device 700 would include a larger display unit 720 compared to the display unit 620 of a health monitor device 600 without a touch-screen in order to accommodate the extra area required for any touch-screen buttons 730 that may be used. Similar to a health monitor device 600 without a touch-screen, a touch-screen health monitor device 700 includes a housing 710, thereon which lies the touch-screen display unit 720. The touch-screen health monitor device 700 may also include a strip port 740 for receiving a test strip 750, which may include a fluid sample for analysis, such as a blood sample for a blood glucose concentration analysis.

Figure 8:
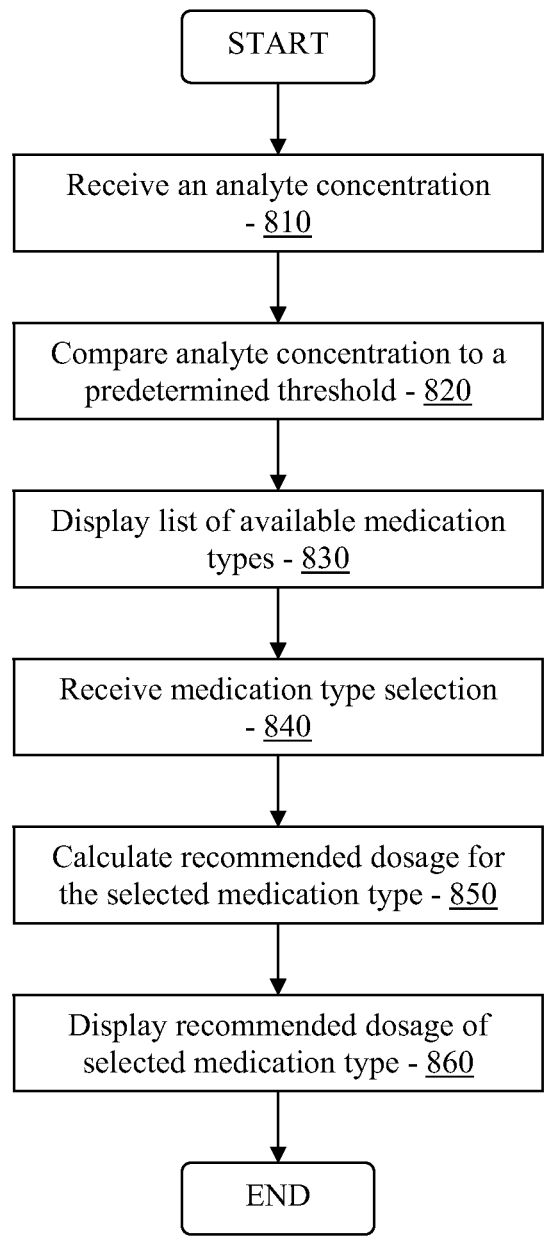
FIG. 8 is a flow chart illustrating a medication dosage calculation procedure for use in one or more embodiments of the present disclosure.

FIG. 8 is a flow chart illustrating a medication dosage calculation procedure for use in one or more embodiments of the present disclosure. Referring to FIG. 8, a device, such as a health monitor device 600 (FIG. 6A), receives an analyte concentration (810) for the current analyte level of a patient. The analyte level is compared to a predetermined threshold analyte level (820). For example, if the analyte is glucose and the analyte level is a blood glucose level of a patient, the threshold blood glucose level may be between 80 mg/dL and 120 mg/dL, or a tailored threshold determined by a healthcare professional. If the current analyte concentration level is above the predetermined threshold, a list of available medication types may be displayed (830) on the display unit 620 of a health monitor device 600. For example, if the analyte concentration level is a blood glucose concentration level for a patient suffering from, for example, diabetes, the list of available medication types may be a list of available insulin types. From the list of available medication types, a medication type is selected (840) and a recommended dosage for the selected medication type based upon the current analyte concentration level is calculated (850) and displayed (860).

Figure 9:
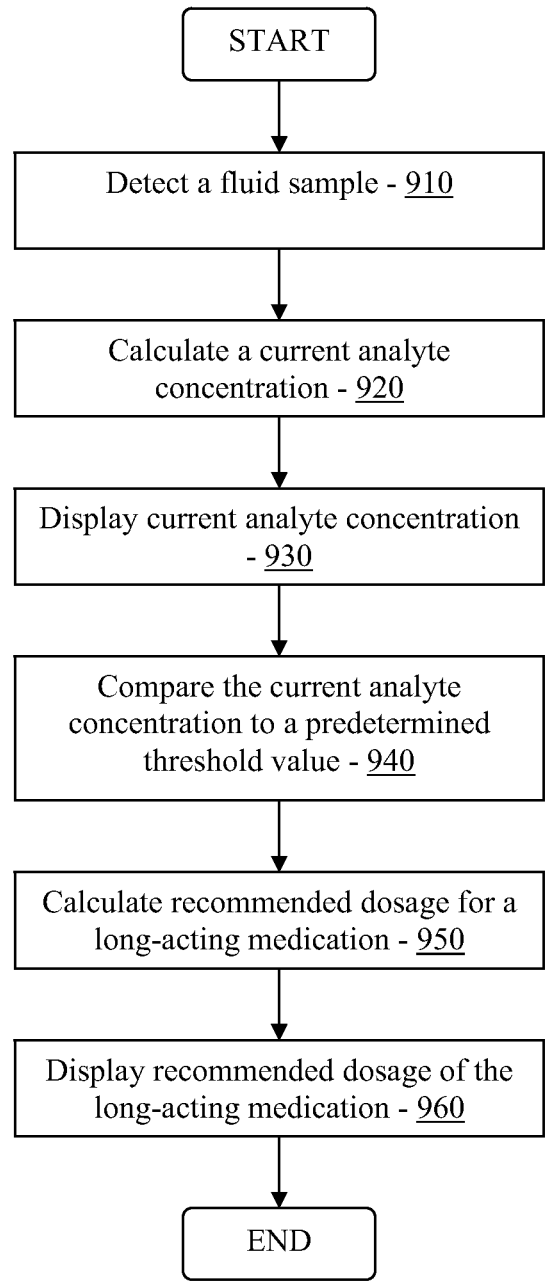
FIG. 9 is a flow chart illustrating an analyte concentration determination and medication dosage calculation in one embodiment of the present disclosure.

FIG. 9 is a flow chart illustrating an analyte concentration determination and medication dosage calculation in one embodiment of the present disclosure. Referring to FIGS. 9 and 6A, a fluid sample is detected (910), for example, by applying the fluid sample to a test strip 650 and inserting the test strip 650 into a strip port 640 of the health monitor device 600. Upon detection of the fluid sample, a current analyte concentration is calculated (920) based on analysis of the fluid sample. In one embodiment, the health monitor device 600 may include a display unit 620, such as a dot-matrix display, and the current analyte concentration is displayed (930) on the display unit 620.

Still referring to FIGS. 9 and 6A, in one embodiment, the health monitor device 600 may include instructions or routines to perform a long-acting medication dosage calculation function. A long-acting medication may be a medication wherein a single dose may last for up to 12 hours, 24 hours, or longer. The instructions for a long-acting medication dosage calculation function may be in the form of software stored on the memory device 670 (FIG. 6B) and executed by the processor 660 (FIG. 6B) of the health monitor device 600. In one aspect, the long-acting medication dosage calculation function may be an algorithm based on the current concentration of an analyte of a patient, wherein the long-acting medication dosage calculation function compares the current analyte concentration value to a predetermined threshold (940), which may be based on clinically determined threshold levels for a particular analyte, or may be tailored for individual patients by a doctor or other treating professional. If the current analyte concentration is above the predetermined threshold, the long-acting medication dosage calculation function may use the current analyte concentration value to calculate a recommended dosage of a long-acting medication (950). Once calculated, the recommended medication dosage may be displayed (960) on the display unit 620 of the health monitor device 600.

In one embodiment, the health monitor device 600 may be configured to measure the blood glucose concentration of a patient and include instructions for a long-acting insulin dosage calculation function. Periodic injection or administration of long-acting insulin may be used to maintain a baseline blood glucose concentration in a patient with Type-1 or Type-2 diabetes. In one aspect, the long-acting medication dosage calculation function may include an algorithm or routine based on the current blood glucose concentration of a diabetic patient, to compare the current measured blood glucose concentration value to a predetermined threshold or an individually tailored threshold as determined by a doctor or other treating professional to determine the appropriate dosage level for maintaining the baseline glucose level.

In one embodiment, the long-acting insulin dosage calculation function may be based upon LANTUS® insulin, available from Sanofi-Aventis, also known as insulin glargine. LANTUS® is a long-acting insulin that has up to a 24 hour duration of action. Further information of LANTUS® insulin is available at www.lantus.com. Other types of long-acting insulin include LEVEMIR® insulin available from NovoNordisk (www.levemir-us.com).

Figure 10:
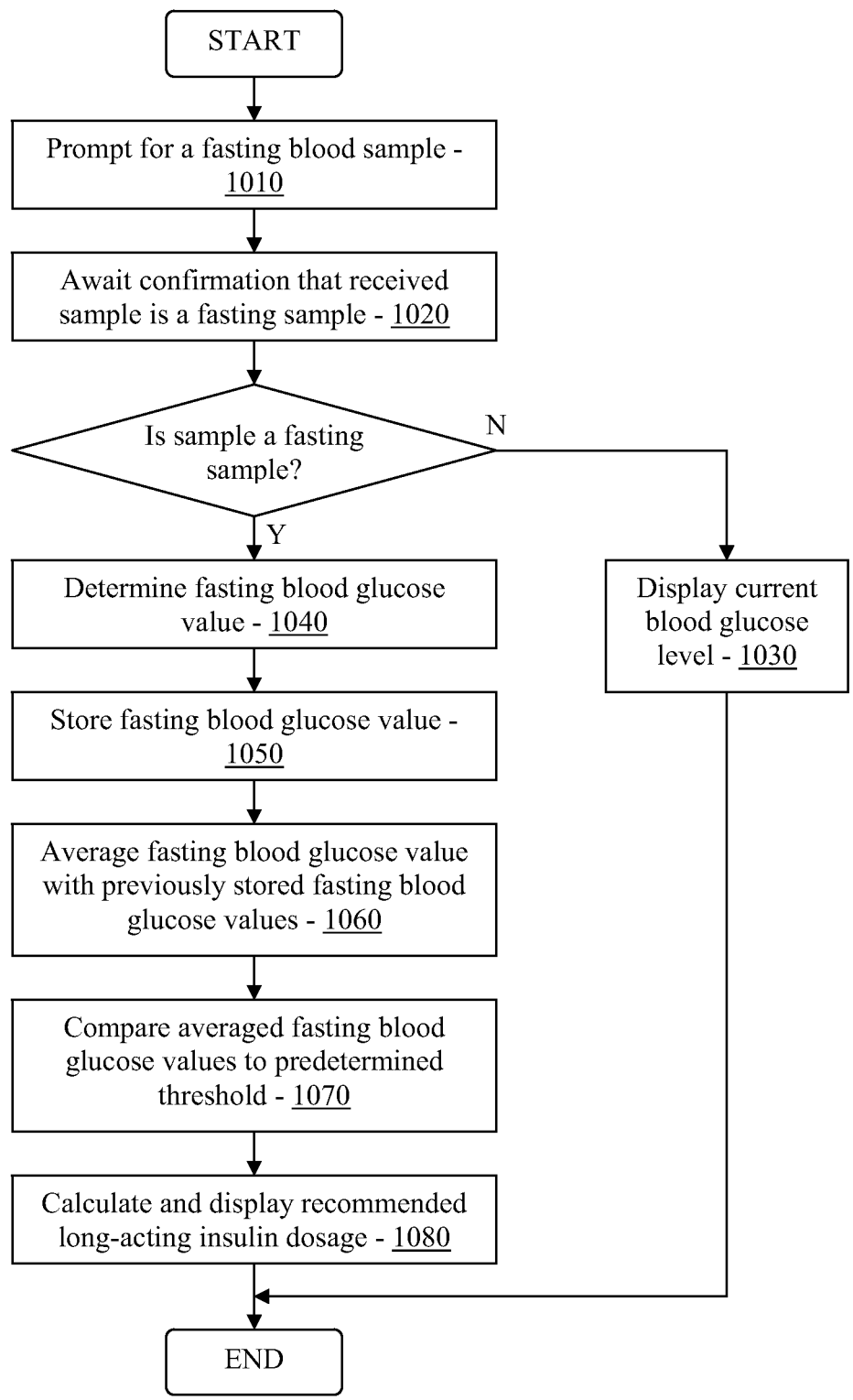
FIG. 10 is a flow chart illustrating a procedure for determining a recommended update to a long-acting insulin dosage regimen in one embodiment.

FIG. 10 is a flow chart illustrating a procedure for determining a recommended update to a long-acting insulin dosage regimen in one embodiment. Some patients with diabetes, including patients with type-1 diabetes and patients with type-2 diabetes, may require or be recommended to take insulin as a method for maintaining a safe blood glucose level. In some cases, a medical professional may determine that a dosage regimen of long-acting insulin, such as LANTUS® insulin, may be beneficial to a patient for maintaining a safe baseline blood glucose level. Long-acting insulin may be taken as, for example, a daily bolus dosage, and may have up to a 24 hour duration of action. Long-acting insulin may be used as an alternative for patients who may not wish to use an insulin pump, which provides a patient with a steady basal glucose level throughout the day. In some cases, a patient may require only the long-acting insulin dose to maintain a safe baseline blood glucose level, and may not require periodic doses of a fast or rapid acting insulin to correct for spikes in blood glucose levels resulting from, for example, carbohydrate intake. In one embodiment, among others, long-acting insulin may be taken as an injection by, for example, a syringe or injection pen, as an oral stimulant from, for example, an inhaler, or as a transdermal patch delivery system.

Patients using long-acting insulin may have different sensitivity to insulin. As such, it may be desirable for patients to periodically adjust their daily bolus dosage of long-acting insulin. Referring to FIG. 10, a glucose measuring device, such as the health monitor device 600 described above in conjunction with FIG. 6A, may prompt for a fasting blood sample (1010) to measure a fasting blood glucose level. A fasting blood sample may be a blood sample of a patient taken after a predetermined period of time without food, such as 8 hours without food typically obtained in the morning after a period of sleep. The fasting blood sample may be received on a test strip 650, which may be inserted into a strip port 640 of the health monitor device 600 for analysis.

Referring back to FIG. 10, in one embodiment, to ensure an accurate blood glucose reading, the health monitor device 600 may request and await confirmation that the provided blood sample is a fasting sample (1020). The confirmation that the provided blood sample is a fasting sample may be provided by the patient to the health monitor device 600 through, for example, the input buttons 630 of the health monitor device 600. Alternatively, the health monitor device 600 may determine whether the provided blood sample is a fasting sample by determining if the current time is in the morning following what would typically be a predetermined period of sleep, or comparing the current time to stored past data and basing whether the sample is a fasting sample or not based upon trends of what time during the day that previous provided fasting samples were obtained. In the event that the provided blood sample is not a fasting sample, the health monitor device 600 may calculate and display the current blood glucose level of the provided sample with a warning that the displayed value is not a fasting blood glucose level (1030). In one aspect, if the provided blood sample is not a fasting sample, no recommended long-acting insulin dosage regimen update is calculated or displayed.

Still referring to FIG. 10, if the received blood sample is confirmed to be a fasting blood sample, a fasting blood glucose level may be determined by analyzing the blood glucose level of the received blood sample (1040). Once the fasting blood glucose level is determined, the value may be stored (1050) in a memory 670 of the health monitor device 600, or alternatively, the value may be transmitted for storage in a memory of a secondary device or computer. In one embodiment, the stored fasting blood glucose level data may be time and/or date stamped. Once the fasting blood glucose level data is stored in the memory 670, the data may be compared to a predetermined threshold value. In another embodiment, the current fasting blood glucose level may be averaged with stored fasting blood glucose level data from preceding days (1060), for example, the preceding, one, two, or four days, for comparison to the predetermined threshold value (1070).

If the current fasting blood glucose level or the averaged fasting blood glucose level are above the predetermined threshold, a dosage recommendation algorithm may be implemented based on the fasting blood glucose level. The dosage recommendation algorithm may be stored in the memory 670 in the health monitor device 600 and executed by the processor 660 in the health monitor device 600, to calculate and display on a display unit 620 a recommended long-acting insulin dosage (1080). Alternatively, the dosage recommendation algorithm may be stored in a peripheral device containing a memory, and data may be transmitted to one or more peripheral devices over a data network for analysis and the results transmitted back to the health monitor device 600 for display.

The severity of the symptoms of diabetes for patients may vary from individual to individual. For some diabetic patients, it may be advantageous to use insulin to maintain a stable baseline blood glucose level, and additionally to use fast-acting insulin injections to compensate for periodic blood glucose level fluctuations resulting from, for example, carbohydrate intake. For such patients, it may be advantageous to have a method of calculating adjustments to daily insulin dosages to maintain a safe baseline blood glucose level, as well as on-the-spot dosage recommendations to correct for periodic blood glucose level fluctuations.

Insulin used to maintain a stable baseline blood glucose level may be administered through, among others, the use of an insulin pump in the form of a basal insulin infusion (small dosages of insulin injected into the body at periodic intervals throughout the day), or may be administered through the use of single daily injections of long-acting insulin, such as LANTUS® insulin. In other embodiments, long-acting insulin may be administered at various other intervals, such as twice a day, or every other day. Fast-acting and rapid-acting insulin, for example, are more often used as single dose bolus injections for immediate correction to periodic blood glucose level fluctuations, which may be used in conjunction with the long-acting insulin used to maintain the baseline blood glucose level. Accurate calculation and administration of insulin to a diabetic patient is used as a measure for maintaining safe blood glucose levels in order to avoid incidents of hyperglycemia.

Figure 11:
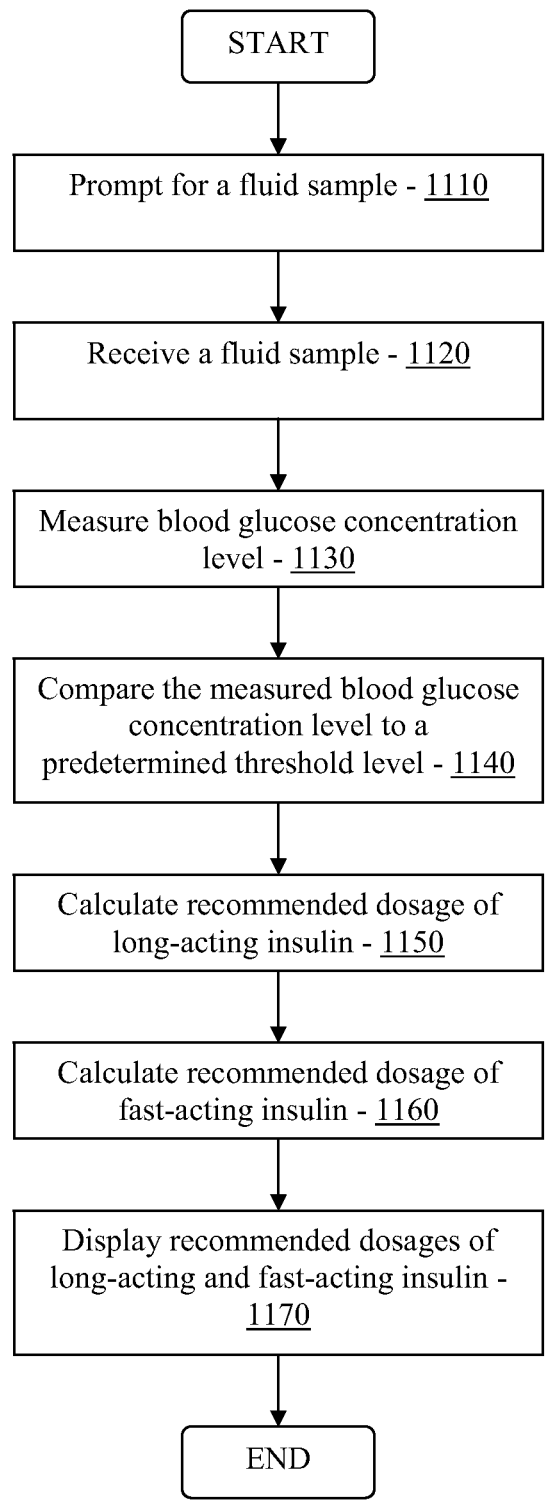
FIG. 11 is a flow chart illustrating a procedure for calculating a dosage recommendation for a long-acting insulin and a fast-acting insulin in one embodiment.

FIG. 11 is a flow chart illustrating a procedure for calculating a dosage recommendation for a long-acting insulin and a fast-acting insulin in one embodiment. Typically, long-acting insulin dosage regimens are calculated and adjusted based upon a patient's fasting blood glucose level, or the blood glucose level of a patient after a predetermined length of time, such as 8 hours, without food (or after 8 hours of sleep). The fasting glucose level may be considered to be the baseline glucose level of a patient, and is further used for determining a long-acting insulin dosage calculation, which is typically used for controlling the baseline glucose level of a patient. On the other hand, fast-acting insulin bolus dosages are typically calculated based upon a current or future blood glucose level regardless of activities such as eating and exercise, as fast-acting insulin bolus dosages are typically used to correct a current on-the-spot blood glucose level fluctuation.

Referring to FIG. 11, a glucose measuring device, such as the health monitor device 600 described above in conjunction with FIG. 6A, may prompt for a fluid sample (1110) to measure a blood glucose level. The fluid sample may be received (1120) at a strip port 640 of the health monitor device 600 in the form of a blood sample applied to a test strip 650. The received sample may then be analyzed in order to measure a blood glucose concentration level (1130). The measured blood glucose concentration level may then be compared to a predetermined threshold level (1140) for determination of whether an insulin dosage may be required in order to adjust the blood glucose concentration level to a safe or optimal level.

In the case that an insulin dosage is determined to be required or recommended, the health monitor device 600 may calculate a recommended dosage of long-acting insulin (1150) as well as a recommended dosage of a fast-acting insulin (1160). The dosages may be calculated based upon one or more software algorithms stored within a memory unit 670 and executed by the processor 660 of the health monitor device 600. Once calculated, the recommended dosages of long-acting and fast-acting may be displayed on a display unit 620 of the health monitor device 600 (1170).

In one embodiment, the health monitor device 600 may only recommend a long-acting insulin dosage when the received blood sample is a fasting blood sample. In another embodiment, the health monitor device 600 may determine whether to recommend a long-acting insulin dosage or a fast-acting insulin dosage or both, based upon the current time of day, whereby the time of day consideration may be determined by analyzing trends of previous data stored in the memory 670 of the health monitor device 600.

It is to be understood that the procedures described above in conjunction with FIG. 11 are not limited to only the calculation of a long-acting insulin and a fast-acting insulin, but may be applicable to any combination of one or more medications used to treat a number of physiological conditions, including, among others, various analyte concentrations, heart-rate, breathing rate, or blood pressure, whereby some or all of the medications may be configured for dosage updates based upon a variety of mitigating factors, such as carbohydrate intake or physical activity.

Figure 12:
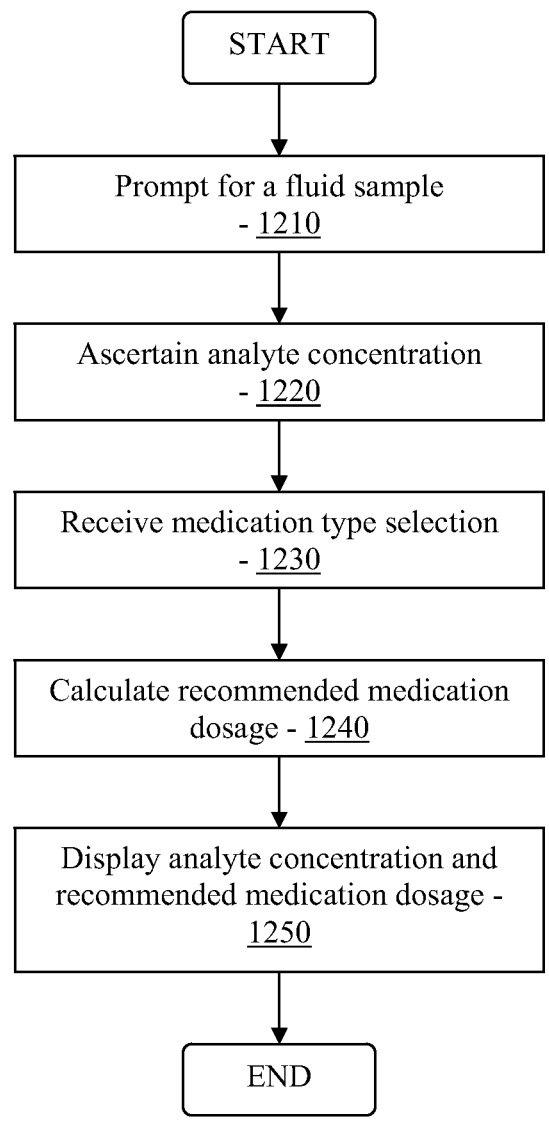
FIG. 12 is a flow chart illustrating a means for calculating a dosage recommendation for one or more selectable medication types.

In one embodiment, a health monitor device 600 (FIG. 6A) with a medication dosage calculator may include a medication type selector function. The medication type selector function may allow a patient to request a recommended dosage for a variety of medication types. FIG. 12 is a flow chart illustrating a means for calculating a dosage recommendation for one or more selectable medication types. Referring to FIG. 12, a health monitor device 600 may prompt for a fluid sample (1210) and subsequently analyze the fluid sample to ascertain an analyte concentration (1220). In one embodiment, the health monitor device 600 may be a blood glucose measuring device, and may receive a fluid sample in the form of a blood sample applied to a test strip 650 and inserted into a strip port 640 of the health monitor device 600. The blood sample may be analyzed to discern a blood glucose concentration, which may be used as an indicator for the blood glucose level of a patient from which the sample was obtained.

Once an analyte concentration is ascertained, a medication type selection is received (1230). The medication type selection may be established via a number of different methods, including providing a list of available medication types for which the health monitor device 600 is programmed to calculate dosage information. For example, if the health monitor device 600 is a glucose measuring device intended for the measurement of a patient's blood glucose level, the corresponding medication for dosage calculation may be insulin. In this case, the glucose measuring device may include programming or algorithms for calculating insulin dosage information for a variety of insulin types, including long-acting insulin, intermediate acting insulin, fast-acting insulin, rapid-acting insulin, and very-rapid acting insulin. Further, programming or algorithms may be exclusive to specific insulin compositions, even amongst the general categories of insulin types. In another aspect, the medication type may be selected automatically by the health monitor device 600 based on, for example, a pre-programmed treatment regimen.

Referring back to FIG. 12, once a medication type is chosen, the program or algorithm associated with the selected medication type may be applied to the ascertained analyte concentration in order to calculate a recommended medication dosage (1240). The recommended medication dosage and the ascertained analyte concentration may then be displayed on a display unit 620 of the health monitor device 600 (1250). In another embodiment, the selected medication type may also be displayed on the display unit 620 to allow for confirmation that the recommended medication dosage is meant for the correct medication type.

In another embodiment, a list of available medication types for display and for selection may be limited to a predetermined list of available medications as indicated by the user, or alternatively by a doctor or other treating professional. In this manner, in one aspect of the present disclosure, a list or subset of available medication types for selection (and subsequent dosage calculation, for example) may be limited to a predetermined list of available (or pre-stored) or permitted medication stored in the health monitor device 600. The list of available or permitted medication may be stored in the memory 670 of the health monitor device 600. Alternatively, the health monitor device 600 may include programming or software instructions which, when a particular medication is selected, other medication known or determined to be incompatible with the selected medication (for example, due to potential adverse reactions when mixed with the selected medication), may automatically be removed from the list of available medication types before providing the list to the user of the health monitor device 600.

In another embodiment, the memory 670 of the health monitor device 600 may store information related to a patient's medical history, for example, information related to medications the patient has been previously determined to cause allergic or undesirable reactions. Accordingly, the memory 670 may store, for example, a dynamic list of available medications that are appropriate for the medication dose determination in response to or based on a selection of a type of the medication selected for dosage calculation, or alternatively, based on one or more other characteristics based on the physiological condition of the user or the medication composition.

In some instances, it may be advantageous for a patient to make use of more than one medication to control a disease or health condition. For example, diabetic patients, including patients with Type-1 and severe Type-2 diabetes, may benefit from using more than one type of insulin to help control their blood glucose level. For example, it may be advantageous to use long-acting insulin to maintain a stable baseline blood glucose level, and additionally to use fast-acting insulin injections to compensate for periodic blood glucose level fluctuations resulting from, for example, carbohydrate intake. Accordingly, in one aspect there is provided techniques for calculating adjustments to daily insulin dosages to maintain a safe baseline blood glucose level, as well as on-the-spot dosage recommendations to correct for periodic blood glucose level fluctuations.

Figure 13:
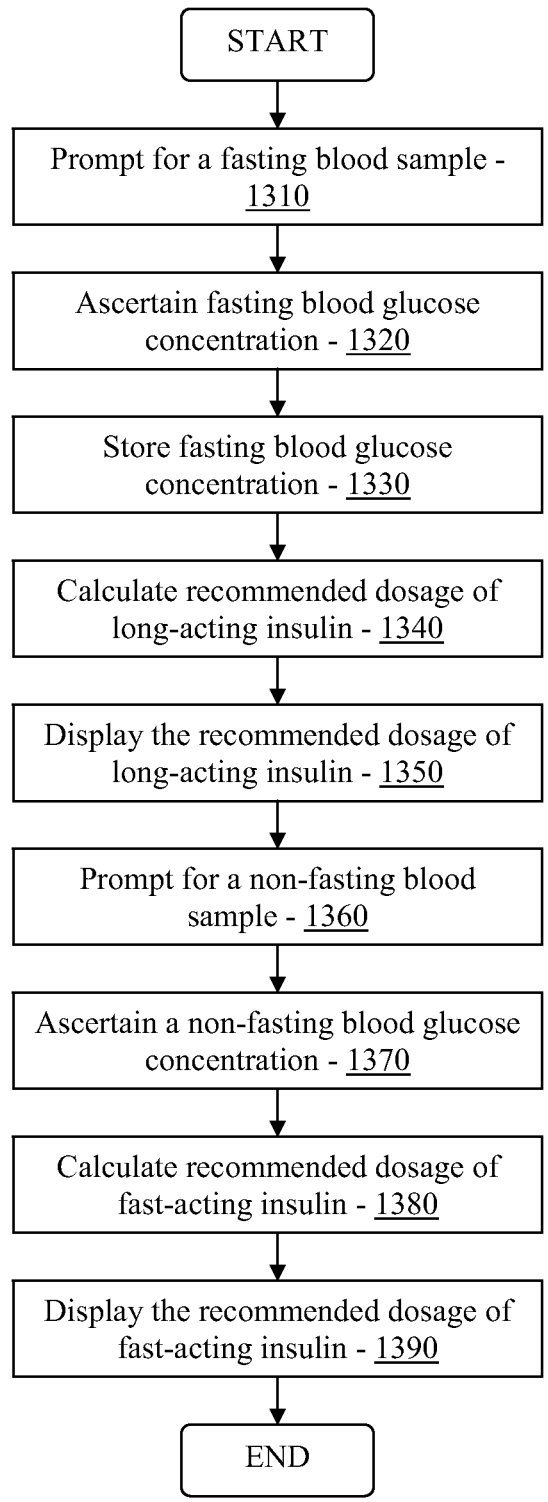
FIG. 13 is a flow chart illustrating a means for calculating insulin dosage information for more than one type of insulin in another embodiment.

FIG. 13 is a flow chart illustrating a means for calculating insulin dosage information for more than one type of insulin. In one embodiment, the more than one type of insulin may include a combination of a long-acting insulin and a rapid-acting insulin. In one aspect, dosages of the long-acting insulin may be calculated based upon a fasting blood glucose level of a patient. Referring to FIG. 13, a health monitor device 600 (FIG. 6A) may prompt for a fasting blood sample (1310). The fasting blood sample may be a blood sample taken from a patient after a predetermined length of time, such as at least 8 hours, without food and applied to a test strip 650 to be inserted into a strip port 640 of the health monitor device 600 for analysis. As a fasting blood sample is taken after at least 8 hours without food, often the blood sample is taken in the morning following 8 hours of sleep. In one aspect, in order to discern a consistent fasting blood glucose level, the health monitor device 600 may prompt for the fasting blood sample at the same time every morning. Once the fasting blood sample is received by the health monitor device 600, the sample may then be analyzed in order to ascertain a blood glucose concentration (1320) of the patient from which the sample was obtained. Once ascertained, the blood glucose concentration may be stored (1330) in a memory 670 of the health monitor device 600. In one aspect, the stored blood glucose concentration may be date and/or time stamped. An algorithm for calculating a long-acting insulin dosage recommendation may then be applied to the ascertained blood glucose concentration in order to calculate a recommended long-acting insulin dosage (1340) to be displayed on a display unit 620 of the health monitor device 600 (1350).

The algorithm or routine for determining a long-acting insulin dosage recommendation may be a dosage update algorithm based upon initial settings as determined by, for example, a healthcare professional or an insulin manufacturer specification. In one embodiment, an initial daily prescribed dosage of long-acting insulin, such as LANTUS® insulin (which has up to a 24 hour active time), may be 10 IU (International Unit) of insulin per day. One International Unit (IU) of insulin is the biological equivalent of 45.5 micrograms (µg) of pure crystalline insulin. 10 IU/day of LANTUS® insulin may be the starting dosage of a long-acting insulin regimen. The fasting blood glucose concentration may be measured on a daily basis, and each measurement stored in a memory. By taking a mean average of the stored fasting blood glucose concentrations, the fasting blood glucose concentration average may be compared to a predetermined target fasting blood glucose concentration threshold. In one aspect, a recommended update to the daily dosage of long acting insulin may be calculated weekly, based upon the average glucose concentration of the preceding two or more days, and follow the below dosage schedule:

| Average Glucose Concentration | Increase in Insulin Dose(IU/day) |
|---|---|
| ≥180 mg/dL | +8 |
| 140-179 mg/dL | +6 |
| 120-139 mg/dL | +4 |
| 100-119 mg/dL | +2 |

In another embodiment, the algorithm for calculating a long-acting insulin dosage recommendation may be a daily dosage update. The algorithm may compare a fasting blood glucose concentration to a predetermined threshold level, for example, a target threshold level as determined by a healthcare professional. If the fasting blood glucose concentration is greater than the target threshold level, the algorithm may recommend an increase of 1 IU/day of long-acting insulin. This may continue each day until the fasting blood glucose concentration is at or below the target threshold level.

In other embodiments, the target threshold level of fasting blood glucose concentration may be set by the user or may be a customized target threshold as determined by a healthcare professional.

In another embodiment, the algorithm for calculating a long-acting insulin dosage recommendation may be based on both an upper and lower threshold value. For example, a healthcare professional may recommend a safe fasting blood glucose concentration between a predefined range. In such a case, the algorithm may update the long-acting insulin dosage on a daily basis. In one aspect, if the fasting blood glucose concentration is greater than the upper threshold, the algorithm may recommend an increase to the current long-acting insulin dosage by 1 IU/day, while if the fasting blood glucose concentration is less than the lower threshold, the algorithm may recommend a decrease to the current long-acting insulin dosage by 1 IU/day. Furthermore, if the fasting blood glucose concentration is between the upper and lower threshold, the algorithm may recommend no change to the current long-acting insulin dosage regimen.

In another embodiment, the algorithm for calculating a long-acting insulin dosage recommendation may be based upon past and present fasting blood glucose concentration values. In one aspect, the algorithm may not recommend an update to a current glucose dosage unless the fasting blood glucose concentration is above or below a certain upper and lower threshold. In a further aspect, the algorithm may not recommend an update to a current glucose dosage unless the fasting blood glucose concentration is outside a certain threshold for a certain number of consecutive days, such as, for example, for two or more straight days.

In another embodiment, if the difference between a current fasting blood glucose concentration and a preceding day's fasting blood glucose concentration is outside a predetermined threshold level, a software program for calculating the insulin dosage update may be programmed to not recommend an update to an insulin dosage regimen for safety measures in the case that the current fasting blood glucose concentration is in error or is not an acceptable value. Furthermore, the algorithm may be programmed to not recommend an update to an insulin dosage regimen if the insulin dosage regimen was recently updated, for example, if the insulin dosage regimen was updated within the preceding two days.

In another aspect, if it is determined that current measured values are found to be outside threshold values, such as if the difference between a current fasting blood glucose concentration and a preceding day's fasting blood glucose concentration is outside a predetermined threshold, an alarm system may activate. The alarm system may be in the form of an auditory, visual, and/or vibratory alarm, or may be an alarm notification transmitted over a data network to, for example, a healthcare professional. Other values that may activate the alarm system may include, an upper or lower threshold current blood glucose value, a threshold number of consecutive days wherein the fasting blood glucose value increased or decreased, a missed expected sample time, or if an error is detected.

Referring back to FIG. 13, the health monitor device 600 may also include programming to calculate a fast-acting insulin dosage. In one embodiment, while the dosage calculation for a long-acting insulin is used to maintain a stable safe baseline glucose concentration, a fast-acting insulin injection may be used to help stabilize blood glucose concentration fluctuations throughout the day due to, for example, carbohydrate intake. To that end, the health monitor device 600 may prompt for a non-fasting bodily fluid sample (1360), which may be in the form of a blood sample applied to a test strip 650 and received at the strip port 640 of the health monitor device 600.

Non-fasting blood samples may be taken periodically throughout the day at regular intervals or at irregular intervals depending upon a patient's physical state, such as when a patient determines that his/her blood glucose level is lower or higher than one or more predetermined threshold or desired level. Furthermore, events may also define when a patient takes a non-fasting blood sample, such as before or after meals, exercise, or after taking other medications.

Once the non-fasting blood sample is received at the strip port 640 of the health monitor device 600, the blood sample may then be analyzed and a blood glucose concentration is determined (1370). An algorithm for calculating a fast-acting insulin dosage recommendation may then be applied to the ascertained blood glucose concentration in order to calculate a recommended fast-acting insulin dosage (1380) to be displayed on a display unit 620 of the health monitor device 600 (1390). In other embodiments, the algorithm may be designed for calculating a dosage recommendation for an intermediate, rapid, or very-rapid acting insulin type or a combination thereof.

In other embodiments, a health monitor device 600 including programming for calculating a medication dosage or therapy profile recommendation may further include an integrated medication delivery system. In one embodiment the integrated medication delivery system may automatically deliver the medication dosage as recommended by the health monitor device 600. In one aspect, the health monitor device 600 may be preprogrammed with information related to the medication of the medication delivery system thus eliminating any possible errors resulting from a patient's accidental entry of a wrong medication in a medication selector function of the health monitor device 600. In another aspect, the medication delivery system may be detachable from the health monitor device 600.

In another embodiment, a health monitor device 600 including programming for calculating medication dosages for two or more medication types may further include an integrated medication delivery system. In one aspect, the medication delivery system may include two or more reservoirs, each designated for storing one of the two or more medication types, and each with an individual delivery mechanism. In another aspect, the two or more reservoirs may share a single delivery mechanism. In one aspect, the medication delivery system may automatically deliver each medication in doses as recommended by the health monitor device 600.

In another embodiment, the health monitor device 600 may include a corresponding docking station or one or more other peripheral devices. The docking station may include, among others, a transmitter whereby when the health monitor device 600 is docked to the docking station, the health monitor device 600 and docking station may communicate over a data network with, for example, a healthcare provider, for the transfer of data or receipt of instructions or new dosage regimens. The docking station transmitter may be configured for transmission protocols including, but not limited to, cellular telephone transmission, such as code division multiple access (CDMA) or Global System for Mobile communications (GSM), internet communication, facsimile communications, and/or telephone communication. In another aspect, the docking station may also be configured to provide power for recharging a rechargeable battery of the health monitor device 600. In another aspect, the docking station may be configured for communication with a personal computer for additional storage, programming, and/or communication.

In another embodiment, the health monitor device 600 may include software for monitoring and ordering replacements for consumable products associated with the health monitor device 600. Consumable products may include, among others, analyte test strips, lancing devices, types of medication, such as types of long-acting and fast-acting insulin, medication deliver devices, such as syringes or injection pens, integrated lancet and testing striplet devices, sensors for an implantable sensor glucose monitoring system, or batteries.

Figure 14:
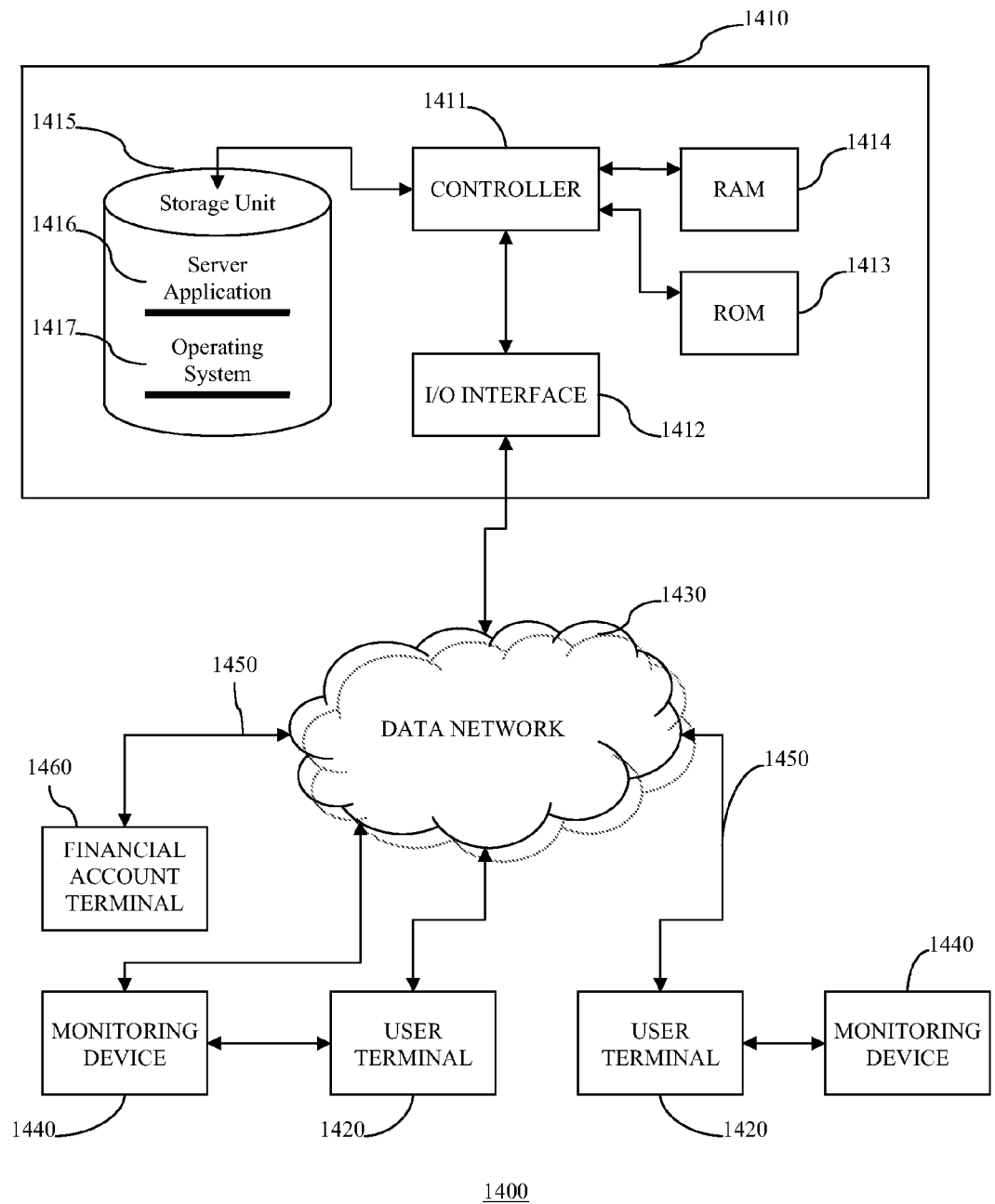
FIG. 14 illustrates a block diagram of a replenishment management system in accordance with one embodiment of the present disclosure.

FIG. 14 illustrates a block diagram of a replenishment management system in accordance with one embodiment of the present disclosure. Referring to FIG. 14, the replenishment management system 1400 includes a server terminal 1410 operatively coupled to one or more user terminals 1420 via a data network 1430. As can be seen from the Figure, each of the user terminals 1420 are also configured to be operatively connected to a respective one or more testing or monitoring devices 1440. As will be discussed in further detail below, there is also provided a financial account terminal 1460 operatively coupled to the data network 1430 for communication with the server terminal 1410 and a corresponding one of the user terminals 1420.

In one embodiment, the testing or monitoring device 1440 may include a health monitor device as described above in conjunction with FIG. 6A, which may be configured to automatically and wirelessly transmit the measured analyte data to the server terminal 1410 at a predetermined frequency over the wireless connection 1451. In this case, the server terminal 1410 may be configured to detect and receive the measured analyte data from the health monitor device and to store the received data in a corresponding user account associated with the health monitor device. Furthermore, in another embodiment, the health monitor device is configured to transmit medication dosage information, such as insulin dosage information, to the server terminal 1410. The medication dosage information may be information related to periodic dosages of long-acting and/or fast-acting insulin.

Referring back to FIG. 14, it can be seen that each of the user terminals 1420, the financial account terminal 1460, and the server terminal 1410 are operatively coupled to the data network 1430 via a corresponding data communication link 1450. Within the scope of the present disclosure, the data communication link 1450 may include a wired or wireless communication path which may be configured for secure, encrypted bi-directional data exchange over the data network 1430. In particular, the data communication link 1450 in one embodiment may include Wi-Fi data communication, infrared data communication (for example Infrared Data Association (IrDA) communication), Bluetooth® data communication, ZigBee® data communication, USB or FireWire cable based data communication, Ethernet cable based data communication, and dial up modem data communication.

For example, in one embodiment, the user terminals 1420 may include, among others, one of a personal computer (including a desktop or a laptop computer) or a handheld communication device such as an iPhone, Blackberry, Internet access enabled mobile telephones, a bi-directional communication enabled pager, and a communication enabled personal digital assistant (PDA). In one embodiment, the user terminals 1420 include an output unit such as a display and/or speakers, an input unit such as a keyboard or a touch-sensitive screen, as well as a controller such as a CPU for performing user instructed procedures at the user terminals 1420. Moreover, within the scope of the present disclosure, the user terminals 1420 may be configured to communicate with the data network 1430 using a wireless data communication protocol such as Bluetooth®, 801.11x, and ZigBee®. Additionally, the user terminal 1420 may also be configured to communicate with the testing or monitoring device 1440 via short range RF communication path, an IrDA communication path, or using Bluetooth® communication protocol. Additionally, the testing or monitoring device 1440 may also be configured to connect to the respective user terminals 1420 via a wired connection such as a USB connection, an RS-232 cable connection, an IEEE 1394 or FireWire connection, or an Ethernet cable connection.

Referring again to FIG. 14, the financial account terminal 1460 may be configured to communicate with the server terminal 1410 and the user terminals 1420 over the data network 1430 using either or a wired or wireless secure and encrypted connection. As is generally the case, because financial account related information is very sensitive, a high level of security for data communication to and from the financial account terminal 1430 may be used such as an encryption level exceeding 128-key encryption, and the like. Within the scope of the present disclosure, the financial account terminal 1460 may include one of a banking institution terminal, a credit card institution terminal, a brokerage institution terminal, and any other financial institution terminal which maintains a financial account of a user with which financial account transactions may be performed. This aspect of the present disclosure is discussed in further detail below.

Referring yet again to FIG. 14, the server terminal 1410 in one embodiment may include a controller 1411 operatively coupled to an input/output (I/O) interface unit 1412, a read-only memory (ROM) 1413, a random access memory (RAM) 1414, and a storage unit 1415. In one embodiment, the storage unit 1415 includes a server application 1416 and an operating system 1417. In this manner, the controller 1411 may in one embodiment be configured to communicate with the user terminals 1420 and the financial account terminal 1460 over the data network 1430 via the I/O interface unit 1412, under the control of the various processes and routines stored in the ROM 1413 and the storage unit 1415 as well as user transmitted requests and information.

In one embodiment, the server application 1416 and the operating system 1417 of the storage unit may be configured to provide a proprietary interface for the users, to execute secure and encrypted data communication over the data network 1400. More specifically, the server terminal 1410 may be configured to provide a proprietary internet-based user interface at a predetermined URL for the users to login from the user terminals 1420, for example, for communication with the server terminal 1410. Alternatively, within the scope of the present disclosure, the data network 1430 may include the internet, and wherein the server application 1416 and the operating system 1417 of the server terminal 1410 are configured to provide a dedicated website for allowing the users to securely and easily log in to their respective accounts using the user terminals 1420 over the data network.

Referring still again to FIG. 14, the storage unit 1415 of the server terminal 1410 in one embodiment may be configured to store data and information related to the user accounts such as, but not limited to, user account login identification and password, user contact information such as telephone and/or facsimile numbers, email addresses, billing and shipping addresses, user account profile information such as replenishment level information, seasonality or periodicity of user use of the testing, monitoring, or dosing device, prescribed medication information, user financial account information (for example, a bank routing number and bank account number in the case of a banking institution), and user testing, monitoring, or medication dosing device data information such as the user strip order history, medication order history, health related monitoring data such as previously measured glucose levels, user specific basal profile information, bolus determination information, insulin sensitivity, trend information determined based on the measured glucose levels (and determined by the controller 1411), and healthcare provider information for the user such as contact information for the user's physician, hospital, and nursing facilities.

In addition, within the scope of the present disclosure, the storage unit 1415 may further be configured to store an expiration information and/or lot number associated with the consumable item, or to calculate expiration information from the lot number. For example, the server terminal 1410 may be configured to determine the expiration information of the consumable item prior to or at the time of replenishment transaction (discussed in detail below), based on one or more of several factors, and further configured to transmit the expiration information to the user terminal 1420 associated with the replenishment transaction. The one or more of the several factors determining the expiration information associated with the consumable item includes the lot number associated with the consumable item, where each lot number has a unique expiration date associated therewith, a shipment date of the consumable item from the manufacturer, and a date of manufacture of the consumable item.

In this manner, in one embodiment, the user requesting the replenishment transaction for the consumable item will be notified of the expiration information such as the expiration date associated with the consumable item, and will be alerted that the consumable item will not function as optimally beyond the expiration date. In the case of glucose test strips, to ensure the accuracy of the test results showing the measured glucose levels it is important that the user/patient be aware of such expiration date of the glucose test strips, so that the measured glucose levels are as accurate as possible. In the case of medication, such as insulin, the importance of a patient's awareness of the expiration date may be even more important than the expiration date of a consumable item, such as a glucose test strip. In the case of medication, expired medication may not only have a diminished effectiveness, it may in fact have a severely detrimental effect on the patient's health.

Moreover, in the case where there is a physician or treatment advised, or other guideline as to frequency or threshold of testing, monitoring, or dosing, a warning signal may be generated and communicated to a healthcare professional or to the user in the case where the consumption of the test materials, as determined by the server terminal 1410, is less or more than the consumption required to meet this frequency or threshold of testing, monitoring or dosing.

Referring back to FIG. 14, in one embodiment of the present disclosure, based on the measured glucose levels for a given patient from a respective user terminal 1420, the controller 1411 of the server terminal 1410 may be configured to determine trend information based on measured glucose levels so as to determine and correspondingly generate for the user terminal 1420 for display, a color coded indication of the user's glucose level projections including arrow indicators, color coded warning or notification indicators, and associated audible alerts. For example, based on the user's measured glucose level for a predetermined period of time contemporaneously received from the user terminal 1420, the server terminal 1410 may be configured to generate and transmit to the user terminal 1420 a color coded arrow indicator for display on the user terminal 1420 to visually and easily inform the user of the projected or anticipated trend in the glucose level based on the measured glucose levels.

In another embodiment, based on the insulin dosage information for a given patient from a respective user terminal 1420, the controller 1411 of the server terminal 1410 may be configured to determine trend information based on insulin dosage information so as to determine and correspondingly generate for the user terminal 1420 for display, a color coded indication of the user's projected future insulin dosage information, including projected increase or decrease in insulin dosage. In one aspect, the controller 1411 may be configured to alert the patient if the rate of change of the insulin dosage information over a period of time is above a certain threshold, possibly indicating an advancement in a user's health condition, such as a worsening of a diabetic condition. When the change of insulin dosage over a period of time is above a predetermined threshold, it may be an indication that the user should visit their primary care physician in order to ascertain information relating to the health condition of the patient, and possibly determine a change in treatment or medication.

Referring still again to FIG. 14, the server application 1416 stored in the storage unit 1415 of the server terminal 1410 may be configured to perform, under the control of the controller 1411, the various procedures and processes as discussed below in conjunction with FIGS. 15-19, as well as to store any information related to the user accounts and profiles within the scope of the present disclosure.

Figure 15:
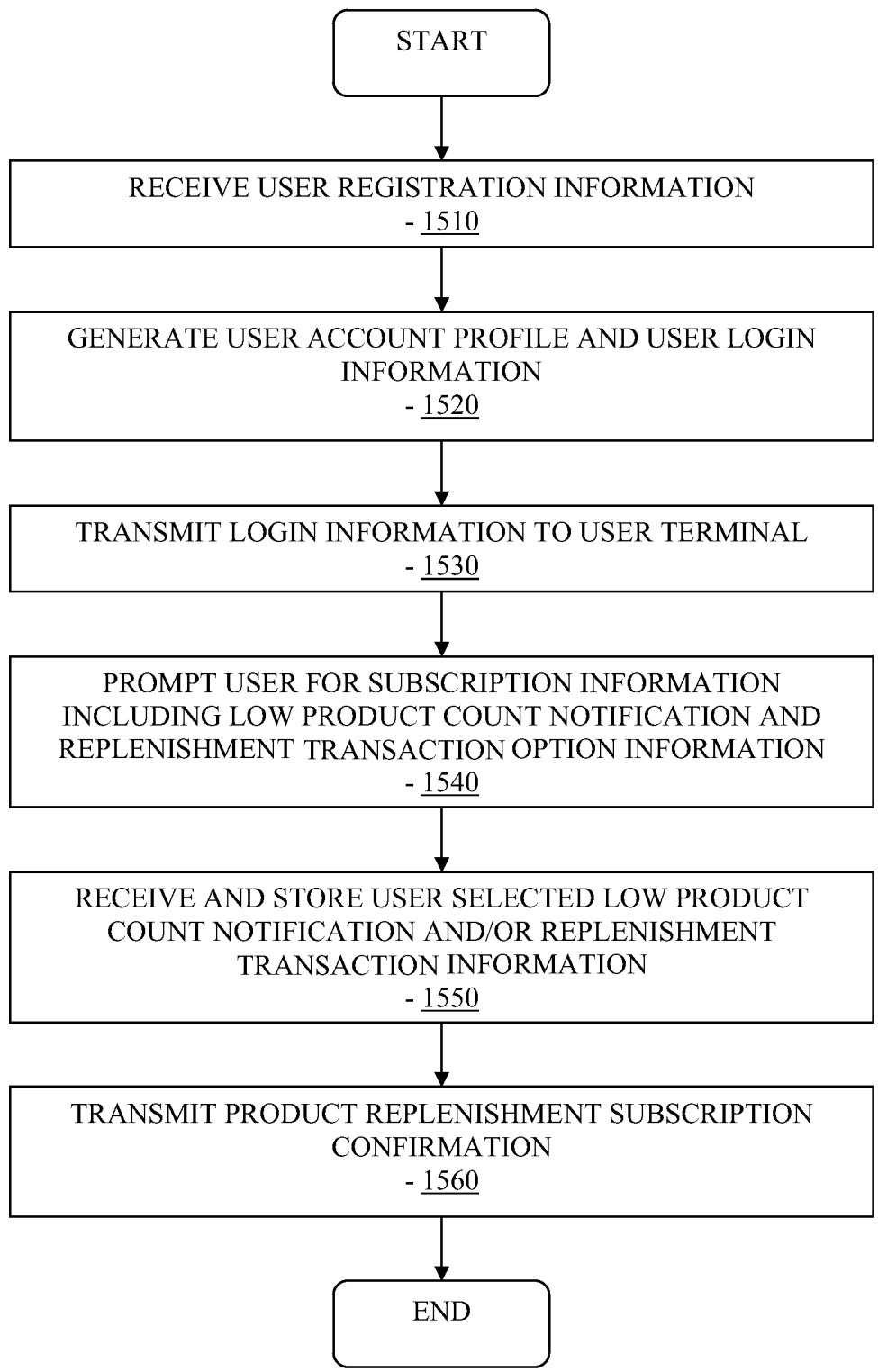
FIG. 15 is a flowchart illustrating user account registration setup and account subscription process in accordance with one embodiment of the present disclosure.

FIG. 15 is a flowchart illustrating user account registration setup and account subscription process in accordance with one embodiment of the present disclosure. Referring to the Figure, at step 1510, the server terminal 1410 (FIG. 14) receives from a user terminal 1420 user account registration information. The received user account registration information may include, among others, the user name, user address, the user telephone number, the user testing, monitoring, or dosing device information such as model information of the testing, monitoring, or dosing device, and the user medication prescription information.

Thereafter at step 1520, the server terminal 1410 is configured to generate a user account profile and login information including password and login identification, all of which are stored in the storage unit 1415 of the server terminal 1410. Then at step 1530, the server terminal 1410 is configured to transmit the user login information including the generated login identification information and associated password to the user terminal 1420. After transmitting the user login information or alternatively, substantially contemporaneously to the login information transmission, the server terminal 1410 is configured to transmit a prompt or request to the user terminal for the user desired subscription information for the consumable product replenishment. In one embodiment, the user desired consumable product replenishment subscription information may include low product count threshold notification information and consumable product replenishment transaction option information. A low product count threshold information may be a low test strip count or a low medication, such as insulin, amount.

More specifically, at step 1540, the server terminal 1410 in one embodiment is configured to request from the user via the user terminal 1420 when the user wishes to be notified of a low consumable product count for performing a replenishment procedure, and also, the user's desired purchase transaction option such as establishing a link to the user's financial institution. For example, if the user wishes to be notified of a low test strip count level when the user has 150 or less strips for usage with the health monitor device, the user may specify 150 as the low strip count level at which point, the user desired notification by the server terminal 1410 that replenishment procedure would be necessary. Furthermore, in one embodiment, the replenishment transaction option information provided to the user terminal 1420 by the server terminal 1410 may include one of establishing a link to the user's financial account institution for processing the purchase transaction for the purchase of the replenishment consumable product, prompting the user to allow purchase transactions over the data network 1430, and a simple replenishment notification with option to perform the purchase transaction for the purchase of the replenishment product.

Referring again to FIG. 15, at step 1550, the server terminal 1410 is configured to receive the user selected low consumable product count notification and the replenishment transaction information for the user account from the user terminal 1420. The server terminal 1410 then stores the received information related to the user selected low consumable product count notification and the chosen replenishment transaction option in the storage unit 1415 associated with the user account information also stored therein.

Then, as can be seen from FIG. 15, at step 1560, the server terminal 1410 may be configured to transmit a notification to the user terminal 1420 a confirmation of the receipt and the information which the user selected for the low consumable product count notification level and the product replenishment transaction that the user selected. Thereafter, the user account registration setup and account subscription process shown in FIG. 15 ends.

Figure 16:
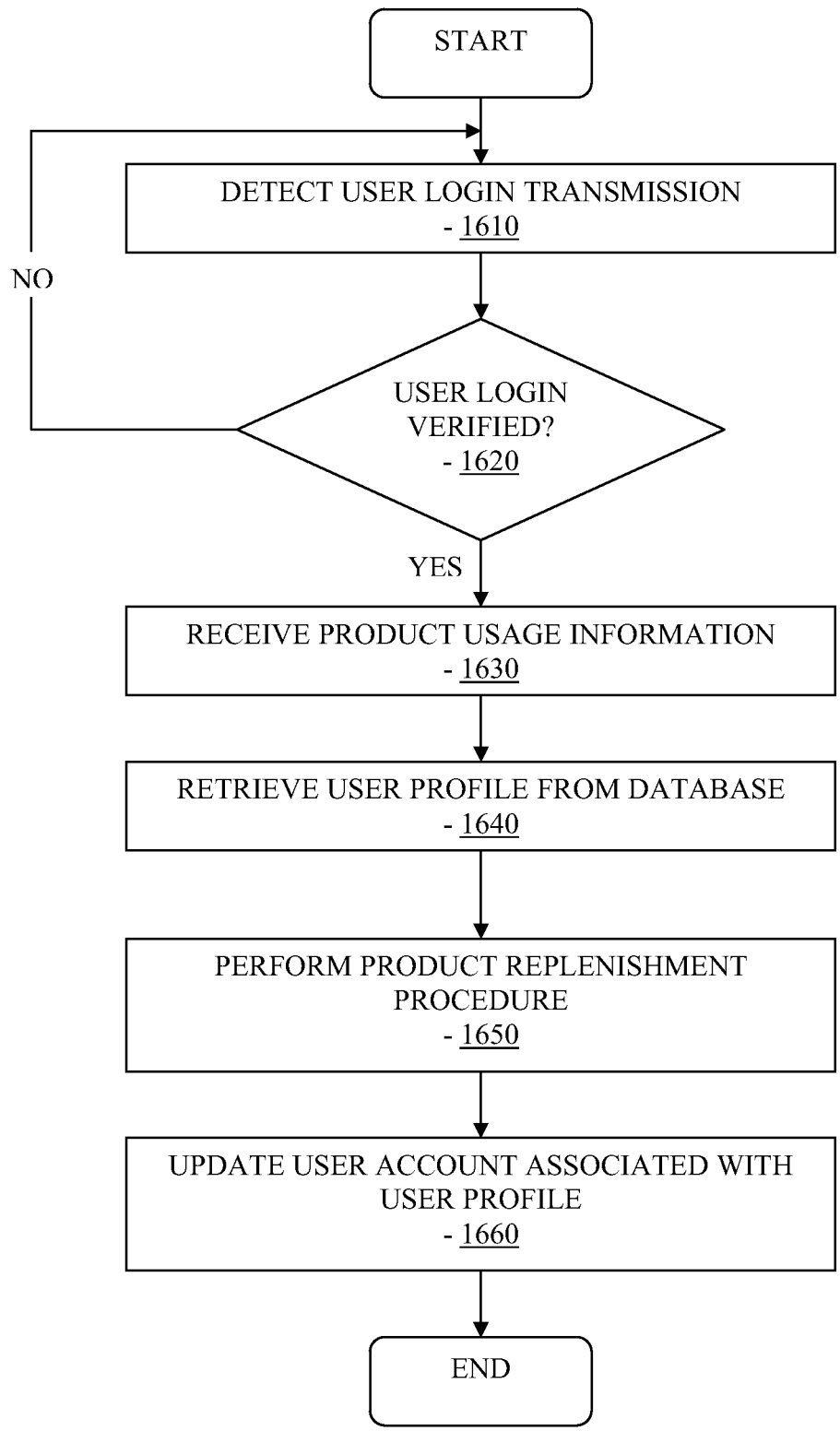
FIG. 16 is a flowchart illustrating an overall replenishment procedure for the user account in accordance with one embodiment of the present disclosure.

FIG. 16 is a flowchart illustrating an overall replenishment procedure for the user account in accordance with one embodiment of the present disclosure. Referring to the Figure, at step 1610, the server terminal 1410 (FIG. 14) in one embodiment is configured to detect a user login transmission, including, for example, the detection of the user account login identification information and the corresponding password transmitted from the user terminal 1420 over the data network 1430. Thereafter at step 1620, the server terminal 1410 is configured to verify the received user account login identification information. That is, in one embodiment, the server terminal 1410 is configured to confirm the accuracy of the received account login identification information from the user terminal 1420, and to correspond the received account login identification information to a corresponding stored user account. In one embodiment, the server terminal 1410 may be configured to search the storage unit 1415 for a user account profile generated and which corresponds to the received user account login identification information.

Referring to FIG. 16, if at step 1620 the received user account login identification information verification fails, the procedure returns to step 1610 and waits for a subsequent transmission of the user account login identification information from the user terminal 1420. Optionally, the server terminal 1410 may be configured to generate and transmit a login fail notification corresponding to the failed verification of the user account login at step 1620 to the corresponding user terminal 1420. On the other hand, if at step 1620 it is determined that the received user account login identification is verified, and thus, a corresponding user account profile is recognized by the server terminal 1410, then at step 1630, the server terminal 1410 is configured to receive a consumable product usage information from the user terminal 1420 whose user is now logged into the corresponding user account profile. Consumable product usage information may include, among others, usage information for the number of test strips or dosage information for a medication, such as a long-acting and/or a fast-acting insulin.

Thereafter, the server terminal 1410 at step 1640 is configured in one embodiment to retrieve the corresponding user account profile from the storage unit 1415, for example, (such as in a database associated with the storage of the user account profiles in the storage unit 1415). Then, with the consumable product usage information received from the user terminal 1420, and the corresponding user account profile retrieved from the storage unit 1415, in one embodiment, the server terminal 1410 at step 1650 is configured to perform a consumable product replenishment procedure discussed in further detail below to replenish the consumable product supply associated with the user account profile.

While the present embodiment is mainly described in conjunction with glucose test strips to be used for the periodic glucose level testing and with insulin medication to be used for controlling a patient's blood glucose level, the present disclosure may be applied and would equally cover any procedure which is configured to replenish a given quantity of consumables (for example, medications to be consumed at a predetermined time interval). Referring back to the Figure, upon completing the consumable product replenishment procedure at step 1650, the server terminal 1410 at step 1660 may be configured to update the user account profile associated with the user by for example, updating the database stored in the storage unit 1415 of the server terminal 1410 associated with the user account profile for the user that is logged in.

Furthermore, within the scope of the present disclosure, the database stored in the storage unit 1415 may also be linked to systems that are configured to track user demand, so as to forecast and anticipate demand, and also to track overall consumption patterns, preference, seasonal demand, geographic demand, and other similar demographic data for use in managing supply side activities more effectively and efficiently. The individual user data in the database stored in the storage unit 1415 may also include insurance or other individual reimbursement coverage rates of the individual user. This data may be used to determine a user co-pay and the amount that the insurance or other individual reimbursement coverage allows to the individual user. The results of these calculations on the user data in the database stored in the storage unit 1415 may be used as a basis for purchase or charge transaction to user for the co-pay amount, to charge the insurance or other individual reimbursement coverage for the amount so covered, and also to provide an alert signal in the case that the individual user may exceed the limits of payment coverage, as stored in the database in the storage unit 1415, so that action may be taken based on the alert signal.

Figure 17:
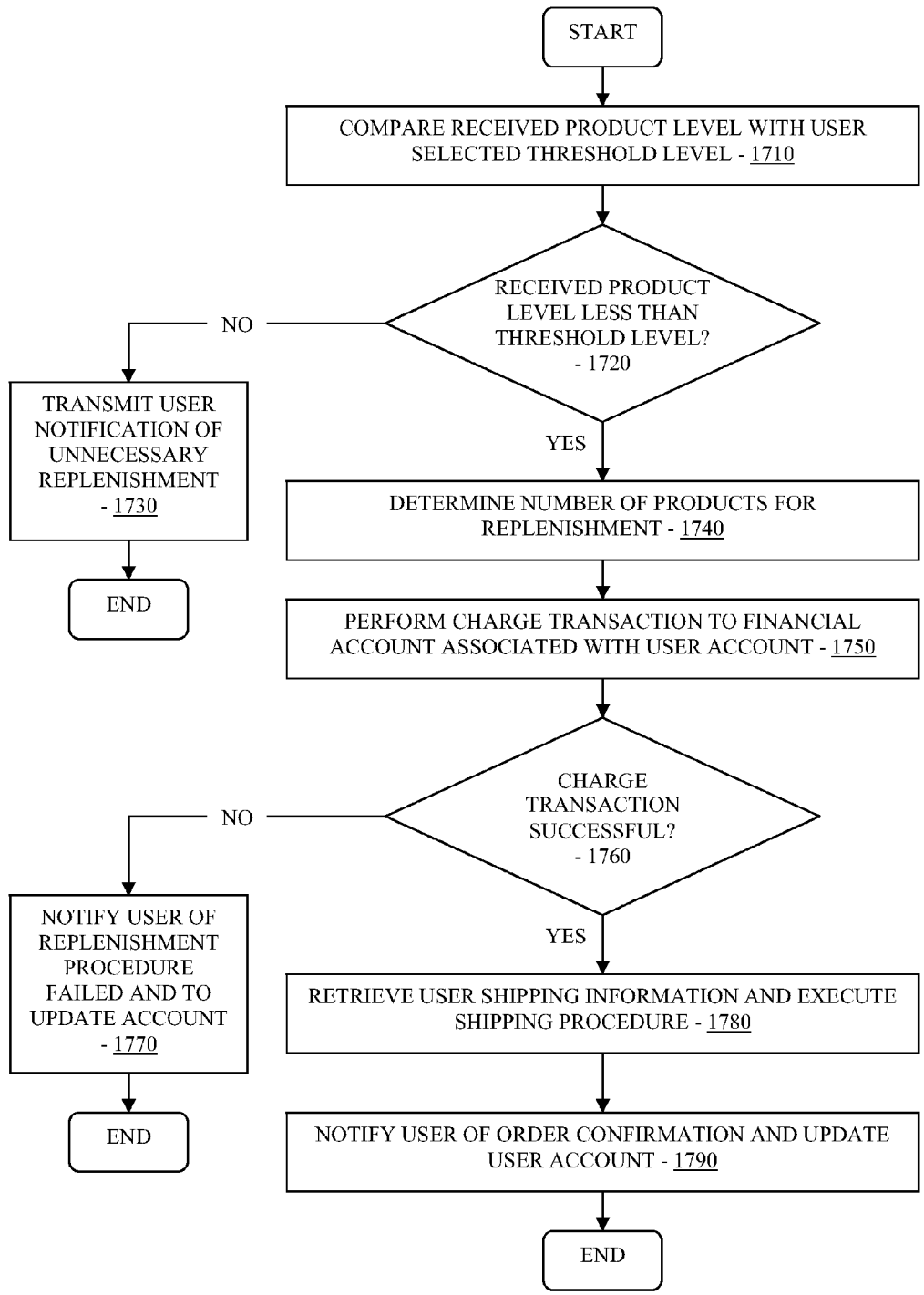
FIG. 17 is a flowchart illustrating the replenishment procedure shown in FIG. 16 in further detail in accordance with one embodiment of the present disclosure.

FIG. 17 is a flowchart illustrating the replenishment procedure shown in FIG. 16 in further detail in accordance with one embodiment of the present disclosure. More specifically, the strip replenishment procedure of step 1650 (FIG. 16) in one embodiment begins at step 1710 where the server terminal 1410 (FIG. 14) in one embodiment is configured to compare the received consumable product usage level with a user selected threshold level. Referring back to FIG. 14, the user selected threshold level in one embodiment may correspond to the one or more of low consumable product count notification level which the user selected during the user account registration procedure as shown in FIG. 15. Moreover, the received consumable product usage level at step 1710 in one embodiment corresponds with the received consumable product usage information at step 1630 (FIG. 16) received from the user terminal 1420.

Referring back to FIG. 17, after the comparing step at step 1710 (or as a result of the comparison step of step 1710), the consumable product replenishment procedure at step 1720 determines whether the received consumable product usage level is below the user selected threshold level. If it is determined at step 1720 that the received consumable product usage level is above the user selected threshold level, then at step 1730, the server terminal 1410 transmits a user notification to the corresponding user terminal 1420 notifying that replenishment is unnecessary, and thereafter, the consumable product replenishment procedure terminates.

On the other hand, if at step 1720 it is determined that the received consumable product usage level is below the user selected threshold level, then, at step 1740, the server terminal is configured to determine the amount of the consumable product needed for replenishment. More specifically, the server terminal 1410 in one embodiment may be configured to not only determine whether consumable product replenishment is necessary for the associated user account, but also, what the amount of necessary replenishment should be based on one or more predetermined factors such as the desired or optimal consumable product level or count selected by the user (and previously stored in the storage unit 1415, for example, of the server terminal 1410), and the time frame in which the consumable product replenishment procedure is triggered based upon the user account profile information (that is, based on the user's consumable product usage history profile, whether the triggered consumable product replenishment procedure is temporally closer to the most immediately preceding consumable product replenishment procedure).

Within the scope of the present disclosure, such usage historical information determined by the server terminal 1410, for example, may provide valuable information to the user as well as to the server terminal 1410 to maintain an efficient and reliable consumable product replenishment routine so as to not result in either over supply of products, or a supply of consumable products running dangerously low.

Referring back to FIG. 17, after determining the number of consumable products that are needed for replenishment at step 1740 associated with the user account profile, at step 1750, the server terminal 1410 (FIG. 14) in one embodiment is configured to perform a charge transaction to the financial account associated with the user account so as to charge the user's financial account for the purchase and shipping of the replenishment products to the user associated with the user account profile. In one embodiment, as discussed above, the server terminal 1410 is configured to retrieve the financial account information stored and associated with the user account and performs the charge transaction over the data network 1430 with the corresponding financial account terminal 1460. As discussed above, the financial account information in one embodiment may include one of a bank account, a credit card account, a debit account, a pre-paid financial account, or any other cash or cash equivalent account (such as the redemption of airline miles or vendor points) which the server terminal 1410 is configured to recognize with monetary value.

Referring again to FIG. 17, at step 1760, it is determined whether the charge transaction performed at step 1750 is successful. More specifically, the server terminal 1410 in one embodiment is configured to interact with the financial account terminal 1460 over the data network 1430 in order to perform the charge or debit transaction for the amount associated with the amount of replacement product. If the associated financial account terminal 1460 returns a failed transaction notification to the server terminal 1410 based on the server terminal 1410 transmission of the charge transaction over the data network 1430, then at step 1770, the server terminal 1410 in one embodiment is configured to generate and transmit a notification to the user terminal 1420 notifying the user at the user terminal 1420 that the consumable product replenishment procedure has failed. Also, the server terminal 1410 is configured to notify the user that the reason for consumable product replenishment failure is due to inaccurate or outdated financial account information associated with the user account, and thus, is configured to prompt the user to update the user's financial account associated with the user's account profile stored in the server terminal 1410.

On the other hand, referring back to FIG. 17, if at step 1760, it is determined that the consumable product replenishment charge transaction is successful, then at step 1780, the server terminal 1410 is configured to retrieve the user shipping information associated with the user account profile, and executes the shipping procedure to ship the replenishment consumable products purchased by the user to the user's designated shipping location. In one embodiment, the server terminal 1410 may be configured to prompt the user to verify or update the desired shipping location (such as destination address and time frame for shipping to include expedited shipping or custom shipping options, for example).

Referring again to FIG. 17, upon executing the shipping procedure at step 1780, the server terminal at step 1790 is configured to generate and transmit a notification to the user terminal 1420 associated with the user account confirming the shipment of the ordered products as well as the shipping and the fulfilled order details. Also, the server terminal 1410 is configured to update the associated user account based on the charge transaction and the shipping transaction performed. In this manner, in accordance with one embodiment of the present disclosure, the users may conveniently place a shipment order of products in advance of running low on the product, and rather then relying upon the user's manual calculation or determination of the needed products based upon the user's usage, such determination is automatically performed for the user, and the user can easily make the purchase transactions for the replenishment consumable products quickly and easily.

Figure 18:
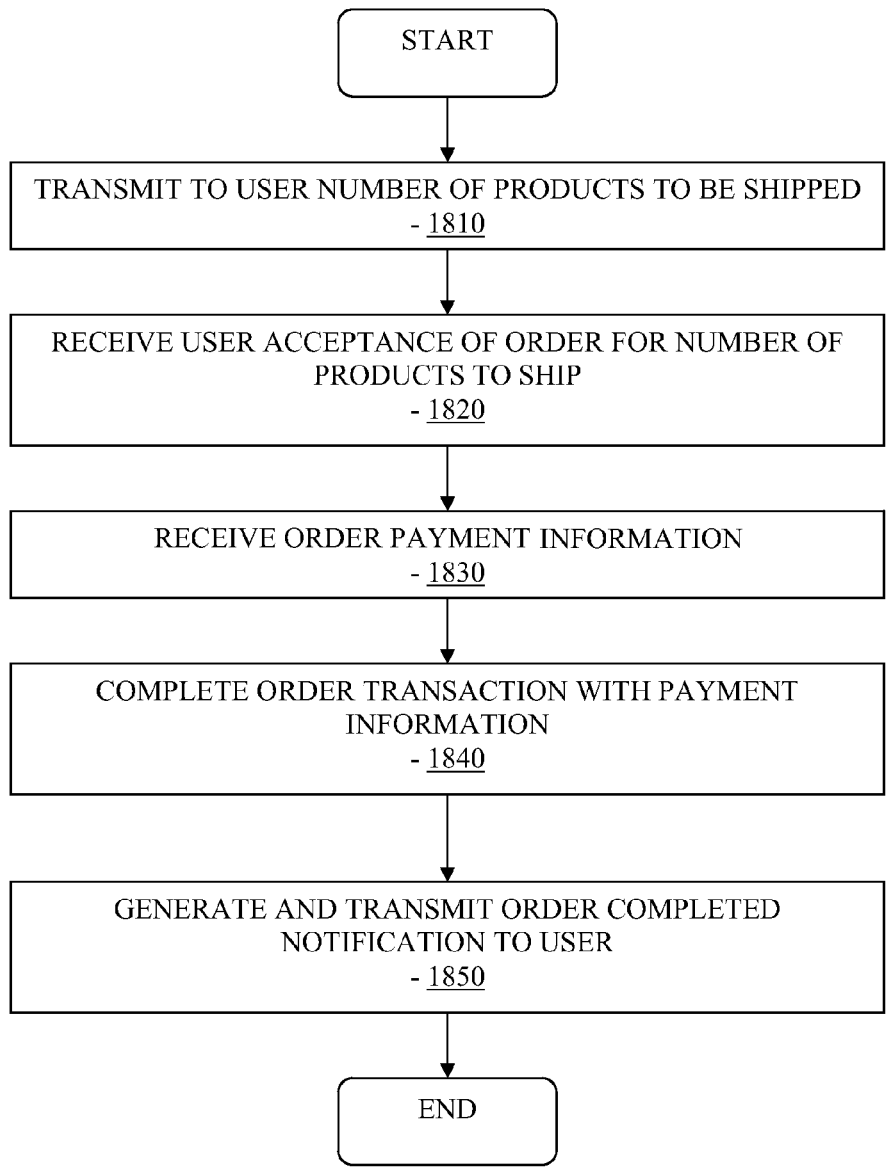
FIG. 18 is a flowchart illustrating the replenishment procedure shown in FIG. 16 in further detail in accordance with another embodiment of the present disclosure.

FIG. 18 is a flowchart illustrating the replenishment procedure shown in FIG. 16 in further detail in accordance with another embodiment of the present disclosure. Referring to the Figure, in one embodiment of the present disclosure, the server terminal 1410 is configured to transmit to the user terminal 1420 a predetermined or calculated amount of consumable products to be shipped at step 1810. In one embodiment, the server terminal 1410 may be configured to determine the amount of consumable products to be shipped based on one or more predetermined factors such as the user product usage level, the user selection of low consumable product notification information, the user's desired consumable product inventory, and the user's desired frequency of product replenishment.

Responsive to the amount of consumable products to be shipped notification received from the server terminal 1410, the user may confirm the received number of consumable products to be shipped as the number of products that the user wants to receive, and thus, may transmit an acceptance notification to the server terminal 1410 which the server terminal 1410 at step 1820 is configured to receive, for example, as an acceptance of the order associated with the amount of consumable products to be shipped to the user. Thereafter at step 1830, the server terminal 1410 may be configured to receive order payment information for the purchase of the amount of consumable products that the user has accepted to be shipped to the user. In one embodiment, the user may transmit from the user terminal 1420 to the server terminal 1410 over the data network 1430, a user financial account information, such as a credit card information or a bank account information to be used to perform the purchase transaction.

Referring back to FIG. 18, thereafter at step 1840, the server terminal 1410, having received the financial account information from the user terminal 1420, performs and completes the order transaction for the purchase of the amount of consumable products accepted by the user and to be shipped to the user with the received payment information. Upon performing and successfully confirming the order transaction at step 1840, the server terminal 1410 at step 1850 is configured in one embodiment to generate an order confirmation notification and to transmit the notification to the user. In one embodiment, the order confirmation notification may include the amount of consumable products ordered, the shipping or mailing address where the ordered products are to be shipped, and the amount charged to the financial account associated with the payment information.

In this embodiment, it can be seen that the user is not required to provide the user's financial account information to have it stored, for example, in the user account profile at the server terminal 1410. This approach would be particularly desirable for users who do not wish to have their financial account information disseminated and stored in vendor sites such as the server terminal 1410 configured to perform consumable product replenishment procedures.

Figure 19:
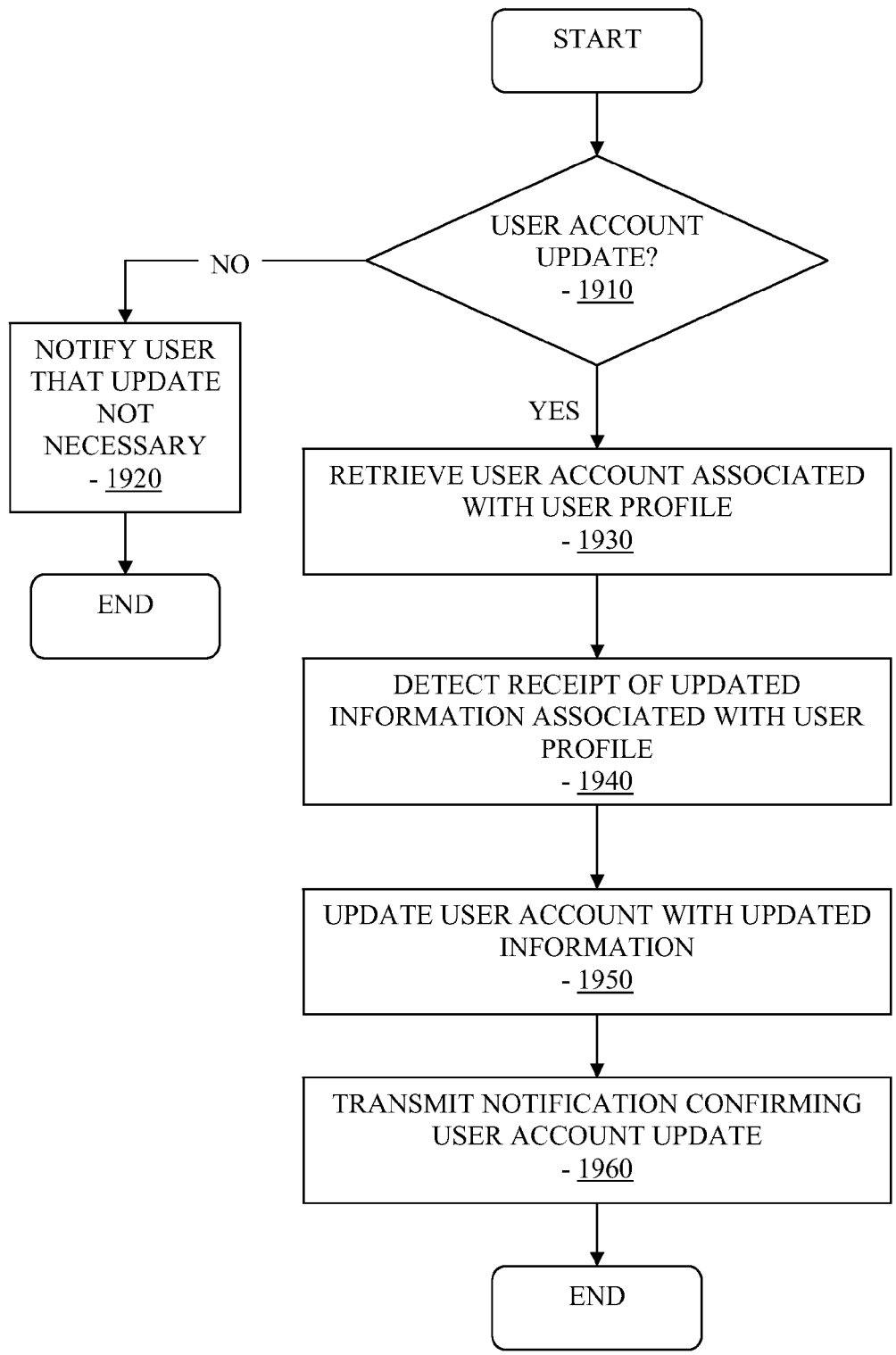
FIG. 19 is a flowchart illustrating a user account update and maintenance procedure in accordance with one embodiment of the present disclosure.

FIG. 19 is a flowchart illustrating a user account update and maintenance procedure in accordance with one embodiment of the present disclosure. Referring to the Figure, at step 1910, a user account update procedure is prompted. This may be a server terminal 1410 (FIG. 14) triggered procedure (for example, when it is determined that the user financial account information stored in the server terminal 1410 is outdated or no longer accurate), or alternatively, the user at the user terminal 1420 may initiate the user account update procedure of step 1910 based on the user's desire to modify one or more settings or parameters associated with the user account profile.

Referring to the Figure, in the case where the server terminal 1410 determines that the user account update is not needed, then at step 1920, it is determined that the account update procedure is unnecessary and a corresponding notification is transmitted to the user terminal 1420. For example, in the case where the user prompts a parameter which the user wishes to modify (such as by modifying the shipping information), if the server terminal 1410 determines at step 1910 that the updated information with which the user wishes to update is the same at that which is stored in the server terminal 1410, then, rather then expending the processing power of the server terminal 1410 to perform the user account update procedure, the server terminal 1410 is configured to generate and transmit the notification to the user terminal that the user specified account update is not necessary.

On the other hand, if it is determined that the user account update is to be performed at step 1910, then at step 1930, the server terminal 1410 is configured to retrieve the stored user account associated with the user profile. Thereafter, at step 1940, the server terminal 1410 is configured to detect the receipt of updated information associated with the user profile received from the user terminal 1420. Thereafter, the server terminal 1410 at step 1950 is configured to update the user account with the updated information received from the user terminal 1420. In one embodiment, the server terminal 1410 may be configured to update the database stored in the storage unit 1415, and which is associated with the user account to be updated based on the account update information received from the user terminal 1420. Upon completing the user account update with the received updated information, the server terminal 1410 at step 1960 is configured to transmit a notification to the user terminal 1420 to notify and confirm the update to the user account.

In the manner described above, in accordance with the various embodiments of the present disclosure, there is provided method and system for providing subscription based transaction for consumable items such as glucose test strips or insulin, which diabetic patients may effectively use to easily replenish glucose test strips or insulin when the patient is running low on such items. In one embodiment, the user's use of the account or access to the subscription based account profile serves to compare the number of remaining test strips with the desired minimum number of strips which the patient may have specified or the amount of remaining insulin with the desired minimum amount of insulin which the patient may have specified, and to automatically initiate and execute the purchase transaction of the test strips, insulin, or other consumables for the user to order, and deliver the products to the patient on time such that the patient does not run low on the item.

In this manner, in accordance with the various embodiments of the present disclosure, an efficient system and method for the user to always maintain a minimum number of consumable items on order or to be ordered based on the user's rate of usage of the item is provided.

Furthermore, within the scope of the present disclosure, the server terminal 1410 (FIG. 14) may be configured to provide a loyalty based rewards program such that based on a predetermined criteria, the users may be provided with a discounted price for the replenishment orders of the test strips or medication, such as insulin, and/or be offered a replacement health monitor device or medication delivery device based on the user's replenishment transaction history.

For example, the server terminal 1410 may be configured to flag a user account profile which has executed a threshold amount of replenishment transactions (whether based on the number of products ordered for replenishment, or based on the total value of the replenishment transactions sum), and to offer an incentive to continue to maintain the user account, and thus with the replenishment transactions. In one embodiment, the server terminal 1410 may be configured to automatically offer to send a replacement health monitor device and/or medication delivery system, such as a syringe or injection pen, at every calendar year (or at a predetermined frequency) so long as the user's frequency and volume of replenishment transaction satisfies a threshold level. Alternatively, the server terminal 1410 may be configured to apply a price discount for future replenishment transactions based on the user satisfying the threshold level discussed above. In this manner, within the scope of the present disclosure, the users or patients are provided with an incentive to continue to maintain the user account and to continue performing the replenishment transactions.

Additionally, in a further embodiment of the present disclosure, where there are existing contracts with a provider of insurance or other individual reimbursement, or with a government or authority which provides group discounts when certain conditions are met, such as group price discounts or other special commercial terms, the server terminal 1410 may be configured to automatically provide the special commercial terms to the provider of insurance or other individual reimbursement, or to the government or authority.

Figure 20:
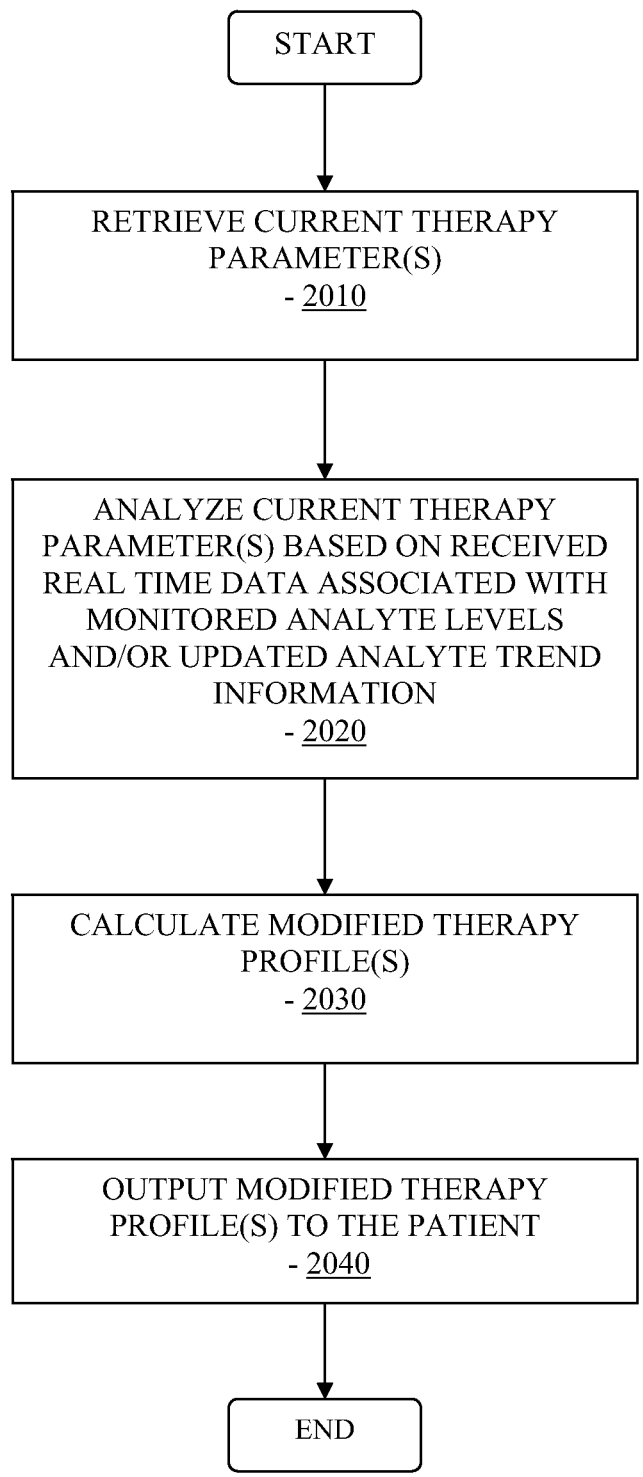
FIG. 20 is a flowchart illustrating modified therapy management procedure based on real time monitored analyte levels in accordance with one embodiment of the present disclosure.

FIG. 20 is a flowchart illustrating modified therapy management procedure including medication dosage determination based on real time monitored analyte levels in accordance with one embodiment of the present disclosure. Referring to FIG. 20, in one embodiment, the current therapy parameters are retrieved 2010 and the retrieved current therapy parameters are analyzed based on the received real time data associated with the monitored or acquired analyte levels and/or updated analyte trend information 2020. For example, one or more preprogrammed medication delivery profiles or rates including, for example, but not limited to medication delivery rate or profiles including, for example, basal profiles, correction bolus amount, carbohydrate bolus amount, temporary basal profiles and associated parameters are retrieved and analyzed based on, for example, the received real time data associated with the monitored or acquired analyte levels and/or updated analyte trend information, and may further, factor in the insulin sensitivity level or related information of the patient as well as insulin on board information.

Referring to FIG. 20, based upon the analysis of the current therapy parameters, one or more modified therapy profiles are calculated 2030. That is, based upon the glucose levels monitored by the health monitor device with a medication dose calculation function 100 (FIG. 1), a modification or adjustment to the programmed, pre-programmed or programmable basal profiles stored in the health monitor device with a medication dose calculation function 100 may be determined, and the modified therapy profile is output to the patient 2040, for example on the display 120 of the health monitor device 100. That is, the modification or adjustment to the pre-programmed delivery profiles (e.g., basal profiles) may be provided to the patient for review and/or execution to implement the recommended modification or adjustment to the programmed, pre-programmed or programmable therapy profiles (e.g., basal profiles).

Embodiments of the present disclosure include current therapy parameters as discussed above including medication delivery rate information, frequency of medication dosing information, previously administered medication delivery rate, amount, delivery duration, and the like, as well as medication sensitivity information (unique to each user or patient) including, for example, insulin sensitivity. Moreover, current therapy parameters further include exercise regimen, compliance to medication therapy information (for example, indications or confirmations that the recommended or programmed medication was administered, exercise regimen and/or diet profiles were followed or complied with, and the like).

In this manner, the patient may be provided with one or more adjustments to the existing or current therapy management profiles including for example, medication delivery profiles such as basal profiles and/or bolus dosage recommendation (amount or time period for administration) or any other programmed, pre-programmed or programmable therapy profiles based on monitored or acquired physiological levels of the patient such as analyte levels of the patient. Indeed, in one embodiment of the present disclosure, using monitored glucose levels of the patient, modification or adjustment to the programmed, pre-programmed or programmable therapy management profiles may be determined and provided to the patient for review and/or implementation or execution as desired by the patient. That is, in one aspect, as may be appropriate or suitable, the user, when provided with the therapy modification recommendation, may decide to execute or implement the recommended therapy modification for example, initiating one or more routines of functions for implementation of the same. In this manner, for example, a diabetic patient may improve the insulin therapy management and control of the variation in the glycemic levels within desired and/or acceptable range.

In one or more embodiments, therapy parameters may be associated with or tagged in conjunction with current or past analyte level measurements. In this manner, when a patient measures their current analyte level, for example utilizing a health monitor device such as those described in FIGS. 1, 6A and 7, one or more therapy related parameter and/or associated analyte level measurements may be tagged or flagged and the corresponding tagged or flagged information stored in the database. Therapy parameters which may be associated with analyte level measurements may include, but are not limited to, events such as medication intake, carbohydrate intake, exercise, sleep, travel, work related events, and associated parameters such as the amount or time duration related to the corresponding events.

For example, analyte level data may be stored in a database including the associative one or more tags related to the therapy parameters. A patient or other healthcare professional may then be able to query the database based on particular therapy parameters, and optionally use the results for, for example, determination of a desired therapy profile. The database, as described in further detail above, may be stored in the memory of the health monitor device, or alternatively or additionally be stored in a memory of an external peripheral device, computer, or server.

The therapy parameter tag may be associated with a current analyte level manually or automatically. In one aspect, the health monitor may display a request to the patient to confirm if a therapy parameter is associated with the current analyte level measurement. Furthermore, the health monitor may display a request to the patient to choose from a selected list of available therapy parameter tags, the corresponding current therapy parameter to associate with the current analyte level. In another aspect, the patient may manually choose to associate a therapy parameter tag with the current analyte level measurement by, for example, entering a preprogrammed code or choosing a therapy parameter tag from a list. In yet another embodiment, the health monitor device may be programmed to automatically determine if the current analyte level measurement should have a therapy parameter tag associated therewith. In one aspect, the health monitor device may compare the current time and analyte level with historical data saved in a database or memory, and determine based upon said historical data if the current analyte level measurement is likely associated with a therapy parameter tag. For example, if historical data indicated a carbohydrate intake within a preselected time range on each of a number of preceding days with a similar analyte level measurement as the current analyte level measurement, the health monitor may automatically tag the current analyte level measurement with a carbohydrate intake therapy parameter tag. In another aspect, if the patient is currently on a specific therapy regimen, including a medication, exercise, and/or diet regimen, the health monitor device may be programmed to associate analyte level measurements with corresponding therapy parameter tags during particular times of day in accordance with the specified therapy regimen. In one aspect, when the determination of an association of therapy parameter tags is automated by the health monitor device, the health monitor device may require a user confirmation prior to storing the data in a memory or database.

As discussed below, the adjustment or modification to the therapy management profiles may include statistical analysis, including, linear regression, modified linear regression analysis, forecasting techniques, data mining and/or other suitable data analysis to determine customized therapy management modification based on the variation in the glycemic profiles of the patient or the user. In certain aspects, routines and/or functionalities for data processing, analysis and display including user input and output of information may be performed by the health monitor devices (100, 600, 700) described above. That is, software algorithm or programs may be stored in one or more memory devices or storage units of the health monitor devices that may be retrieved or accessed by microprocessors and/or control units including, for example, application specific integrated circuits that includes one or more state machines programmed to perform routines or logic based on the algorithm or programs retrieved from the one or more memory devices or storage units.

Figure 21:
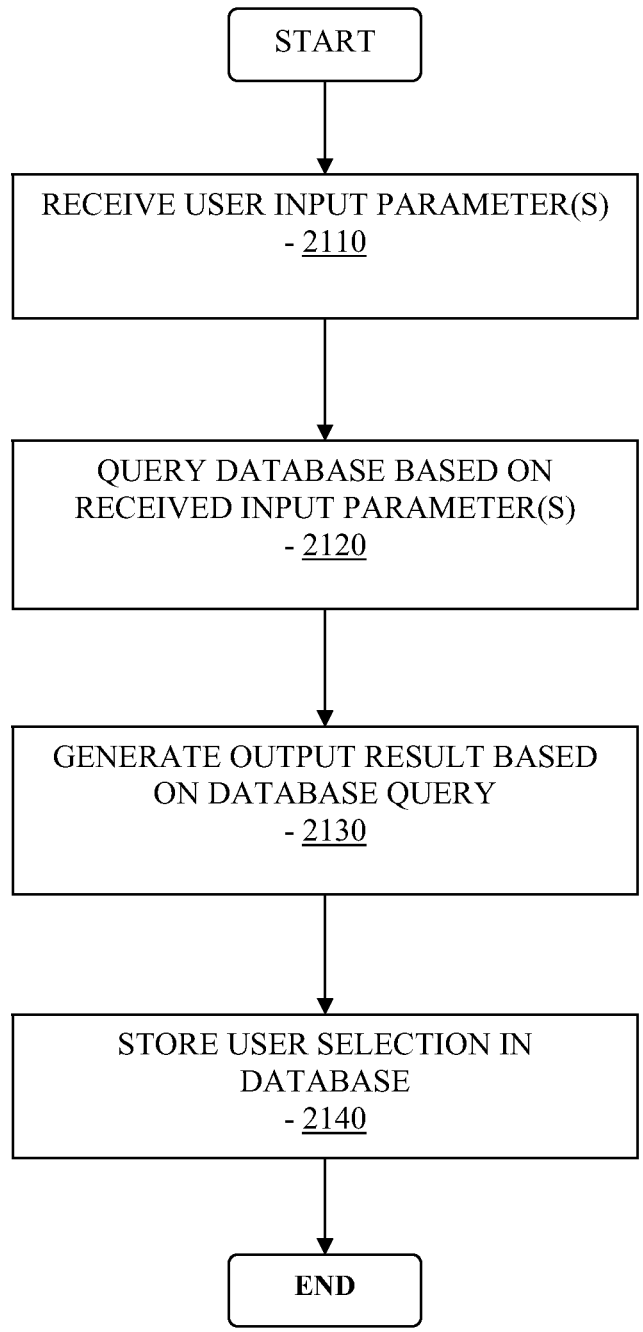
FIG. 21 is a flowchart illustrating contextual based therapy management in accordance with one embodiment of the present disclosure.

FIG. 21 is a flowchart illustrating contextual based therapy management including medication dosage determination in accordance with one embodiment of the present disclosure. Referring to the Figure, one or more user input parameter is received 2110 such as, for example, user's age, gender, physiological profile, existing medication (i.e., prescription or non-prescription medication consumed or ingested during a relevant time period), the amount of carbohydrate to ingest, type of exercise to perform, current time of day information, insulin on board information determined based on time and amount information of previously administered medication doses, frequency, type and amount of previously administered medication doses (for example, the frequency, time of day information, and/or amount of administered bolus doses over a predetermined time period (e.g., over a 24 hour period, over a 48 hour period, or all such information stored and/or available for use in the analysis) or any other appropriate information that may impact the determination of the suitable medication level. Based on the one or more user input parameters, one or more database is queried 2120. In one embodiment, the database may be provided in the health monitor device with a medication dose calculation function 100 (FIG. 1). Alternatively or in addition, the one or more databases may be provided in one or more remote locations such as a server or a remote user terminal.

Referring back to FIG. 21, the database query in one embodiment may be configured to search or query for medication dosage levels that are associated with similar parameters as the received one or more user input parameters. Thereafter, the queried result is generated and provided to the user 2130 which may be acted upon by the user, for example, to administer the medication dosage amount based on the queried result. The user selection of the administered medication dosage level is stored in the database 2140 with the associated one or more user input parameters as well as the time and date information of when the user has administered the medication dosage amount.

In this manner, in one embodiment, insulin dosages and associated contextual information (e.g., user input parameters) may be stored in the one or more databases for retrieval, analysis, updating and/or modification. For example, a bolus dose amount for a diabetic patient may be determined in the manner described above using the stored historical information without performing a mathematical calculation which takes into account of variables such as sensitivity factors varying with time and/or user's physiological conditions, and which may need to be estimated.

In particular, embodiments include contextual medication dosage determination that includes analyzing the current profile of the user or the patient to determine the relevant or suitable physiological profile of the user or the patient, by comparing to one or more of the previously stored profiles including the various parameters associated with the user or the patient's physiology, medication history, diet, as well as other parameters to retrieve the corresponding medication dosage previously administered for recommendation to the user or the patient. The recommended dosage or the therapy or delivery profile may be further refined or modified by the patient or the user prior to administration or implementation.

In particular, in one embodiment of the present disclosure, insulin dependent users may determine their appropriate insulin dosages by, for example, using historical dosage information as well as associated physiological condition information. For example, the historical data may be stored in one or more databases to allow search or query based on one or more parameters such as the user's physiological condition and other contextual information associated with each prior bolus dosage calculated and administered. In this manner, the user may be advised on the proper amount of insulin under the particular circumstances, the user may be provided with descriptive statistical information of insulin dosages under the various conditions, and the overall system may be configured to learn and customize the dosage determination for the particular user over an extended time period.

For example, in one aspect, contextual information may be stored with the insulin bolus value. The contextual data in one aspect may include one or more of blood glucose concentration, basal rate, type of insulin, exercise information, meal information, carbohydrate content estimate, insulin on board information, and any other parameters that may be used to determine the suitable or appropriate medication dosage level. Some or all of the contextual information may be provided by the user or may be received from another device or devices in the overall therapy management system such as receiving the basal rate information or blood glucose concentration from the health monitor device with a medication dose calculation function 100 (FIG. 1).

By way of an example, a contextually determined medication dosage level in one embodiment may be provided to the user along with a suitable or appropriate notification or message to the user that after a predetermined time period since the prior administration of the medication dosage level, the blood glucose level was still above a target level. That is, the queried result providing the suitable medication dosage level based on user input or other input parameters may be accompanied by other relevant physiological condition information associated with the administration of the prior medication dosage administration. In this manner, when the user is provided with the contextually determined medication dosage level, the user is further provided with information associated with the effects of the determined medication dosage level to the user's physiological condition (for example, one hour after the administration of the particular medication dosage level determined, the user's blood glucose level changed by a given amount). Accordingly, the user may be better able to adjust or modify, as desired or needed, the contextually determined medication dosage level to the current physiological conditions.

In this manner, in one embodiment, to determine and provide the user with proper medication dosage levels, the present or current context including the patient's current physiological condition (such as current blood glucose level, current glucose trend information, insulin on board information, the current basal profile, and so on) is considered and the database is queried for one or more medication dosage levels which correlate (for example, within a predetermined range of closeness or similarity) to the one or more current contextual information associated with the user's physiological condition, among others.

Accordingly, in one embodiment, statistical determination of the suitable medication dosage based on contextual information may be determined using, one or more of mean dosage determination, using a standard deviation or other appropriate statistical analysis of the contextual information for medication dosages which the user has administered in the past. Further, in one aspect, in the case where no close match is found in the contextual query for the desired medication dosage level, the medication dosage level with the most similar contextual information may be used to interpolate an estimated medication dosage level.

In still another aspect, the database query may be configured to provide time based weighing of prior medication dosage level determinations such that, for example, more recent dosage level determination in which similar contextual information may be weighed heavier than aged dosage level determination under similar conditions. For example, older or more aged bolus amounts determined may be weighed less heavily than the more recent bolus amounts. Also, over an extended period of time, in one aspect, the older or aged bolus amounts may be aged out or weighed with a value parameter that minimally impacts the current contextual based bolus determination. In this manner, in one aspect, a highly personalized and individualistic profile for medication dosage determination may be developed and stored in the database with the corresponding contextual information associated therewith.

Figure 22:
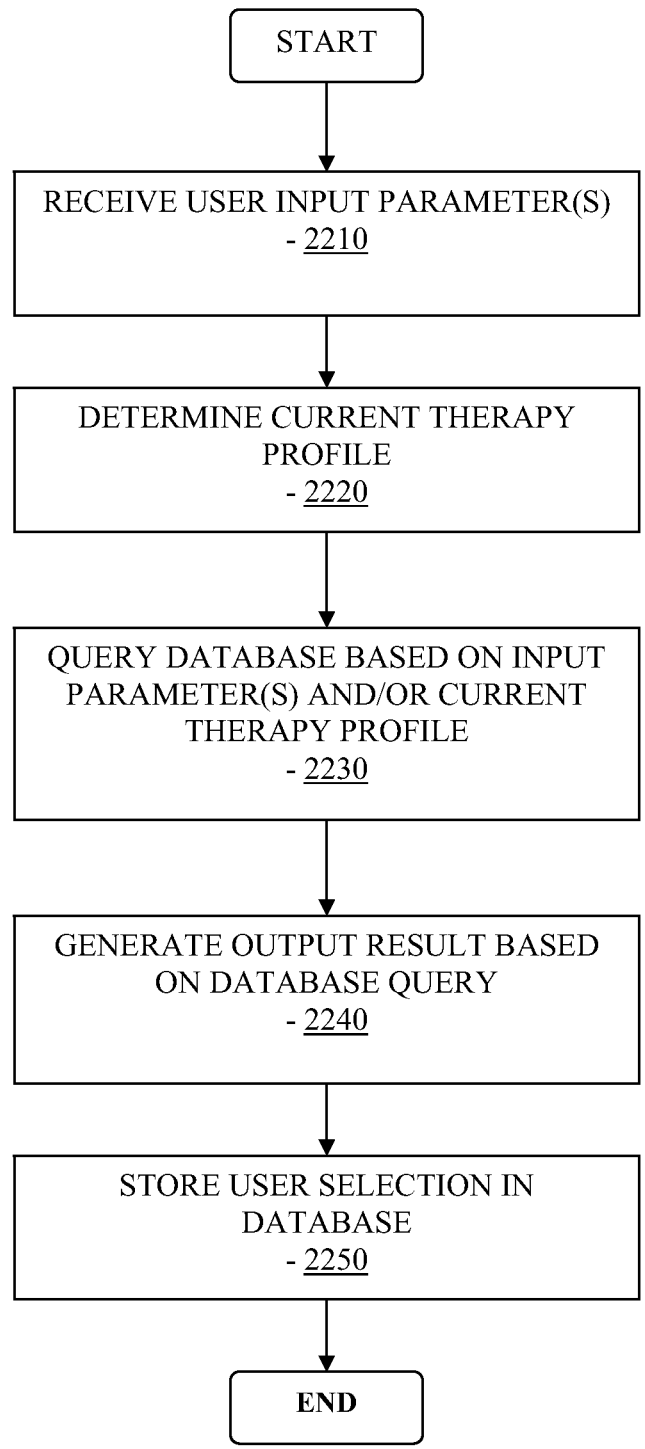
FIG. 22 is a flowchart illustrating contextual based therapy management in accordance with another embodiment of the present disclosure.

FIG. 22 is a flowchart illustrating contextual based dosage determination in accordance with one embodiment. Referring to FIG. 22, in one aspect, when the user input parameters are received at step 2210, the current therapy profile of the user's medication delivery system, such as an insulin pump, is determined at step 2220. Thereafter, the database is queried based on the input parameters and the current therapy profile at step 2230, which results in one or more contextually determined bolus amount associated with the input parameters and the current therapy profile at step 2240 that is provided to the user. The determined bolus amount is then at step 2250 stored in the database with the associated input parameters and the current therapy profile and any other contextual information associated with the determined bolus amount.

In this manner, in one aspect, in addition to the user provided input parameters, other relevant contextual information may be retrieved (for example, the current therapy profile such as basal rate, the current blood glucose level and/or glucose trend information from the health monitor device with a medication dose calculation function 100 (FIG. 1), and the like) prior to the database query to determine the suitable bolus amount.

As discussed above, optionally, the contextual information including the user input parameters and other relevant information may be queried to determine the suitable medication dosage level based on one or more statistical analysis such as, for example, but not limited to, descriptive statistics with the use of numerical descriptors such as mean and standard deviation, or inferential statistics including, for example, estimation or forecasting, correlation of parameters, modeling of relationships between parameters (for example, regression), as well as other modeling approaches such as time series analysis (for example, autoregressive modeling, integrated modeling and moving average modeling), data mining, and probability.

Embodiments further include querying the one or more databases or storage devices to perform statistical analysis including or based at least in part on a hierarchy of the therapy profile parameters that is either pre-programmed or stored in the database (based on for example, level of relevance, temporal occurrence, user identified ranking of importance, healthcare provider identified ranking of importance, similarity, dissimilarity, occurrence prior to another event, occurrence after another event, occurrence in conjunction with a predetermined physiological condition, etc).

By way of a further non-limiting example, when a diabetic patient plans to take insulin of a particular type, the patient enters contextual information such as that the patient has moderately exercised and is planning to consume a meal with a predetermined estimated carbohydrate content. The database in one embodiment may be queried for insulin dosages determined under similar circumstances in the past for the patient, and further, statistical information associated with the determined insulin dosage is provided to the user. In one aspect, the displayed statistical information associated with the determined insulin dosage may include, for example, an average amount of insulin dosage, a standard deviation or a median amount and the $25^{th}$ and the $75^{th}$ percentile values of the determined insulin dosage.

The patient may consider the displayed statistical information associated with the determined insulin dosage, and determine the most suitable or desired insulin amount based on the information received. When the patient programs the insulin pump to administer the desired insulin amount (or otherwise administer the desired insulin amount using other medication administration procedures such as injection (using a pen-type injection device or a syringe), intaking inhalable or ingestable insulin, and the like) the administered dosage level is stored in the database along with the associated contextual information and parameters.

In this manner, the database for use in the contextual based query may be continuously updated with each administration of the insulin dosage such that, each subsequent determination of appropriate insulin dosage level may be determined with more accuracy and is further customized to the physiological profile of the particular patient. Additionally, the database queried may be used for other purposes, such as, for example, but not limited to tracking medication information, providing electronic history of the patient related medical information, and the like. Further, while the above example is provided in the context of determining an insulin level determination, within the scope of the present disclosure, other medication dosage may be determined based on the contextual based database query approaches described herein.

In a further aspect, the contextual based medication dosage query and determination may be used in conjunction with the standard or available medication dosage determination (for example, standard bolus calculation algorithms) as a supplement to provide additional information or provide a double checking ability to insure that the estimated or calculated bolus or medication dosage level is appropriate for the particular patient under the physiological condition at the time of the dosage level determination.

In still a further aspect, user or patient feedback on current or prior medication dosage levels may be used in conjunction with the contextual based medication dosage query and determination to improve the user or patient's therapy management. In this manner, in aspects of the present disclosure, there are provided health monitor devices, such as glucose meters and monitoring systems with improved and robust functionalities providing comprehensive and easy to use therapy management devices and/or systems. In a certain aspect, the health monitor devices may be configured to provide medication dosage calculation, such as single dose of rapid or fast acting insulin, long acting insulin, or combinations thereof, and further configured to incorporate additional features to improve the management of the management and/or treatment of medical conditions such as diabetes, for example.

In accordance with aspects of the present disclosure, the program instructions and/or associated application for execution by the one or more processor driven devices such as, for example, the health monitor device 100 (FIG. 1) may be transferred over data network for installation and subsequent execution by the devices that are downloading the applications, for example, the health monitor device 100. For example, the application associated with the various program instructions for implementing the medication dose calculation function may be downloadable over the air (OTA) over a cellular network and installed in one or more devices in communication in the cellular network. In addition, the executable program or application may be installed for execution in the one or more components of devices in the various systems described above, over a data network such as the internet, a local area network, a wide area network and the like.

Moreover, in aspects of the present disclosure, the various components of the overall systems described above including, for example, the health monitor device, data processing terminal or remote computing device (such as a personal computer terminal or server terminal) as described above may each be configured for bi-directional or uni-directional communication over one or more data communication networks to communicate with other devices and/or components, including, for example, infusion devices, analyte monitoring device such as continuous glucose monitoring system, computer terminals at a hospital or a healthcare provider's office, the patient or user's residence or office, or the device/component vendor/supplier or manufacturer (for example, the vendor or manufacturer of the test strips, insulin, and lancing device and the like) or any other location where the network component is capable of wired or wireless communication over a data network with other devices or components in data communication over the data network. Additionally, secure encrypted data communication may be provided, including encryption based on public/private key pair, password protection and the like to maintain a desired level of security of the data transferred.

In one embodiment, a device may comprise, one or more processors, and a memory for storing instructions coupled to the one or more processors which, when executed by the one or more processors, causes the one or more processors to detect an analyte sample, determine an analyte concentration associated with the detected analyte sample, retrieve stored one or more dose determination information and associated analyte concentration associated with the retrieved one or more dose determination information, and determine a current dose level based at least in part on the determined analyte concentration and the retrieved prior dose determination information, wherein the determined current dose level includes a predetermined type of medication classification.

The medication classification may include one or more of long acting insulin and rapid acting insulin.

The analyte concentration may be associated with a blood glucose concentration.

The analyte concentration may be associated with a fasting blood glucose concentration.

The retrieved prior dose determination information may include prior administered medication level information.

The prior administered medication level information may include prior stored one or more of long acting insulin dose amount, or a rapid acting insulin dose amount.

Further, each of the retrieved one or more prior dose determination information may be associated with one or more of administered medication dose time information, administered dose frequency information over a predetermined time period, or administered medication dose amount.

In one aspect, the device may include an output unit coupled to the one or more processors, wherein the memory for storing instructions coupled to the one or more processors which, when executed by the one or more processors causes the one or more processors to output one or more of the determined current dose level, determined analyte concentration, retrieved stored one or more dose determination information, analyte concentration associated with the retrieved one or more dose determination information, or a request for one or more predetermined information.

The output unit may include one or more of a visual output unit, an audible output unit, or a vibratory output unit, or one or more combinations thereof.

The one or more predetermined information may include a request for an additional analyte sample, or a request to confirm the determined current dose level.

In another aspect, the device may include an input unit coupled to the one or more processors, wherein the memory for storing instructions coupled to the one or more processors which, when executed by the one or more processors causes the one or more processors to detect one or more input commands received from the input unit.

The one or more input commands may include an acknowledgement confirming the determined current dose level.

The one or more input commands may include a rejection of the determined current dose level.

The one or more input commands may include a request to recalculate the current dose level.

In yet another aspect, the device may include a communication module operatively coupled to the one or more processors, the communication module configured to transmit one or more of the determined current dose level or the determined analyte concentration to a remote location.

The communication module may include one or more of an RF transmitter, an RF transceiver, a ZigBee® communication module, a WiFi communication module, a Bluetooth® communication module, an infrared communication module, or a wired communication module.

In another embodiment, a method may comprise detecting an analyte sample, determining an analyte concentration associated with the detected analyte sample, retrieving stored one or more dose determination information and associated analyte concentration associated with the retrieved one or more dose determination information, and determining a current dose level based at least in part on the determined analyte concentration and the retrieved prior dose determination information, wherein the determined current dose level includes a predetermined type of medication classification.

The medication classification may include one or more of long acting insulin and rapid acting insulin.

The analyte concentration may be associated with a blood glucose concentration.

The analyte concentration may be associated with a fasting blood glucose concentration.

The retrieved prior dose determination information may include prior administered medication level information.

Further, the prior administered medication level information may include prior stored one or more of long acting insulin dose amount, or a rapid acting insulin dose amount.

Each of the retrieved one or more prior dose determination information may be associated with one or more of administered medication dose time information, administered dose frequency information over a predetermined time period, or administered medication dose amount.

In one aspect, the method may include outputting one or more information associated with the one or more of the determined current dose level, determined analyte concentration, retrieved stored one or more dose determination information, analyte concentration associated with the retrieved one or more dose determination information, or a request for one or more predetermined information.

The outputting of one or more information may include outputting a visual indication, an audible indication, a vibratory indication, or one or more combinations thereof.

The one or more predetermined information may include a request for an additional analyte sample, or a request to confirm the determined current dose level.

In another aspect, the method may include detecting one or more input commands received from the input unit.

The one or more input commands may include an acknowledgement confirming the determined current dose level.

The one or more input commands may include a rejection of the determined current dose level.

The one or more input commands may include a request to recalculate the current dose level.

In yet another aspect, the method may include transmitting one or more of the determined current dose level or the determined analyte concentration to a remote location.

Transmitting may include transmitting over one or more of an RF transmission protocol, a ZigBee® transmission protocol, a WiFi transmission protocol, a Bluetooth® transmission protocol, an infrared transmission protocol, or a wired transmission protocol.

In another embodiment, a glucose meter may comprise a housing, a memory device coupled to the housing, a controller unit coupled to the housing and the memory device, an input unit coupled to the controller unit and the housing for inputting one or more commands or information, an output unit coupled to the controller unit and the housing for outputting one or more output data, and a strip port provided on the housing configured to receive an analyte test strip, the controller unit configured to determine an analyte concentration based at least in part on the analyte sample on the received analyte test strip, wherein the controller unit is configured to retrieve one or more routines stored in the memory device to determine a medication dose amount based at least in part on the determined analyte concentration.

The determined medication dose amount may include a bolus dose amount.

The determined medication dose amount may include an insulin dose amount or a glucagon dose amount.

The determined medication dose amount may include one or more of a rapid acting insulin dose or a long acting insulin dose.

The output unit may include one or more of a visual display unit, an audible output unit, or a vibratory output unit.

The determined analyte concentration may include a blood glucose concentration.

The controller unit may be configured to store one or more of the determined analyte concentration or the medication dose amount.

In one aspect, the meter may include a communication module coupled to the controller unit, the communication module configured to, at least in part, communicate one or more of the determined analyte concentration or the medication dose amount to a remote location.

The remote location may include a medication delivery device.

The medication delivery device may include an insulin delivery device.

In one embodiment, a method of providing therapy management may include receiving a request for a therapy profile for treating a medical condition, determining using a processor a plurality of therapy profile parameters, assigning a weighted value to each therapy profile parameter based on a hierarchy determined by the medical condition, querying a database to identify a stored therapy profile with therapy profile parameters that most closely correspond to the determined plurality of therapy profile parameters based on the hierarchy, and generating an output data corresponding to the identified stored therapy profile, wherein the output data may include a medication dosage information.

The outputted medication dosage information may include a medication delivery amount or duration or both for the treatment of the medical condition.

Assigning the weighted value to each therapy profile parameter may include ranking the therapy profile parameters in a predetermined order and assigning a respective weighted value based on the ranking.

Querying the database may include matching each determined therapy profile parameter with a respective therapy profile parameter stored in the database and correlated with a stored therapy profile.

Therapy profile parameters of the identified stored therapy profile may most closely match the respective therapy profile parameters of the requested therapy profile.

The therapy profile parameters of the identified stored therapy profile may most closely match the respective therapy profile parameters of the requested therapy profile based on a temporal attribute.

The temporal attribute may include a time of day information or time duration information corresponding to the stored therapy profile and the requested therapy profile.

The time of day information may include a start time associated with the stored therapy profile and the requested therapy profile.

The time duration information may include a duration information associated with the stored therapy profile and the requested therapy profile.

Furthermore, one aspect may include storing the output data in the database.

Moreover, another aspect may include outputting the output data on a user interface component.

The output data may include a medication dose recommendation information.

The medication dose recommendation information may include a medication dose amount information, a medication dose administration time duration information, a medication dose administration time information, or one or more combinations thereof.

The requested therapy profile may include the identified stored therapy profile.

The hierarchy determined by the medical condition for assigning the weighted value to each therapy profile parameter may include a user defined hierarchy.

The hierarchy determined by the medical condition for assigning the weighted value to each therapy profile parameter may include a predetermined order of importance of each therapy profile parameter.

The predetermined order may be stored in the database.

The stored therapy profiles may include one or more of a correction bolus amount delivered, a carbohydrate bolus amount delivered, a basal profile delivered, or one or more combinations thereof.

Querying the database may include performing a statistical analysis based on the information stored in the database.

The statistical analysis may include one or more of mean deviation analysis, standard deviation analysis, estimation analysis, forecasting analysis, correlation of the one or more parameters, modeling of one or more relationships among the one or more parameters, regression analysis, time series analysis, autoregressive modeling, integrated modeling, moving average modeling, data mining, or probability analysis.

Another aspect may include receiving a test sample, wherein one or more of the plurality of therapy profile parameters are based at least in part on the received test sample.

In another embodiment, a glucose monitoring apparatus may include a housing, one or more processing units provided in the housing, and a memory coupled to the one or more processing units and provided in the housing for storing instructions which, when executed by the one or more processing units, causes the one or more processing units to receive a request for a therapy profile for treating a medical condition, determine a plurality of therapy profile parameters, assign a weighted value to each therapy profile parameter based on a hierarchy determined by the medical condition, query the memory to identify a stored therapy profile with therapy profile parameters that most closely correspond to the determined plurality of therapy profile parameters based on the hierarchy, and generate an output data corresponding to the identified stored therapy profile, wherein the output data may include a medication dosage information.

The outputted medication dosage information may include a medication delivery amount or duration or both for the treatment of the medical condition.

The memory coupled to the one or more processing units and provided in the housing for storing instructions which, when executed by the one or more processing units, may cause the one or more processing units to assign the weighted value to each therapy profile parameter which may include ranking the therapy profile parameters in a predetermined order and assigning a respective weighted value based on the ranking.

The memory coupled to the one or more processing units and provided in the housing for storing instructions which, when executed by the one or more processing units, may cause the one or more processing units to match each determined therapy profile parameter with a respective therapy profile parameter stored in the memory and correlated with a stored therapy profile.

Therapy profile parameters of the identified stored therapy profile may most closely match the respective therapy profile parameters of the requested therapy profile.

The therapy profile parameters of the identified stored therapy profile may most closely match the respective therapy profile parameters of the requested therapy profile based on a temporal attribute.

The temporal attribute may include a time of day information or time duration information corresponding to the stored therapy profile and the requested therapy profile.

The time of day information may include a start time associated with the stored therapy profile and the requested therapy profile.

The time duration information may include a duration information associated with the stored therapy profile and the requested therapy profile.

The memory coupled to the one or more processing units and provided in the housing for storing instructions which, when executed by the one or more processing units, may cause the one or more processing units to store the output data in the memory.

Furthermore, in one aspect a user interface component may be coupled to the housing, and wherein the memory coupled to the one or more processing units and provided in the housing for storing instructions which, when executed by the one or more processing units, may cause the one or more processing units to output the output data on the user interface component.

The output data may include a medication dose recommendation information.

The medication dose recommendation information may include a medication dose amount information, a medication dose administration time duration information, a medication dose administration time information, or one or more combinations thereof.

The requested therapy profile may include the identified stored therapy profile.

The hierarchy determined by the medical condition for assigning the weighted value to each therapy profile parameter may include a user defined hierarchy.

The hierarchy determined by the medical condition for assigning the weighted value to each therapy profile parameter may include a predetermined order of importance of each therapy profile parameter.

The predetermined order may be stored in the memory.

The stored therapy profiles may include one or more of a correction bolus amount delivered, a carbohydrate bolus amount delivered, a basal profile delivered, or one or more combinations thereof.

The memory coupled to the one or more processing units and provided in the housing for storing instructions which, when executed by the one or more processing units, may cause the one or more processing units to perform a statistical analysis based on the information stored in the memory.

The statistical analysis may include one or more of mean deviation analysis, standard deviation analysis, estimation analysis, forecasting analysis, correlation of the one or more parameters, modeling of one or more relationships among the one or more parameters, regression analysis, time series analysis, autoregressive modeling, integrated modeling, moving average modeling, data mining, or probability analysis.

Another aspect may include a test strip port provided on the housing, the test strip port configured to receive a test strip with a test sample provided thereon, wherein the memory coupled to the one or more processing units and provided in the housing for storing instructions which, when executed by the one or more processing units, causes the one or more processing units to determine one or more of the plurality of therapy profile parameters based at least in part on the test sample.

The test strip may include an in vitro blood glucose test strip.

The memory coupled to the one or more processing units and provided in the housing for storing instructions which, when executed by the one or more processing units, may cause the one or more processing units to determine a blood glucose concentration based on the received test sample.

The various processes described above including the processes operating in the software application execution environment overall systems described above performing the various functions including those routines described in conjunction with FIGS. 3-5, 8-13, and 15-22, may be embodied as computer programs developed using an object oriented language that allows the modeling of complex systems with modular objects to create abstractions that are representative of real world, physical objects and their interrelationships. The software required to carry out the inventive process, which may be stored in the storage unit of one or more components in the one or more overall system described above, may be developed by a person of ordinary skill in the art and may include one or more computer program products.

Various other modifications and alterations in the structure and method of operation of the present disclosure will be apparent to those skilled in the art without departing from the scope and spirit of the present disclosure. Although the present disclosure has been described in connection with specific preferred embodiments, it should be understood that the present disclosure as claimed should not be unduly limited to such specific embodiments.

What is claimed is:

1. A method of providing therapy management, comprising:
   receiving a request for a therapy profile for treating a medical condition;
   determining, using one or more computing processors, a plurality of therapy profile parameters;
   assigning, using the one or more processors, a weighted value to each therapy profile parameter based on a hierarchy determined by the medical condition, wherein assigning the weighted value to each therapy profile parameter includes ranking the therapy profile parameters in a predetermined order and assigning a respective weighted value based on the ranking;
   querying, using the one or more processors, a database to identify a stored therapy profile with therapy profile parameters that most closely correspond to the determined plurality of therapy profile parameters based on the hierarchy; and
   generating, using the one or more processors, an output data corresponding to the identified stored therapy profile, wherein the output data includes a medication dosage information.

2. The method of claim 1, wherein the outputted medication dosage information includes a medication delivery amount or duration or both for the treatment of the medical condition.

3. The method of claim 1, wherein querying the database includes matching each determined therapy profile parameter with a respective therapy profile parameter stored in the database.

4. The method of claim 3, wherein the therapy profile parameters of the identified stored therapy profile most closely match the respective therapy profile parameter of the requested therapy profile.

5. The method of claim 4, wherein the therapy profile parameters of the identified stored therapy profile most closely match the respective therapy profile parameter of the requested therapy profile based on a temporal attribute.

6. The method of claim 5, wherein the temporal attribute includes a time of day information or time duration information corresponding to the stored therapy profile and the requested therapy profile.

7. The method of claim 6, wherein the time of day information includes a start time associated with the stored therapy profile and the requested therapy profile.

8. The method of claim 6, wherein the time duration information includes a duration information associated with the stored therapy profile and the requested therapy profile.

9. The method of claim 1, further including storing the output data in the database.

10. The method of claim 1, further including outputting the output data on a user interface component.

11. The method of claim 1, wherein the output data includes a medication dose recommendation information.

12. The method of claim 11, wherein the medication dose recommendation information includes a medication dose amount information, a medication dose administration time duration information, a medication dose administration time information, or one or more combinations thereof.

13. The method of claim 1, wherein the requested therapy profile includes the identified stored therapy profile.

14. The method of claim 1, wherein the hierarchy determined by the medical condition for assigning the weighted value to each therapy profile parameter includes a user defined hierarchy.

15. The method of claim 1, wherein the hierarchy determined by the medical condition for assigning the weighted value to each therapy profile parameter includes a predetermined order of importance of each therapy profile parameter.

16. The method of claim 15, wherein the predetermined order of importance is stored in the database.

17. The method of claim 1, wherein the stored therapy profile include one or more of a correction bolus amount delivered, a carbohydrate bolus amount delivered, a basal profile delivered, or one or more combinations thereof.

18. The method of claim 1, wherein querying the database includes performing a statistical analysis based on the medication dosage information stored in the database.

19. The method of claim 18, wherein the statistical analysis includes one or more of mean deviation analysis, standard deviation analysis, estimation analysis, forecasting analysis, correlation of one or more parameters, modeling of one or more relationships among the one or more parameters, regression analysis, time series analysis, autoregressive modeling, integrated modeling, moving average modeling, data mining, or probability analysis.

20. The method of claim 1, further including receiving a test sample, wherein one or more of the plurality of therapy profile parameters is based at least in part on the received test sample.

21. The method of claim 1, further including determining a hierarchy of the plurality of therapy profile parameters.

22. The method of claim 21, wherein determining the hierarchy of the plurality of therapy profile parameters is based on at least one of a level of relevance, a temporal occurrence, a user identified ranking of importance, a healthcare provider identified ranking of importance, a similarity, a dissimilarity, an occurrence prior to another event, an occurrence after another event, and an occurrence in conjunction with a predetermined physiological condition.

23. A glucose monitoring apparatus, comprising:
a housing;
one or more computing processing units provided in the housing; and
a memory coupled to the one or more processing units and provided in the housing for storing instructions which, when executed by the one or more processing units, causes the one or more processing units to receive a request for a therapy profile for treating a medical condition, determine a plurality of therapy profile parameters, assign a weighted value to each therapy profile parameter based on a hierarchy determined by the medical condition, wherein assigning the weighted value to each therapy profile parameter including ranking the therapy profile parameters in a predetermined order and assigning a respective weighted value based on the ranking, query the memory to identify a stored therapy profile with therapy profile parameters that most closely correspond to the determined plurality of therapy profile parameters based on the hierarchy, and generate an output data corresponding to the identified stored therapy profile, wherein the output data includes a medication dosage information.

24. The apparatus of claim 23, wherein the outputted medication dosage information includes a medication delivery amount or duration or both for the treatment of the medical condition.

25. The apparatus of claim 23, wherein the memory coupled to the one or more processing units and provided in the housing for storing instructions which, when executed by the one or more processing units, causes the one or more processing units to match each determined therapy profile parameter with a respective therapy profile parameter stored in the memory.

26. The apparatus of claim 25, wherein the therapy profile parameters of the identified stored therapy profile most closely match the respective therapy profile parameter of the requested therapy profile.

27. The apparatus of claim 26, wherein the therapy profile parameters of the identified stored therapy profile most closely match the respective therapy profile parameter of the requested therapy profile based on a temporal attribute.

28. The apparatus of claim 27, wherein the temporal attribute includes a time of day information or time duration information corresponding to the stored therapy profile and the requested therapy profile.

29. The apparatus of claim 28, wherein the time of day information includes a start time associated with the stored therapy profile and the requested therapy profile.

30. The apparatus of claim 28, wherein the time duration information includes a duration information associated with the stored therapy profile and the requested therapy profile.

31. The apparatus of claim 23, wherein the memory coupled to the one or more processing units and provided in the housing for storing instructions which, when executed by the one or more processing units, causes the one or more processing units to store the output data in the memory.

32. The apparatus of claim 23, further including a user interface component coupled to the housing, and wherein the memory coupled to the one or more processing units and provided in the housing for storing instructions which, when executed by the one or more processing units, causes the one or more processing units to output the output data on the user interface component.

33. The apparatus of claim 23, wherein the output data includes a medication dose recommendation information.

34. The apparatus of claim 33, wherein the medication dose recommendation information includes a medication dose amount information, a medication dose administration time duration information, a medication dose administration time information, or one or more combinations thereof.

35. The apparatus of claim 23, wherein the requested therapy profile includes the identified stored therapy profile.

36. The apparatus of claim 23, wherein the hierarchy determined by the medical condition for assigning the weighted value to each therapy profile parameter includes a user defined hierarchy.

37. The apparatus of claim 23, wherein the hierarchy determined by the medical condition for assigning the weighted value to each therapy profile parameter includes a predetermined order of importance of each therapy profile parameter.

38. The apparatus of claim 37, wherein the predetermined order of importance is stored in the memory.

39. The apparatus of claim 23, wherein the stored therapy profile includes one or more of a correction bolus amount delivered, a carbohydrate bolus amount delivered, a basal profile delivered, or one or more combinations thereof.

40. The apparatus of claim 23, wherein the memory coupled to the one or more processing units and provided in the housing for storing instructions which, when executed by the one or more processing units, causes the one or more processing units to perform a statistical analysis based on the medication dosage information stored in the memory.

41. The apparatus of claim 40, wherein the statistical analysis includes one or more of mean deviation analysis, standard deviation analysis, estimation analysis, forecasting analysis, correlation of one or more parameters, modeling of one or more relationships among the one or more parameters, regression analysis, time series analysis, autoregressive modeling, integrated modeling, moving average modeling, data mining, or probability analysis.

42. The apparatus of claim 23, further including a test strip port provided on the housing, the test strip port configured to receive a test strip with a test sample provided thereon, wherein the memory coupled to the one or more processing units and provided in the housing for storing instructions which, when executed by the one or more processing units, causes the one or more processing units to determine one or more of the plurality of therapy profile parameters based at least in part on the test sample.

43. The apparatus of claim 42, wherein the test strip includes an in vitro blood glucose test strip.

44. The apparatus of claim 42, wherein the memory coupled to the one or more processing units and provided in the housing for storing instructions which, when executed by the one or more processing units, causes the one or more processing units to determine a blood glucose concentration based on the received test sample.

45. The apparatus of claim 23, wherein the memory coupled to the one or more processing units and provided in the housing for storing instructions which, when executed by the one or more processing units, causes the one or more processing units to determine a hierarchy of the plurality of therapy profile parameters.

46. The apparatus of claim 45, wherein determining the hierarchy of the plurality of therapy profile parameters is based on at least one of a level of relevance, a temporal occurrence, a user identified ranking of importance, a healthcare provider identified ranking of importance, a similarity, a dissimilarity, an occurrence prior to another event, an occurrence after another event, and an occurrence in conjunction with a predetermined physiological condition.

* * * * *